US011608486B2

(12) United States Patent
Jones et al.

(10) Patent No.: US 11,608,486 B2
(45) Date of Patent: Mar. 21, 2023

(54) CELL GROWTH WITH MECHANICAL STIMULI

(71) Applicant: Terumo BCT, Inc., Lakewood, CO (US)

(72) Inventors: Mark E. Jones, Littleton, CO (US); Brian J. Nankervis, Golden, CO (US); Kristina E. Fuerst, Durham, NC (US); Jon A. Dodd, Littleton, CO (US)

(73) Assignee: Terumo BCT, Inc., Lakewood, CO (US)

(*) Notice: Subject to any disclaimer, the term of this patent is extended or adjusted under 35 U.S.C. 154(b) by 19 days.

(21) Appl. No.: 15/852,689

(22) Filed: Dec. 22, 2017

(65) Prior Publication Data

US 2018/0142199 A1 May 24, 2018

Related U.S. Application Data

(63) Continuation of application No. PCT/US2016/040855, filed on Jul. 1, 2016.

(60) Provisional application No. 62/188,332, filed on Jul. 2, 2015.

(51) Int. Cl.
*C12M 1/42* (2006.01)
*C12M 1/12* (2006.01)
*C12M 3/00* (2006.01)
*C12M 3/06* (2006.01)

(52) U.S. Cl.
CPC .............. *C12M 35/04* (2013.01); *C12M 3/00* (2013.01); *C12M 21/08* (2013.01); *C12M 25/10* (2013.01); *C12M 25/12* (2013.01); *C12M 27/14* (2013.01)

(58) Field of Classification Search
CPC ...... C12M 35/04; C12M 25/10; C12M 25/12; C12M 27/14
See application file for complete search history.

(56) References Cited

U.S. PATENT DOCUMENTS

| | | |
|---|---|---|
| 2,997,077 A | 8/1961 | Rodrigues |
| 3,013,435 A | 12/1961 | Rodrigues |
| 3,067,915 A | 12/1962 | Shapiro et al. |
| 3,191,807 A | 6/1965 | Rodrigues |
| 3,283,727 A | 11/1966 | Rodrigues |
| 3,701,717 A | 10/1972 | Ingvorsen |
| 3,821,087 A | 6/1974 | Knazek et al. |
| 3,896,061 A | 7/1975 | Tanzawa et al. |
| 4,173,415 A | 11/1979 | Wyatt |
| 4,301,010 A | 11/1981 | Eddleman et al. |
| 4,301,118 A | 11/1981 | Eddleman et al. |
| 4,391,912 A | 7/1983 | Yoshida et al. |
| 4,412,990 A | 11/1983 | Lundblad et al. |
| 4,418,691 A | 12/1983 | Yannas et al. |
| 4,439,322 A | 3/1984 | Sonoda et al. |
| 4,439,901 A | 4/1984 | Eddleman |
| 4,478,829 A | 10/1984 | Landaburu et al. |
| 4,486,188 A | 12/1984 | Altshuler et al. |
| 4,509,695 A | 4/1985 | Bessman |
| 4,585,654 A | 4/1986 | Landaburu et al. |
| 4,618,586 A | 10/1986 | Walker |
| 4,629,686 A | 12/1986 | Gruenberg |
| 4,647,539 A | 3/1987 | Bach |
| 4,650,766 A | 3/1987 | Harm et al. |
| 4,670,544 A | 6/1987 | Schwinn et al. |
| 4,722,902 A | 2/1988 | Harm et al. |
| 4,727,059 A | 2/1988 | Binder et al. |
| 4,804,628 A | 2/1989 | Cracauer et al. |
| 4,828,706 A | 5/1989 | Eddleman |
| 4,885,087 A | 12/1989 | Kopf |
| 4,889,812 A | 12/1989 | Guinn et al. |
| 4,894,342 A | 1/1990 | Guinn et al. |
| 4,897,358 A | 1/1990 | Carrasco |
| 4,918,019 A | 4/1990 | Guinn |
| 4,960,521 A | 10/1990 | Keller |
| 4,973,558 A | 11/1990 | Wilson et al. |
| 4,988,623 A | 1/1991 | Schwarz et al. |
| 5,015,585 A | 5/1991 | Robinson |
| 5,019,054 A | 5/1991 | Clement et al. |
| 5,079,168 A | 1/1992 | Amiot |
| 5,126,238 A | 6/1992 | Gebhard et al. |
| 5,130,141 A | 7/1992 | Law et al. |

(Continued)

FOREIGN PATENT DOCUMENTS

| | | |
|---|---|---|
| CA | 1016332 A | 8/1977 |
| CN | 102406926 A | 4/2012 |

(Continued)

OTHER PUBLICATIONS

Ballermann et al., "Adhesion and Differentiation of Endothelial Cells by Exposure to Chronic Shear Stress: A Vascular Graft Model", Blood Purification, vol. 13, No. 3-4, pp. 125-134, Jan. 1, 1995.
Dekker et al., "Prolonged Fluid Shear Stress Induces A Distinct Set of Endothelial Cell Genes, Most Specifically Lung Kruppel-Like Factor (KLF2)", Blood, vol. 100, No. 5, pp. 1689-1698, Sep. 1, 2002.
Gloeckner et al., "New Miniaturized Hollow-Fiber Bioreactor for in Vivo Like Cell Culture, Cell Expansion, and Production of Cell-Derived Products", Biotechnology Progress, vol. 17, pp. 828-831, Aug. 21, 2001.
Hanley et al., "Efficient Manufacturing of Therapeutic Mesenchymal Stromal Cells with the Use of the Quantum Cell Expansion System", Cytotherapy, vol. 16, No. 8, pp. 1048-1058, Aug. 1, 2014.

(Continued)

*Primary Examiner* — Kara D Johnson
(74) *Attorney, Agent, or Firm* — Harness, Dickey & Pierce, P.L.C.

(57) ABSTRACT

Embodiments for loading and expanding particular cell types are described. Embodiments may include the use of hollow fiber membranes with particular characteristic such as hollow fibers with inner diameters that provide mechanical stimulus (e.g., radius of curvature greater than a dimension of a cell). In addition, embodiments may provide for manipulation of flow rates and other features that also provide mechanical stimuli and promote or enhance the growth of particular types of cells.

20 Claims, 19 Drawing Sheets

(56) References Cited

U.S. PATENT DOCUMENTS

| | | |
|---|---|---|
| 5,149,544 A | 9/1992 | Gentile et al. |
| 5,162,225 A | 11/1992 | Sager et al. |
| 5,169,930 A | 12/1992 | Ruoslahti et al. |
| 5,192,553 A | 3/1993 | Boyse et al. |
| 5,197,985 A | 3/1993 | Caplan et al. |
| 5,202,254 A | 4/1993 | Amiot et al. |
| 5,225,346 A | 7/1993 | Matsumiya et al. |
| 5,226,914 A | 7/1993 | Caplan et al. |
| 5,240,614 A | 8/1993 | Ofsthun et al. |
| 5,240,861 A | 8/1993 | Bieri |
| 5,283,058 A | 2/1994 | Faustman |
| 5,310,676 A | 5/1994 | Johansson et al. |
| 5,324,428 A | 6/1994 | Flaherty |
| 5,330,915 A | 7/1994 | Wilson et al. |
| 5,342,752 A | 8/1994 | Platz et al. |
| 5,399,493 A | 3/1995 | Emerson et al. |
| 5,416,022 A | 5/1995 | Amiot |
| 5,422,197 A | 6/1995 | Zito |
| 5,436,151 A | 7/1995 | McGlave et al. |
| 5,437,994 A | 8/1995 | Emerson et al. |
| 5,439,757 A | 8/1995 | Zito |
| 5,459,069 A | 10/1995 | Palsson et al. |
| 5,460,964 A | 10/1995 | McGlave et al. |
| H1509 H | 12/1995 | Eran et al. |
| 5,478,739 A | 12/1995 | Slivka et al. |
| 5,486,359 A | 1/1996 | Caplan et al. |
| 5,496,659 A | 3/1996 | Zito |
| 5,507,949 A | 4/1996 | Ho |
| 5,510,257 A | 4/1996 | Sirkar et al. |
| 5,512,180 A | 4/1996 | Ho |
| 5,527,467 A | 6/1996 | Ofsthun et al. |
| 5,541,105 A | 7/1996 | Melink et al. |
| 5,543,316 A | 8/1996 | Zawadzka et al. |
| 5,545,492 A | 8/1996 | Zito |
| 5,549,674 A | 8/1996 | Humes et al. |
| 5,571,720 A | 11/1996 | Grandies et al. |
| 5,591,625 A | 1/1997 | Gerson et al. |
| 5,593,580 A | 1/1997 | Kopf |
| 5,595,909 A | 1/1997 | Hu et al. |
| 5,599,703 A | 2/1997 | Davis et al. |
| 5,605,822 A | 2/1997 | Emerson et al. |
| 5,605,829 A | 2/1997 | McGlave et al. |
| 5,605,835 A | 2/1997 | Hu et al. |
| 5,622,857 A | 4/1997 | Goffe |
| 5,626,731 A | 5/1997 | Cooley et al. |
| 5,627,070 A | 5/1997 | Gruenberg |
| 5,631,006 A | 5/1997 | Melink et al. |
| 5,635,386 A | 6/1997 | Palsson et al. |
| 5,635,387 A | 6/1997 | Fei et al. |
| 5,643,736 A | 7/1997 | Bruder et al. |
| 5,646,043 A | 7/1997 | Emerson et al. |
| 5,654,186 A | 8/1997 | Cerami et al. |
| 5,656,421 A | 8/1997 | Gebhard et al. |
| 5,658,995 A | 8/1997 | Kohn et al. |
| 5,667,985 A | 9/1997 | O'Leary et al. |
| 5,670,147 A | 9/1997 | Emerson et al. |
| 5,670,351 A | 9/1997 | Emerson et al. |
| 5,674,750 A | 10/1997 | Kraus et al. |
| 5,684,712 A | 11/1997 | Goffe et al. |
| 5,686,289 A | 11/1997 | Humes et al. |
| 5,688,687 A | 11/1997 | Palsson et al. |
| 5,695,989 A | 12/1997 | Kalamasz |
| 5,700,289 A | 12/1997 | Breitbart et al. |
| 5,705,534 A | 1/1998 | D'Agostino et al. |
| 5,707,859 A | 1/1998 | Miller et al. |
| 5,712,163 A | 1/1998 | Parenteau et al. |
| 5,728,581 A | 3/1998 | Schwartz et al. |
| 5,733,541 A | 3/1998 | Taichman et al. |
| 5,733,542 A | 3/1998 | Haynesworth et al. |
| 5,736,396 A | 4/1998 | Bruder et al. |
| 5,744,347 A | 4/1998 | Wagner et al. |
| 5,750,651 A | 5/1998 | Oppermann et al. |
| 5,753,506 A | 5/1998 | Johe |
| 5,763,194 A | 6/1998 | Slowiaczek et al. |
| 5,763,197 A | 6/1998 | Tsukamoto et al. |
| 5,763,261 A | 6/1998 | Gruenberg |
| 5,763,266 A | 6/1998 | Palsson et al. |
| 5,766,944 A | 6/1998 | Ruiz |
| 5,772,994 A | 6/1998 | Ildstad et al. |
| 5,783,075 A | 7/1998 | Eddleman et al. |
| 5,783,216 A | 7/1998 | Faustman |
| 5,785,912 A | 7/1998 | Cooley et al. |
| 5,804,446 A | 9/1998 | Cerami et al. |
| 5,806,529 A | 9/1998 | Reisner et al. |
| 5,807,686 A | 9/1998 | Wagner et al. |
| 5,811,094 A | 9/1998 | Caplan et al. |
| 5,811,397 A | 9/1998 | Francavilla et al. |
| 5,817,773 A | 10/1998 | Wilson et al. |
| 5,821,218 A | 10/1998 | Toback et al. |
| 5,827,735 A | 10/1998 | Young et al. |
| 5,827,740 A | 10/1998 | Pittenger |
| 5,830,921 A | 11/1998 | Cooley et al. |
| 5,833,979 A | 11/1998 | Schinstine et al. |
| 5,837,258 A | 11/1998 | Grotendorst |
| 5,837,539 A | 11/1998 | Caplan et al. |
| 5,840,502 A | 11/1998 | Van Vlasselaer |
| 5,840,576 A | 11/1998 | Schinstine et al. |
| 5,840,580 A | 11/1998 | Terstappen et al. |
| 5,842,477 A | 12/1998 | Naughton et al. |
| 5,843,633 A | 12/1998 | Yin et al. |
| 5,846,796 A | 12/1998 | Gerami et al. |
| 5,853,247 A | 12/1998 | Shroyer |
| 5,853,717 A | 12/1998 | Schinstine et al. |
| 5,855,608 A | 1/1999 | Brekke et al. |
| 5,855,613 A | 1/1999 | Antanavich et al. |
| 5,855,619 A | 1/1999 | Caplan et al. |
| 5,858,747 A | 1/1999 | Schinstine et al. |
| 5,858,782 A | 1/1999 | Long et al. |
| 5,861,315 A | 1/1999 | Nakahata |
| 5,866,115 A | 2/1999 | Kanz et al. |
| 5,866,420 A | 2/1999 | Talbot et al. |
| 5,868,930 A | 2/1999 | Kopf |
| 5,882,295 A | 3/1999 | Kope |
| 5,882,918 A | 3/1999 | Goffe |
| 5,882,929 A | 3/1999 | Fofonoff et al. |
| 5,888,807 A | 3/1999 | Palsson et al. |
| 5,902,741 A | 5/1999 | Purchio et al. |
| 5,906,827 A | 5/1999 | Khouri et al. |
| 5,906,934 A | 5/1999 | Grande et al. |
| 5,908,782 A | 6/1999 | Marshak et al. |
| 5,908,784 A | 6/1999 | Johnstone et al. |
| 5,912,177 A | 6/1999 | Turner et al. |
| 5,914,108 A | 6/1999 | Tsukamoto et al. |
| 5,922,597 A | 7/1999 | Verfaillie et al. |
| 5,922,847 A | 7/1999 | Broudy et al. |
| 5,925,567 A | 7/1999 | Kraus et al. |
| 5,928,945 A | 7/1999 | Seliktar et al. |
| 5,935,849 A | 8/1999 | Schinstine et al. |
| 5,938,929 A | 8/1999 | Shimagaki et al. |
| 5,939,323 A | 8/1999 | Valentini et al. |
| 5,942,225 A | 8/1999 | Bruder et al. |
| 5,955,353 A | 9/1999 | Amiot |
| 5,958,763 A | 9/1999 | Goffe |
| 5,965,436 A | 10/1999 | Thiede et al. |
| 5,972,703 A | 10/1999 | Long et al. |
| 5,980,795 A | 11/1999 | Klotzer et al. |
| 5,981,211 A | 11/1999 | Hu et al. |
| 5,981,708 A | 11/1999 | Lawman et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,001,643 A | 12/1999 | Spaulding |
| 6,001,647 A | 12/1999 | Peck et al. |
| 6,004,743 A | 12/1999 | Kenyon et al. |
| 6,010,696 A | 1/2000 | Caplan et al. |
| 6,015,554 A | 1/2000 | Galy |
| 6,022,540 A | 2/2000 | Bruder et al. |
| 6,022,742 A | 2/2000 | Kopf |
| 6,022,743 A | 2/2000 | Naughton et al. |
| 6,027,743 A | 2/2000 | Khouri et al. |
| 6,030,836 A | 2/2000 | Thiede et al. |
| 6,040,180 A | 3/2000 | Johe |
| 6,045,818 A | 4/2000 | Cima et al. |

(56) References Cited

U.S. PATENT DOCUMENTS

| | | |
|---|---|---|
| 6,048,721 A | 4/2000 | Armstrong et al. |
| 6,048,727 A | 4/2000 | Kopf |
| 6,049,026 A | 4/2000 | Muschler |
| 6,054,121 A | 4/2000 | Cerami et al. |
| 6,060,270 A | 5/2000 | Humes |
| 6,066,317 A | 5/2000 | Yang et al. |
| 6,071,691 A | 6/2000 | Hoekstra et al. |
| 6,074,366 A | 6/2000 | Rogers et al. |
| 6,082,364 A | 7/2000 | Balian et al. |
| 6,083,747 A | 7/2000 | Wong et al. |
| 6,086,643 A | 7/2000 | Clark et al. |
| 6,087,113 A | 7/2000 | Caplan et al. |
| 6,096,532 A | 8/2000 | Armstrong et al. |
| 6,096,537 A | 8/2000 | Chappel |
| 6,103,117 A | 8/2000 | Shimagaki et al. |
| 6,103,522 A | 8/2000 | Torok-Storb et al. |
| 6,110,176 A | 8/2000 | Shapira |
| 6,110,482 A | 8/2000 | Khouri et al. |
| 6,114,307 A | 9/2000 | Jaspers et al. |
| 6,117,985 A | 9/2000 | Thomas et al. |
| 6,120,491 A | 9/2000 | Kohn et al. |
| 6,127,141 A | 10/2000 | Kopf |
| 6,129,911 A | 10/2000 | Faris |
| 6,143,293 A | 11/2000 | Weiss et al. |
| 6,146,360 A | 11/2000 | Rogers et al. |
| 6,146,888 A | 11/2000 | Smith et al. |
| 6,149,902 A | 11/2000 | Artavanis-Tsakonas et al. |
| 6,149,906 A | 11/2000 | Mosca |
| 6,150,164 A | 11/2000 | Humes |
| 6,152,964 A | 11/2000 | Van Blitterswijk et al. |
| 6,162,643 A | 12/2000 | Wille, Jr. |
| 6,165,225 A | 12/2000 | Antanavich et al. |
| 6,165,785 A | 12/2000 | Ogle et al. |
| 6,174,333 B1 | 1/2001 | Kadiyala et al. |
| 6,174,526 B1 | 1/2001 | Cerami et al. |
| 6,174,666 B1 | 1/2001 | Pavlakis et al. |
| 6,179,871 B1 | 1/2001 | Halpern |
| 6,197,325 B1 | 3/2001 | MacPhee et al. |
| 6,197,575 B1 | 3/2001 | Griffith et al. |
| 6,200,606 B1 | 3/2001 | Peterson et al. |
| 6,214,369 B1 | 4/2001 | Grande et al. |
| 6,214,574 B1 | 4/2001 | Kopf |
| 6,224,860 B1 | 5/2001 | Brown |
| 6,225,119 B1 | 5/2001 | Qasba et al. |
| 6,225,368 B1 | 5/2001 | D'Agostino et al. |
| 6,228,117 B1 | 5/2001 | De Bruijn et al. |
| 6,228,607 B1 | 5/2001 | Kersten et al. |
| 6,228,635 B1 | 5/2001 | Armstrong et al. |
| 6,238,908 B1 | 5/2001 | Armstrong et al. |
| 6,239,157 B1 | 5/2001 | Mbalaviele |
| 6,242,252 B1 | 6/2001 | Reid et al. |
| 6,248,319 B1 | 6/2001 | Zsebo et al. |
| 6,248,587 B1 | 6/2001 | Rodgers et al. |
| 6,255,112 B1 | 7/2001 | Thiede et al. |
| 6,258,597 B1 | 7/2001 | Bachovchin et al. |
| 6,258,778 B1 | 7/2001 | Rodgers et al. |
| 6,261,549 B1 | 7/2001 | Fernandez et al. |
| 6,280,718 B1 | 8/2001 | Kaufman et al. |
| 6,280,724 B1 | 8/2001 | Moore |
| 6,281,012 B1 | 8/2001 | McIntosh et al. |
| 6,281,195 B1 | 8/2001 | Rueger et al. |
| 6,287,864 B1 | 9/2001 | Bagnis et al. |
| 6,291,249 B1 | 9/2001 | Mahant et al. |
| 6,297,213 B1 | 10/2001 | Oppermann et al. |
| 6,299,650 B1 | 10/2001 | Van Blitterswijk et al. |
| 6,306,424 B1 | 10/2001 | Vyakarnam et al. |
| 6,306,575 B1 | 10/2001 | Thomas et al. |
| 6,322,784 B1 | 11/2001 | Pittenger et al. |
| 6,322,786 B1 | 11/2001 | Anderson |
| 6,326,198 B1 | 12/2001 | Emerson et al. |
| 6,326,201 B1 | 12/2001 | Fung et al. |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |
| 6,338,942 B2 | 1/2002 | Kraus et al. |
| 6,340,592 B1 | 1/2002 | Stringer |
| 6,342,370 B1 | 1/2002 | Connolly et al. |
| 6,355,239 B1 | 3/2002 | Bruder et al. |
| 6,358,252 B1 | 3/2002 | Shapira |
| 6,361,997 B1 | 3/2002 | Huss |
| 6,365,149 B2 | 4/2002 | Vyakarnam et al. |
| 6,368,636 B1 | 4/2002 | McIntosh et al. |
| 6,372,210 B2 | 4/2002 | Brown |
| 6,372,244 B1 | 4/2002 | Antanavich et al. |
| 6,372,494 B1 | 4/2002 | Naughton et al. |
| 6,372,892 B1 | 4/2002 | Ballinger et al. |
| 6,376,742 B1 | 4/2002 | Zdrahala et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,387,693 B2 | 5/2002 | Rieser et al. |
| 6,387,964 B1 | 5/2002 | D'Agostino et al. |
| 6,392,118 B1 | 5/2002 | Hammang et al. |
| 6,394,812 B1 | 5/2002 | Sullivan et al. |
| 6,399,580 B1 | 6/2002 | Elias et al. |
| 6,410,320 B1 | 6/2002 | Humes |
| 6,414,219 B1 | 7/2002 | Denhardt et al. |
| 6,416,496 B1 | 7/2002 | Rogers et al. |
| 6,417,205 B1 | 7/2002 | Cooke et al. |
| 6,419,829 B2 | 7/2002 | Ho et al. |
| 6,420,138 B1 | 7/2002 | Gentz et al. |
| 6,423,681 B1 | 7/2002 | Barasch et al. |
| 6,426,332 B1 | 7/2002 | Rueger et al. |
| 6,428,802 B1 | 8/2002 | Atala |
| 6,429,012 B1 | 8/2002 | Kraus et al. |
| 6,429,013 B1 | 8/2002 | Halvorsen et al. |
| 6,432,653 B1 | 8/2002 | Okarma |
| 6,432,711 B1 | 8/2002 | Dinsmore et al. |
| 6,440,407 B1 | 8/2002 | Bauer et al. |
| 6,440,734 B1 | 8/2002 | Pykett et al. |
| 6,451,562 B1 | 9/2002 | Ruben et al. |
| 6,454,811 B1 | 9/2002 | Sherwood et al. |
| 6,455,678 B1 | 9/2002 | Yin et al. |
| 6,458,585 B1 | 10/2002 | Vachula et al. |
| 6,458,589 B1 | 10/2002 | Rambhatla et al. |
| 6,461,495 B1 | 10/2002 | Morrissey et al. |
| 6,461,853 B1 | 10/2002 | Zhu |
| 6,464,983 B1 | 10/2002 | Grotendorst |
| 6,465,205 B2 | 10/2002 | Hicks, Jr. |
| 6,465,247 B1 | 10/2002 | Weissman et al. |
| 6,465,249 B2 | 10/2002 | Reya et al. |
| 6,468,794 B1 | 10/2002 | Uchida et al. |
| 6,472,200 B1 | 10/2002 | Mitrani |
| 6,475,481 B2 | 11/2002 | Talmadge |
| 6,479,064 B1 | 11/2002 | Atala |
| 6,482,231 B1 | 11/2002 | Abatangelo et al. |
| 6,482,411 B1 | 11/2002 | Ahuja et al. |
| 6,482,645 B2 | 11/2002 | Atala |
| 6,482,926 B1 | 11/2002 | Thomas et al. |
| 6,488,925 B2 | 12/2002 | Ruben et al. |
| 6,491,918 B1 | 12/2002 | Thomas et al. |
| 6,495,129 B1 | 12/2002 | Li et al. |
| 6,495,364 B2 | 12/2002 | Hammang et al. |
| 6,497,875 B1 | 12/2002 | Sorrell et al. |
| 6,498,034 B1 | 12/2002 | Strobl |
| 6,506,574 B1 | 1/2003 | Rambhatla et al. |
| 6,511,510 B1 | 1/2003 | de Bruijn et al. |
| 6,511,767 B1 | 1/2003 | Calver et al. |
| 6,511,958 B1 | 1/2003 | Atkinson et al. |
| 6,514,514 B1 | 2/2003 | Atkinson et al. |
| 6,524,452 B1 | 2/2003 | Clark et al. |
| 6,528,052 B1 | 3/2003 | Smith et al. |
| 6,528,245 B2 | 3/2003 | Sanchez-Ramos et al. |
| 6,531,445 B1 | 3/2003 | Cohen et al. |
| 6,534,084 B1 | 3/2003 | Vyakarnam et al. |
| 6,537,807 B1 | 3/2003 | Smith et al. |
| 6,541,024 B1 | 4/2003 | Kadiyala et al. |
| 6,541,249 B2 | 4/2003 | Wager et al. |
| 6,544,506 B2 | 4/2003 | Reisner |
| 6,548,734 B1 | 4/2003 | Glimcher et al. |
| 6,555,324 B1 | 4/2003 | Olweus et al. |
| 6,555,374 B1 | 4/2003 | Gimble et al. |
| 6,559,119 B1 | 5/2003 | Burgess et al. |

(56) References Cited

U.S. PATENT DOCUMENTS

| | | |
|---|---|---|
| 6,562,616 B1 | 5/2003 | Toner et al. |
| 6,565,843 B1 | 5/2003 | Cohen et al. |
| 6,566,126 B2 | 5/2003 | Cadwell |
| 6,569,421 B2 | 5/2003 | Hodges |
| 6,569,427 B1 | 5/2003 | Boyse et al. |
| 6,569,428 B1 | 5/2003 | Isner et al. |
| 6,569,654 B2 | 5/2003 | Shastri et al. |
| 6,576,188 B1 | 6/2003 | Rose et al. |
| 6,576,428 B1 | 6/2003 | Assenmacher et al. |
| 6,576,464 B2 | 6/2003 | Gold et al. |
| 6,576,465 B1 | 6/2003 | Long |
| 6,582,471 B1 | 6/2003 | Bittmann et al. |
| 6,582,955 B2 | 6/2003 | Martinez et al. |
| 6,586,192 B1 | 7/2003 | Peschle et al. |
| 6,589,728 B2 | 7/2003 | Csete et al. |
| 6,589,786 B1 | 7/2003 | Mangano et al. |
| 6,596,274 B1 | 7/2003 | Abatangelo et al. |
| 6,599,300 B2 | 7/2003 | Vibe-Hansen et al. |
| 6,599,520 B2 | 7/2003 | Scarborough et al. |
| 6,610,535 B1 | 8/2003 | Lu et al. |
| 6,613,798 B1 | 9/2003 | Porter et al. |
| 6,616,912 B2 | 9/2003 | Eddleman et al. |
| 6,617,070 B1 | 9/2003 | Morrissey et al. |
| 6,617,152 B2 | 9/2003 | Bryhan et al. |
| 6,617,159 B1 | 9/2003 | Cancedda et al. |
| 6,623,749 B2 | 9/2003 | Williams et al. |
| 6,623,942 B2 | 9/2003 | Ruben et al. |
| 6,624,108 B1 | 9/2003 | Clark et al. |
| 6,626,950 B2 | 9/2003 | Brown et al. |
| 6,627,191 B1 | 9/2003 | Bartelmez et al. |
| 6,632,425 B1 | 10/2003 | Li et al. |
| 6,632,620 B1 | 10/2003 | Makarovskiy |
| 6,632,934 B1 | 10/2003 | Moreadith et al. |
| 6,638,765 B1 | 10/2003 | Rosenberg |
| 6,642,019 B1 | 11/2003 | Anderson et al. |
| 6,642,048 B2 | 11/2003 | Xu et al. |
| 6,642,049 B1 | 11/2003 | Chute et al. |
| 6,642,201 B1 | 11/2003 | Khavinson et al. |
| 6,645,489 B2 | 11/2003 | Pykett et al. |
| 6,645,727 B2 | 11/2003 | Thomas et al. |
| 6,645,763 B2 | 11/2003 | Kobayashi et al. |
| 6,649,189 B2 | 11/2003 | Talmadge et al. |
| 6,649,595 B2 | 11/2003 | Clackson et al. |
| 6,649,631 B1 | 11/2003 | Orme et al. |
| 6,653,105 B2 | 11/2003 | Triglia et al. |
| 6,653,134 B2 | 11/2003 | Prockop et al. |
| 6,660,523 B2 | 12/2003 | Blom et al. |
| 6,662,805 B2 | 12/2003 | Frondoza et al. |
| 6,667,034 B2 | 12/2003 | Palsson et al. |
| 6,667,176 B1 | 12/2003 | Funk et al. |
| 6,670,169 B1 | 12/2003 | Schob et al. |
| 6,670,175 B2 | 12/2003 | Wang et al. |
| 6,673,603 B2 | 1/2004 | Baetge et al. |
| 6,673,606 B1 | 1/2004 | Tennekoon et al. |
| 6,677,306 B1 | 1/2004 | Veis et al. |
| 6,683,192 B2 | 1/2004 | Baxter et al. |
| 6,685,936 B2 | 2/2004 | McIntosh et al. |
| 6,685,971 B2 | 2/2004 | Xu |
| 6,686,198 B1 | 2/2004 | Melton et al. |
| 6,696,575 B2 | 2/2004 | Schmidt et al. |
| 6,699,716 B2 | 3/2004 | Sullivan et al. |
| 6,703,017 B1 | 3/2004 | Peck et al. |
| 6,703,209 B1 | 3/2004 | Baetscher et al. |
| 6,706,293 B1 | 3/2004 | Quintanilla Almagro et al. |
| 6,709,864 B1 | 3/2004 | Pittenger et al. |
| 6,712,850 B2 | 3/2004 | Vyakarnam et al. |
| 6,719,969 B1 | 4/2004 | Hogaboam et al. |
| 6,719,970 B1 | 4/2004 | Costantino et al. |
| 6,720,340 B1 | 4/2004 | Cooke et al. |
| 6,730,314 B2 | 5/2004 | Jeschke et al. |
| 6,730,315 B2 | 5/2004 | Usala et al. |
| 6,730,510 B2 | 5/2004 | Roos et al. |
| 6,733,746 B2 | 5/2004 | Daley et al. |
| 6,734,000 B2 | 5/2004 | Chin et al. |
| 6,740,493 B1 | 5/2004 | Long et al. |
| 6,759,039 B2 | 7/2004 | Tsang et al. |
| 6,759,245 B1 | 7/2004 | Toner et al. |
| 6,761,883 B2 | 7/2004 | Weissman et al. |
| 6,761,887 B1 | 7/2004 | Kavalkovich et al. |
| 6,767,699 B2 | 7/2004 | Polo et al. |
| 6,767,737 B1 | 7/2004 | Wilson et al. |
| 6,767,738 B1 | 7/2004 | Gage et al. |
| 6,767,740 B2 | 7/2004 | Sramek et al. |
| 6,770,478 B2 | 8/2004 | Crowe et al. |
| 6,777,227 B2 | 8/2004 | Ricci et al. |
| 6,777,231 B1 | 8/2004 | Katz et al. |
| 6,780,612 B1 | 8/2004 | Ford et al. |
| 6,787,355 B1 | 9/2004 | Miller et al. |
| 6,790,455 B2 | 9/2004 | Chu et al. |
| 6,793,939 B2 | 9/2004 | Badylak |
| 6,797,269 B2 | 9/2004 | Mosca et al. |
| 6,797,514 B2 | 9/2004 | Berenson et al. |
| 6,800,480 B1 | 10/2004 | Bodnar et al. |
| 6,802,971 B2 | 10/2004 | Gorsuch et al. |
| 6,805,860 B1 | 10/2004 | Alt |
| 6,809,117 B2 | 10/2004 | Enikolopov et al. |
| 6,811,773 B1 | 11/2004 | Gentz et al. |
| 6,811,776 B2 | 11/2004 | Kale et al. |
| 6,814,961 B1 | 11/2004 | Jensen et al. |
| 6,821,513 B1 | 11/2004 | Fleming |
| 6,821,790 B2 | 11/2004 | Mahant et al. |
| 6,828,145 B2 | 12/2004 | Avital et al. |
| 6,833,269 B2 | 12/2004 | Carpenter |
| 6,835,377 B2 | 12/2004 | Goldberg et al. |
| 6,835,566 B2 | 12/2004 | Smith et al. |
| 6,838,284 B2 | 1/2005 | de Bruijn et al. |
| 6,841,150 B2 | 1/2005 | Halvorsen et al. |
| 6,841,151 B2 | 1/2005 | Stringer |
| 6,841,294 B1 | 1/2005 | Morrissey et al. |
| 6,841,355 B2 | 1/2005 | Livant |
| 6,841,386 B2 | 1/2005 | Kraus et al. |
| 6,841,542 B2 | 1/2005 | Bartelmez et al. |
| 6,844,011 B1 | 1/2005 | Faustman |
| 6,844,187 B1 | 1/2005 | Weschler et al. |
| 6,849,051 B2 | 2/2005 | Sramek et al. |
| 6,849,255 B2 | 2/2005 | Gazit et al. |
| 6,849,454 B2 | 2/2005 | Kelly et al. |
| 6,849,662 B2 | 2/2005 | Enikolopov et al. |
| 6,852,308 B2 | 2/2005 | Kohn et al. |
| 6,852,321 B2 | 2/2005 | Colucci et al. |
| 6,852,533 B1 | 2/2005 | Rafii et al. |
| 6,855,242 B1 | 2/2005 | Comninellis et al. |
| 6,855,542 B2 | 2/2005 | DiMilla et al. |
| 6,863,900 B2 | 3/2005 | Kadiyala et al. |
| 6,866,843 B2 | 3/2005 | Habener et al. |
| 6,872,389 B1 | 3/2005 | Faris |
| 6,875,430 B2 | 4/2005 | McIntosh et al. |
| 6,887,600 B2 | 5/2005 | Morrissey et al. |
| 6,887,704 B2 | 5/2005 | Peled et al. |
| 6,908,763 B1 | 6/2005 | Akashi et al. |
| 6,911,201 B1 | 6/2005 | Merchav et al. |
| 6,914,279 B2 | 7/2005 | Lu et al. |
| 6,939,955 B2 | 9/2005 | Rameshwar |
| 6,943,008 B1 | 9/2005 | Ma |
| 6,965,018 B2 | 11/2005 | Mikesell et al. |
| 6,969,308 B2 | 11/2005 | Doi et al. |
| 6,979,308 B2 | 12/2005 | McDonald et al. |
| 6,979,321 B2 | 12/2005 | Geis et al. |
| 6,988,004 B2 | 1/2006 | Kanno et al. |
| 7,008,394 B2 | 3/2006 | Geise et al. |
| 7,015,037 B1 | 3/2006 | Furcht et al. |
| 7,029,666 B2 | 4/2006 | Bruder et al. |
| 7,033,339 B1 | 4/2006 | Lynn |
| 7,033,823 B2 | 4/2006 | Chang |
| 7,041,493 B2 | 5/2006 | Rao |
| 7,045,098 B2 | 5/2006 | Stephens |
| 7,052,517 B2 | 5/2006 | Murphy et al. |
| 7,056,493 B2 | 6/2006 | Kohn et al. |
| 7,112,441 B2 | 9/2006 | Uemura et al. |
| 7,118,672 B2 | 10/2006 | Husain et al. |
| 7,122,178 B1 | 10/2006 | Simmons et al. |
| 7,160,719 B2 | 1/2007 | Nyberg |
| 7,169,295 B2 | 1/2007 | Husain et al. |
| 7,172,696 B1 | 2/2007 | Martinez et al. |

(56) References Cited

U.S. PATENT DOCUMENTS

| | | |
|---|---|---|
| 7,175,763 B2 | 2/2007 | Husain et al. |
| 7,192,776 B2 | 3/2007 | Stephens |
| 7,195,711 B2 | 3/2007 | Gorsuch et al. |
| 7,250,154 B2 | 7/2007 | Kohn et al. |
| 7,270,996 B2 | 9/2007 | Cannon et al. |
| 7,271,234 B2 | 9/2007 | Kohn et al. |
| 7,294,259 B2 | 11/2007 | Cote et al. |
| 7,300,571 B2 | 11/2007 | Cote et al. |
| 7,303,676 B2 | 12/2007 | Husain et al. |
| 7,303,677 B2 | 12/2007 | Cote et al. |
| 7,341,062 B2 | 3/2008 | Chachques et al. |
| 7,358,001 B2 | 4/2008 | Morrissey et al. |
| 7,361,493 B1 | 4/2008 | Hammond et al. |
| 7,368,169 B2 | 5/2008 | Kohn et al. |
| 7,378,271 B2 | 5/2008 | Bader |
| 7,399,872 B2 | 7/2008 | Webster et al. |
| 7,416,884 B2 | 8/2008 | Gemmiti et al. |
| 7,425,440 B2 | 9/2008 | Malinge et al. |
| 7,435,586 B2 | 10/2008 | Bartlett et al. |
| 7,438,902 B2 | 10/2008 | Habener et al. |
| 7,439,057 B2 | 10/2008 | Frangos et al. |
| 7,452,529 B2 | 11/2008 | Brown, Jr. et al. |
| 7,491,388 B1 | 2/2009 | Mc Intosh et al. |
| 7,494,811 B2 | 2/2009 | Wolfinbarger, Jr. et al. |
| 7,514,074 B2 | 4/2009 | Pittenger et al. |
| 7,514,075 B2 | 4/2009 | Hedrick et al. |
| 7,524,676 B2 | 4/2009 | Reiter et al. |
| 7,531,351 B2 | 5/2009 | Marx et al. |
| 7,534,601 B2 | 5/2009 | Wikswo et al. |
| 7,534,609 B2 | 5/2009 | Merchav et al. |
| 7,572,374 B2 | 8/2009 | Gorsuch et al. |
| 7,579,179 B2 | 8/2009 | Bryhan et al. |
| 7,585,412 B2 | 9/2009 | Gorsuch et al. |
| 7,588,938 B2 | 9/2009 | Ma |
| 7,598,075 B2 | 10/2009 | Smith et al. |
| 7,608,447 B2 | 10/2009 | Cohen et al. |
| 7,659,118 B2 | 2/2010 | Furcht et al. |
| 7,678,573 B2 | 3/2010 | Merchav et al. |
| 7,682,822 B2 | 3/2010 | Noll et al. |
| 7,682,823 B1 | 3/2010 | Runyon |
| 7,718,430 B2 | 5/2010 | Antwiler |
| 7,722,896 B2 | 5/2010 | Kohn et al. |
| D620,732 S | 8/2010 | Andrews |
| 7,838,122 B2 | 11/2010 | Kohn et al. |
| 7,838,289 B2 | 11/2010 | Furcht et al. |
| 7,892,829 B2 | 2/2011 | Pittenger et al. |
| 7,919,307 B2 | 4/2011 | Klaus et al. |
| 7,927,587 B2 | 4/2011 | Blazer et al. |
| 7,989,851 B2 | 8/2011 | Lu et al. |
| 8,008,528 B2 | 8/2011 | Kohn et al. |
| 8,034,365 B2 | 10/2011 | Baluca |
| 8,075,881 B2 | 12/2011 | Verfaillie et al. |
| 8,147,824 B2 | 4/2012 | Maziarz et al. |
| 8,147,863 B2 | 4/2012 | Kohn et al. |
| 8,158,120 B2 | 4/2012 | Pittenger et al. |
| 8,158,121 B2 | 4/2012 | Pittenger et al. |
| 8,252,280 B1 | 8/2012 | Verfaillie et al. |
| 8,252,887 B2 | 8/2012 | Bolikal et al. |
| 8,288,159 B2 | 10/2012 | Warren et al. |
| 8,288,590 B2 | 10/2012 | Kohn et al. |
| 8,298,823 B2 | 10/2012 | Warren et al. |
| 8,309,347 B2 | 11/2012 | Antwiler |
| 8,361,453 B2 | 1/2013 | Uhrich et al. |
| 8,377,683 B2 | 2/2013 | Lu et al. |
| 8,383,397 B2 | 2/2013 | Wojciechowski et al. |
| 8,383,806 B2 | 2/2013 | Rameshwar |
| 8,399,245 B2 | 3/2013 | Leuthaeuser et al. |
| 8,415,449 B2 | 4/2013 | Kohn et al. |
| 8,435,781 B2 | 5/2013 | Kodama |
| 8,461,289 B2 | 6/2013 | Kohn et al. |
| 8,476,399 B2 | 7/2013 | Bolikal et al. |
| 8,486,621 B2 | 7/2013 | Luo et al. |
| 8,486,695 B2 | 7/2013 | Danilkovitch et al. |
| 8,492,140 B2 | 7/2013 | Smith et al. |
| 8,492,150 B2 | 7/2013 | Parker et al. |
| 8,524,496 B2 | 9/2013 | Meiron et al. |
| 8,529,888 B2 | 9/2013 | Meiron et al. |
| 8,540,499 B2 | 9/2013 | Page et al. |
| 8,551,511 B2 | 10/2013 | Brandom et al. |
| 8,580,249 B2 | 11/2013 | Blazar et al. |
| 8,678,638 B2 | 3/2014 | Wong |
| 8,785,181 B2 | 7/2014 | Antwiler |
| 8,852,570 B2 | 10/2014 | Pittenger et al. |
| 8,852,571 B2 | 10/2014 | Pittenger et al. |
| 8,852,572 B2 | 10/2014 | Pittenger et al. |
| 8,852,573 B2 | 10/2014 | Pittenger et al. |
| 8,852,574 B2 | 10/2014 | Pittenger et al. |
| 8,852,575 B2 | 10/2014 | Pittenger et al. |
| 8,895,291 B2 | 11/2014 | DiLorenzo et al. |
| 9,057,045 B2 | 6/2015 | Gibbons et al. |
| 9,109,193 B2 | 8/2015 | Galliher et al. |
| 9,175,259 B2 * | 11/2015 | Nankervis ............ C12N 5/0081 |
| 9,220,810 B2 | 12/2015 | Ma et al. |
| 9,441,195 B2 | 9/2016 | Wojciechowski et al. |
| 9,534,198 B2 | 1/2017 | Page et al. |
| 9,732,313 B2 | 8/2017 | Hirschel et al. |
| 10,093,956 B2 | 10/2018 | Hirschel et al. |
| 10,494,421 B2 | 12/2019 | Castillo |
| 2001/0017188 A1 | 8/2001 | Cooley et al. |
| 2001/0020086 A1 | 9/2001 | Hubbell et al. |
| 2001/0021516 A1 | 9/2001 | Wei et al. |
| 2001/0029046 A1 | 10/2001 | Beaulieu |
| 2001/0033834 A1 | 10/2001 | Wilkison et al. |
| 2001/0036663 A1 | 11/2001 | Kraus et al. |
| 2001/0041687 A1 | 11/2001 | Mruk |
| 2001/0044413 A1 | 11/2001 | Pierce et al. |
| 2001/0049139 A1 | 12/2001 | Lagasse et al. |
| 2002/0015724 A1 | 2/2002 | Yang et al. |
| 2002/0018804 A1 | 2/2002 | Austin et al. |
| 2002/0028510 A1 | 3/2002 | Sanberg et al. |
| 2002/0031757 A1 | 3/2002 | Ohgushi et al. |
| 2002/0037278 A1 | 3/2002 | Ueno et al. |
| 2002/0045260 A1 | 4/2002 | Hung et al. |
| 2002/0064869 A1 | 5/2002 | Ebner et al. |
| 2002/0076400 A1 | 6/2002 | Katz et al. |
| 2002/0077687 A1 | 6/2002 | Ahn |
| 2002/0082698 A1 | 6/2002 | Parenteau et al. |
| 2002/0116054 A1 | 8/2002 | Lundell et al. |
| 2002/0128581 A1 | 9/2002 | Vishnoi et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0130100 A1 | 9/2002 | Smith |
| 2002/0132343 A1 | 9/2002 | Lum |
| 2002/0139743 A1 | 10/2002 | Critz et al. |
| 2002/0142457 A1 | 10/2002 | Umezawa et al. |
| 2002/0146678 A1 | 10/2002 | Benvenisty |
| 2002/0146817 A1 | 10/2002 | Cannon et al. |
| 2002/0150989 A1 | 10/2002 | Greene et al. |
| 2002/0151056 A1 | 10/2002 | Sasai et al. |
| 2002/0159981 A1 | 10/2002 | Peled et al. |
| 2002/0160032 A1 | 10/2002 | Long et al. |
| 2002/0160510 A1 | 10/2002 | Hariri |
| 2002/0168765 A1 | 11/2002 | Prockop et al. |
| 2002/0169408 A1 | 11/2002 | Beretta et al. |
| 2002/0182241 A1 | 12/2002 | Borenstein et al. |
| 2002/0182664 A1 | 12/2002 | Dolecek et al. |
| 2002/0188962 A1 | 12/2002 | Denhardt et al. |
| 2002/0197240 A1 | 12/2002 | Chiu |
| 2003/0021850 A1 | 1/2003 | Xu |
| 2003/0022390 A1 | 1/2003 | Stephens |
| 2003/0027330 A1 | 2/2003 | Lanza et al. |
| 2003/0027331 A1 | 2/2003 | Yan et al. |
| 2003/0032143 A1 | 2/2003 | Neff et al. |
| 2003/0036168 A1 | 2/2003 | Ni et al. |
| 2003/0040113 A1 | 2/2003 | Mizuno et al. |
| 2003/0049236 A1 | 3/2003 | Kassem et al. |
| 2003/0054331 A1 | 3/2003 | Fraser et al. |
| 2003/0059851 A1 | 3/2003 | Smith |
| 2003/0059939 A1 | 3/2003 | Page et al. |
| 2003/0078345 A1 | 4/2003 | Morrisey |
| 2003/0082795 A1 | 5/2003 | Shuler et al. |
| 2003/0086915 A1 | 5/2003 | Rader et al. |
| 2003/0089471 A1 | 5/2003 | Gehr et al. |

(56) References Cited

U.S. PATENT DOCUMENTS

| | | |
|---|---|---|
| 2003/0092101 A1 | 5/2003 | Ni et al. |
| 2003/0101465 A1 | 5/2003 | Lawman et al. |
| 2003/0103957 A1 | 6/2003 | McKerracher |
| 2003/0104568 A1 | 6/2003 | Lee |
| 2003/0113813 A1 | 6/2003 | Heidaran et al. |
| 2003/0113910 A1 | 6/2003 | Levanduski |
| 2003/0124091 A1 | 7/2003 | Tuse et al. |
| 2003/0124721 A1 | 7/2003 | Cheatham et al. |
| 2003/0130593 A1 | 7/2003 | Gonzalez |
| 2003/0133918 A1 | 7/2003 | Sherley |
| 2003/0138950 A1 | 7/2003 | McAllister et al. |
| 2003/0143727 A1 | 7/2003 | Chang |
| 2003/0148152 A1 | 8/2003 | Morrisey |
| 2003/0149011 A1 | 8/2003 | Ackerman et al. |
| 2003/0152558 A1 | 8/2003 | Luft et al. |
| 2003/0157078 A1 | 8/2003 | Hall et al. |
| 2003/0157709 A1 | 8/2003 | DiMilla et al. |
| 2003/0161817 A1 | 8/2003 | Young et al. |
| 2003/0166272 A1 | 9/2003 | Abuljadayel |
| 2003/0170214 A1 | 9/2003 | Bader |
| 2003/0180296 A1 | 9/2003 | Salcedo et al. |
| 2003/0185817 A1 | 10/2003 | Thomas et al. |
| 2003/0202938 A1 | 10/2003 | Rameshwar |
| 2003/0203483 A1 | 10/2003 | Seshi |
| 2003/0204323 A1 | 10/2003 | Morrisey |
| 2003/0211602 A1 | 11/2003 | Atala |
| 2003/0211603 A1 | 11/2003 | Earp et al. |
| 2003/0216718 A1 | 11/2003 | Hamblin et al. |
| 2003/0219898 A1 | 11/2003 | Sugaya et al. |
| 2003/0223968 A1 | 12/2003 | Yang |
| 2003/0224420 A1 | 12/2003 | Hellerstein et al. |
| 2003/0224510 A1 | 12/2003 | Yamaguchi et al. |
| 2003/0225010 A1 | 12/2003 | Rameshwar |
| 2003/0232432 A1 | 12/2003 | Bhat |
| 2003/0232752 A1 | 12/2003 | Freeman et al. |
| 2003/0235909 A1 | 12/2003 | Hariri et al. |
| 2004/0009158 A1 | 1/2004 | Sands et al. |
| 2004/0009589 A1 | 1/2004 | Levenberg et al. |
| 2004/0010231 A1 | 1/2004 | Leonhardt et al. |
| 2004/0014209 A1 | 1/2004 | Lassar et al. |
| 2004/0018174 A1 | 1/2004 | Palasis |
| 2004/0018617 A1 | 1/2004 | Hwang |
| 2004/0023324 A1 | 2/2004 | Sakano et al. |
| 2004/0023370 A1 | 2/2004 | Yu et al. |
| 2004/0027914 A1 | 2/2004 | Vrane |
| 2004/0033214 A1 | 2/2004 | Young et al. |
| 2004/0033599 A1 | 2/2004 | Rosenberg |
| 2004/0037811 A1 | 2/2004 | Penn et al. |
| 2004/0037815 A1 | 2/2004 | Clarke et al. |
| 2004/0038316 A1 | 2/2004 | Kaiser et al. |
| 2004/0053869 A1 | 3/2004 | Andrews et al. |
| 2004/0062753 A1 | 4/2004 | Rezania et al. |
| 2004/0063205 A1 | 4/2004 | Xu |
| 2004/0067585 A1 | 4/2004 | Wang et al. |
| 2004/0071668 A1 | 4/2004 | Bays et al. |
| 2004/0072259 A1 | 4/2004 | Scadden et al. |
| 2004/0077079 A1 | 4/2004 | Storgaard et al. |
| 2004/0079248 A1 | 4/2004 | Mayer et al. |
| 2004/0087016 A1 | 5/2004 | Keating et al. |
| 2004/0091936 A1 | 5/2004 | West |
| 2004/0096476 A1 | 5/2004 | Uhrich et al. |
| 2004/0097408 A1 | 5/2004 | Leder et al. |
| 2004/0101959 A1 | 5/2004 | Marko et al. |
| 2004/0107453 A1 | 6/2004 | Furcht et al. |
| 2004/0110286 A1 | 6/2004 | Bhatia |
| 2004/0115804 A1 | 6/2004 | Fu et al. |
| 2004/0115806 A1 | 6/2004 | Fu |
| 2004/0120932 A1 | 6/2004 | Zahner |
| 2004/0121461 A1 | 6/2004 | Honmou et al. |
| 2004/0121464 A1 | 6/2004 | Rathjen et al. |
| 2004/0126405 A1 | 7/2004 | Sahatjian et al. |
| 2004/0128077 A1 | 7/2004 | Koebler et al. |
| 2004/0131601 A1 | 7/2004 | Epstein et al. |
| 2004/0132184 A1 | 7/2004 | Dennis et al. |
| 2004/0136967 A1 | 7/2004 | Weiss et al. |
| 2004/0137612 A1 | 7/2004 | Baksh |
| 2004/0137613 A1 | 7/2004 | Vacant et al. |
| 2004/0143174 A1 | 7/2004 | Brubaker |
| 2004/0143863 A1 | 7/2004 | Li et al. |
| 2004/0151700 A1 | 8/2004 | Harlan et al. |
| 2004/0151701 A1 | 8/2004 | Kim et al. |
| 2004/0151706 A1 | 8/2004 | Shakhov et al. |
| 2004/0151729 A1 | 8/2004 | Michalopoulos et al. |
| 2004/0152190 A1 | 8/2004 | Sumita |
| 2004/0161419 A1 | 8/2004 | Strom et al. |
| 2004/0171533 A1 | 9/2004 | Zehentner et al. |
| 2004/0180347 A1 | 9/2004 | Stanton et al. |
| 2004/0191902 A1 | 9/2004 | Hambor et al. |
| 2004/0197310 A1 | 10/2004 | Sanberg et al. |
| 2004/0197375 A1 | 10/2004 | Rezania et al. |
| 2004/0208786 A1 | 10/2004 | Kevy et al. |
| 2004/0214275 A1 | 10/2004 | Soejima et al. |
| 2004/0219134 A1 | 11/2004 | Naughton et al. |
| 2004/0219136 A1 | 11/2004 | Hariri |
| 2004/0219563 A1 | 11/2004 | West et al. |
| 2004/0224403 A1 | 11/2004 | Bhatia |
| 2004/0229351 A1 | 11/2004 | Rodriguez et al. |
| 2004/0234972 A1 | 11/2004 | Owens et al. |
| 2004/0235158 A1 | 11/2004 | Bartlett et al. |
| 2004/0235160 A1 | 11/2004 | Nishikawa et al. |
| 2004/0235166 A1 | 11/2004 | Prockop et al. |
| 2004/0242469 A1 | 12/2004 | Lee et al. |
| 2004/0258669 A1 | 12/2004 | Dzau et al. |
| 2004/0259242 A1 | 12/2004 | Malinge et al. |
| 2004/0259254 A1 | 12/2004 | Honmou et al. |
| 2004/0260058 A1 | 12/2004 | Scheek et al. |
| 2004/0260318 A1 | 12/2004 | Hunter et al. |
| 2004/0265996 A1 | 12/2004 | Schwarz et al. |
| 2005/0002914 A1 | 1/2005 | Rosen et al. |
| 2005/0003460 A1 | 1/2005 | Nilsson et al. |
| 2005/0003527 A1 | 1/2005 | Lang et al. |
| 2005/0003534 A1 | 1/2005 | Huberman et al. |
| 2005/0008624 A1 | 1/2005 | Peled et al. |
| 2005/0008626 A1 | 1/2005 | Fraser et al. |
| 2005/0009178 A1 | 1/2005 | Yost et al. |
| 2005/0009179 A1 | 1/2005 | Gemmiti et al. |
| 2005/0009181 A1 | 1/2005 | Black et al. |
| 2005/0013804 A1 | 1/2005 | Kato et al. |
| 2005/0014252 A1 | 1/2005 | Chu et al. |
| 2005/0014253 A1 | 1/2005 | Ehmann et al. |
| 2005/0014254 A1 | 1/2005 | Kruse |
| 2005/0014255 A1 | 1/2005 | Tang et al. |
| 2005/0019801 A1 | 1/2005 | Rubin et al. |
| 2005/0019908 A1 | 1/2005 | Hariri |
| 2005/0019910 A1 | 1/2005 | Takagi et al. |
| 2005/0019911 A1 | 1/2005 | Gronthos et al. |
| 2005/0026836 A1 | 2/2005 | Dack et al. |
| 2005/0031587 A1 | 2/2005 | Tsutsui et al. |
| 2005/0031595 A1 | 2/2005 | Peled et al. |
| 2005/0031598 A1 | 2/2005 | Levenberg et al. |
| 2005/0032122 A1 | 2/2005 | Hwang et al. |
| 2005/0032207 A1 | 2/2005 | Wobus et al. |
| 2005/0032209 A1 | 2/2005 | Messina et al. |
| 2005/0032218 A1 | 2/2005 | Gerlach |
| 2005/0036980 A1 | 2/2005 | Chaney et al. |
| 2005/0037488 A1 | 2/2005 | Mitalipova et al. |
| 2005/0037490 A1 | 2/2005 | Rosenberg et al. |
| 2005/0037492 A1 | 2/2005 | Xu et al. |
| 2005/0037493 A1 | 2/2005 | Mandalam et al. |
| 2005/0037949 A1 | 2/2005 | O'Brien et al. |
| 2005/0106119 A1 | 5/2005 | Brandom et al. |
| 2005/0106127 A1 | 5/2005 | Kraus et al. |
| 2005/0112447 A1 | 5/2005 | Fletcher et al. |
| 2005/0112762 A1 | 5/2005 | Hart et al. |
| 2005/0118712 A1 | 6/2005 | Tsai et al. |
| 2005/0130297 A1 | 6/2005 | Sarem et al. |
| 2005/0136093 A1 | 6/2005 | Denk |
| 2005/0137517 A1 | 6/2005 | Blickhan et al. |
| 2005/0142162 A1 | 6/2005 | Hunter et al. |
| 2005/0149157 A1 | 7/2005 | Hunter et al. |
| 2005/0152946 A1 | 7/2005 | Hunter et al. |
| 2005/0158289 A1 | 7/2005 | Simmons et al. |
| 2005/0172340 A1 | 8/2005 | Logvinov et al. |
| 2005/0175665 A1 | 8/2005 | Hunter et al. |

(56) References Cited

U.S. PATENT DOCUMENTS

| | | |
|---|---|---|
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0180957 A1 | 8/2005 | Scharp et al. |
| 2005/0181502 A1 | 8/2005 | Furcht et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186671 A1 | 8/2005 | Cannon et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2005/0244963 A1 | 11/2005 | Teplyashin |
| 2005/0249731 A1 | 11/2005 | Aslan et al. |
| 2005/0255118 A1 | 11/2005 | Wehner |
| 2005/0261674 A1 | 11/2005 | Nobis et al. |
| 2005/0277577 A1 | 12/2005 | Hunter et al. |
| 2005/0281790 A1 | 12/2005 | Simmons et al. |
| 2005/0282733 A1 | 12/2005 | Prins et al. |
| 2005/0283844 A1 | 12/2005 | Furcht et al. |
| 2006/0002900 A1 | 1/2006 | Binder et al. |
| 2006/0008452 A1 | 1/2006 | Simmons et al. |
| 2006/0019388 A1 | 1/2006 | Hutmacher et al. |
| 2006/0019389 A1 | 1/2006 | Yayon et al. |
| 2006/0054941 A1 | 3/2006 | Lu et al. |
| 2006/0083720 A1 | 4/2006 | Fraser et al. |
| 2006/0099198 A1 | 5/2006 | Thomson et al. |
| 2006/0166364 A1 | 7/2006 | Senesac |
| 2006/0172008 A1 | 8/2006 | Yayon et al. |
| 2006/0193840 A1 | 8/2006 | Gronthos et al. |
| 2006/0228798 A1 | 10/2006 | Verfaillie et al. |
| 2006/0233834 A1 | 10/2006 | Guehenneux et al. |
| 2006/0239909 A1 | 10/2006 | Anderson et al. |
| 2006/0258586 A1 | 11/2006 | Sheppard et al. |
| 2006/0258933 A1 | 11/2006 | Ellis et al. |
| 2006/0259998 A1 | 11/2006 | Brumbley et al. |
| 2006/0280748 A1 | 12/2006 | Buckheit |
| 2006/0286077 A1 | 12/2006 | Gronthos et al. |
| 2007/0005148 A1 | 1/2007 | Barofsky et al. |
| 2007/0011752 A1 | 1/2007 | Paleyanda |
| 2007/0042462 A1 | 2/2007 | Hildinger |
| 2007/0065938 A1 | 3/2007 | Gronthos et al. |
| 2007/0105222 A1 | 5/2007 | Wolfinbarger et al. |
| 2007/0116612 A1 | 5/2007 | Williamson |
| 2007/0117180 A1 | 5/2007 | Morikawa et al. |
| 2007/0122904 A1 | 5/2007 | Nordon |
| 2007/0123996 A1 | 5/2007 | Sugaya et al. |
| 2007/0160583 A1 | 7/2007 | Lange et al. |
| 2007/0166834 A1 | 7/2007 | Williamson et al. |
| 2007/0178071 A1 | 8/2007 | Westenfelder |
| 2007/0196421 A1 | 8/2007 | Hunter et al. |
| 2007/0197957 A1 | 8/2007 | Hunter et al. |
| 2007/0198063 A1 | 8/2007 | Hunter et al. |
| 2007/0202485 A1 | 8/2007 | Nees et al. |
| 2007/0203330 A1 | 8/2007 | Kretschmar et al. |
| 2007/0208134 A1 | 9/2007 | Hunter et al. |
| 2007/0231305 A1 | 10/2007 | Noll et al. |
| 2007/0258943 A1 | 11/2007 | Penn et al. |
| 2007/0274970 A1 | 11/2007 | Gordon et al. |
| 2007/0275457 A1 | 11/2007 | Granchelli et al. |
| 2007/0295651 A1 | 12/2007 | Martinez et al. |
| 2007/0298015 A1 | 12/2007 | Beer et al. |
| 2007/0298497 A1 | 12/2007 | Antwiler |
| 2008/0003663 A1 | 1/2008 | Bryhan et al. |
| 2008/0009458 A1 | 1/2008 | Dornan et al. |
| 2008/0032398 A1 | 2/2008 | Cannon et al. |
| 2008/0050770 A1 | 2/2008 | Zhang et al. |
| 2008/0063600 A1 | 3/2008 | Aguzzi et al. |
| 2008/0064649 A1 | 3/2008 | Rameshwar |
| 2008/0069807 A1 | 3/2008 | Jy et al. |
| 2008/0095676 A1 | 4/2008 | Andretta |
| 2008/0095690 A1 | 4/2008 | Liu |
| 2008/0103412 A1 | 5/2008 | Chin |
| 2008/0110827 A1 | 5/2008 | Cote et al. |
| 2008/0113426 A1 | 5/2008 | Smith et al. |
| 2008/0113440 A1 | 5/2008 | Gurney et al. |
| 2008/0153077 A1 | 6/2008 | Henry |
| 2008/0160597 A1 | 7/2008 | van der Heiden et al. |
| 2008/0166808 A1 | 7/2008 | Nyberg |
| 2008/0181879 A1 | 7/2008 | Catelas et al. |
| 2008/0190857 A1 | 8/2008 | Beretta et al. |
| 2008/0194017 A1 | 8/2008 | Esser et al. |
| 2008/0206831 A1 | 8/2008 | Coffey et al. |
| 2008/0220522 A1 | 9/2008 | Antwiler |
| 2008/0220523 A1 | 9/2008 | Antwiler |
| 2008/0220524 A1 | 9/2008 | Noll et al. |
| 2008/0220526 A1 | 9/2008 | Ellison et al. |
| 2008/0221443 A1 | 9/2008 | Ritchie et al. |
| 2008/0227189 A1 | 9/2008 | Bader |
| 2008/0227190 A1 | 9/2008 | Antwiler |
| 2008/0248572 A1 | 10/2008 | Antwiler |
| 2008/0254533 A1 | 10/2008 | Antwiler |
| 2008/0268165 A1 | 10/2008 | Fekety et al. |
| 2008/0306095 A1 | 12/2008 | Crawford |
| 2009/0004738 A1 | 1/2009 | Merchav et al. |
| 2009/0011399 A1 | 1/2009 | Fischer |
| 2009/0047289 A1 | 2/2009 | Denhardt et al. |
| 2009/0074728 A1 | 3/2009 | Gronthos et al. |
| 2009/0075881 A1 | 3/2009 | Catelas et al. |
| 2009/0076481 A1 | 3/2009 | Stegmann et al. |
| 2009/0081770 A1 | 3/2009 | Srienc et al. |
| 2009/0081797 A1 | 3/2009 | Fadeev et al. |
| 2009/0092608 A1 | 4/2009 | Ni et al. |
| 2009/0098103 A1 | 4/2009 | Madison et al. |
| 2009/0098645 A1 | 4/2009 | Fang et al. |
| 2009/0100944 A1 | 4/2009 | Newby et al. |
| 2009/0104163 A1 | 4/2009 | Deans et al. |
| 2009/0104692 A1 | 4/2009 | Bartfeld et al. |
| 2009/0104699 A1 | 4/2009 | Newby et al. |
| 2009/0118161 A1 | 5/2009 | Cruz |
| 2009/0181087 A1 | 7/2009 | Kraus et al. |
| 2009/0183581 A1 | 7/2009 | Wilkinson et al. |
| 2009/0191627 A1 | 7/2009 | Fadeev et al. |
| 2009/0191632 A1 | 7/2009 | Fadeev et al. |
| 2009/0191634 A1 | 7/2009 | Martin et al. |
| 2009/0203065 A1 | 8/2009 | Gehman et al. |
| 2009/0203129 A1 | 8/2009 | Furcht et al. |
| 2009/0203130 A1 | 8/2009 | Furcht et al. |
| 2009/0214382 A1 | 8/2009 | Burgess et al. |
| 2009/0214481 A1 | 8/2009 | Muhs et al. |
| 2009/0214652 A1 | 8/2009 | Hunter et al. |
| 2009/0215022 A1 | 8/2009 | Page et al. |
| 2009/0227024 A1 | 9/2009 | Baker et al. |
| 2009/0227027 A1 | 9/2009 | Baker et al. |
| 2009/0233334 A1 | 9/2009 | Hildinger et al. |
| 2009/0233353 A1 | 9/2009 | Furcht et al. |
| 2009/0233354 A1 | 9/2009 | Furcht et al. |
| 2009/0258379 A1 | 10/2009 | Klein et al. |
| 2009/0269841 A1 | 10/2009 | Wojciechowski et al. |
| 2009/0270725 A1 | 10/2009 | Leimbach et al. |
| 2009/0280153 A1 | 11/2009 | Hunter et al. |
| 2009/0280565 A1 | 11/2009 | Jolicoeur et al. |
| 2009/0291890 A1 | 11/2009 | Madison et al. |
| 2010/0009409 A1 | 1/2010 | Hubbell et al. |
| 2010/0021954 A1 | 1/2010 | Deshayes et al. |
| 2010/0021990 A1 | 1/2010 | Edwards et al. |
| 2010/0028311 A1 | 2/2010 | Motlagh et al. |
| 2010/0042260 A1 | 2/2010 | Antwiler |
| 2010/0075410 A1 | 3/2010 | Desai et al. |
| 2010/0086481 A1 | 4/2010 | Baird et al. |
| 2010/0092536 A1 | 4/2010 | Hunter et al. |
| 2010/0093607 A1 | 4/2010 | Dickneite |
| 2010/0105138 A1 | 4/2010 | Dodd et al. |
| 2010/0111910 A1 | 5/2010 | Rakoczy |
| 2010/0129376 A1 | 5/2010 | Denhardt et al. |
| 2010/0129912 A1 | 5/2010 | Su et al. |
| 2010/0136091 A1 | 6/2010 | Moghe et al. |
| 2010/0144037 A1 | 6/2010 | Antwiler |
| 2010/0144634 A1 | 6/2010 | Zheng et al. |
| 2010/0183561 A1 | 7/2010 | Sakthivel et al. |
| 2010/0183585 A1 | 7/2010 | Van Zant et al. |
| 2010/0203020 A1 | 8/2010 | Ghosh |
| 2010/0230203 A1 | 9/2010 | Karayianni |
| 2010/0248366 A1 | 9/2010 | Fadeev et al. |

(56) References Cited

U.S. PATENT DOCUMENTS

| | | |
|---|---|---|
| 2010/0278933 A1 | 11/2010 | Sayeski et al. |
| 2010/0285453 A1 | 11/2010 | Goodrich |
| 2010/0285590 A1 | 11/2010 | Verfaillie et al. |
| 2010/0291180 A1 | 11/2010 | Uhrich |
| 2010/0291181 A1 | 11/2010 | Uhrich et al. |
| 2010/0297234 A1 | 11/2010 | Sugino et al. |
| 2010/0304427 A1 | 12/2010 | Faris et al. |
| 2010/0304482 A1 | 12/2010 | Deshayes et al. |
| 2010/0310524 A1 | 12/2010 | Bechor et al. |
| 2010/0316446 A1 | 12/2010 | Runyon |
| 2011/0085746 A1 | 4/2011 | Wong et al. |
| 2011/0111498 A1 | 5/2011 | Oh et al. |
| 2011/0129447 A1 | 6/2011 | Meretzki et al. |
| 2011/0129486 A1 | 6/2011 | Meiron |
| 2011/0143433 A1 | 6/2011 | Oh et al. |
| 2011/0159584 A1 | 6/2011 | Gibbons et al. |
| 2011/0171182 A1 | 7/2011 | Abelman |
| 2011/0171659 A1 | 7/2011 | Furcht et al. |
| 2011/0177595 A1 | 7/2011 | Furcht et al. |
| 2011/0212493 A1 | 9/2011 | Hirschel et al. |
| 2011/0256108 A1 | 10/2011 | Meiron et al. |
| 2011/0256160 A1 | 10/2011 | Meiron et al. |
| 2011/0293583 A1 | 12/2011 | Aberman |
| 2012/0028352 A1 | 2/2012 | Oh et al. |
| 2012/0051976 A1 | 3/2012 | Lu et al. |
| 2012/0058554 A1 | 3/2012 | Deshayes et al. |
| 2012/0064047 A1 | 3/2012 | Verfaillie et al. |
| 2012/0064583 A1 | 3/2012 | Edwards et al. |
| 2012/0086657 A1 | 4/2012 | Stanton, IV et al. |
| 2012/0088224 A1 | 4/2012 | DiLorenzo et al. |
| 2012/0118919 A1 | 5/2012 | Cianciolo |
| 2012/0122220 A1 | 5/2012 | Merchav et al. |
| 2012/0135043 A1 | 5/2012 | Maziarz et al. |
| 2012/0145580 A1 | 6/2012 | Paruit et al. |
| 2012/0156779 A1 | 6/2012 | Anneren et al. |
| 2012/0178885 A1 | 7/2012 | Kohn et al. |
| 2012/0189713 A1 | 7/2012 | Kohn et al. |
| 2012/0208039 A1 | 8/2012 | Barbaroux et al. |
| 2012/0219531 A1 | 8/2012 | Oh et al. |
| 2012/0219737 A1 | 8/2012 | Sugino et al. |
| 2012/0226013 A1 | 9/2012 | Kohn et al. |
| 2012/0231519 A1 | 9/2012 | Bushman et al. |
| 2012/0237557 A1 | 9/2012 | Lewitus et al. |
| 2012/0295352 A1 | 11/2012 | Antwiler |
| 2012/0308531 A1 | 12/2012 | Pinxteren et al. |
| 2012/0315696 A1 | 12/2012 | Luitjens et al. |
| 2013/0004465 A1 | 1/2013 | Aberman |
| 2013/0039892 A1 | 2/2013 | Aberman |
| 2013/0058907 A1 | 3/2013 | Wojciechowski et al. |
| 2013/0059383 A1 | 3/2013 | Dijkhuizen Borgart et al. |
| 2013/0101561 A1 | 4/2013 | Sabaawy |
| 2013/0143313 A1 | 6/2013 | Niazi |
| 2013/0157353 A1 | 6/2013 | Dijkhuizen Borgart et al. |
| 2013/0259843 A1 | 10/2013 | Duda et al. |
| 2013/0319575 A1 | 12/2013 | Mendyk |
| 2013/0323213 A1 | 12/2013 | Meiron et al. |
| 2013/0337558 A1 | 12/2013 | Meiron et al. |
| 2014/0004553 A1 | 1/2014 | Parker et al. |
| 2014/0017209 A1 | 1/2014 | Aberman et al. |
| 2014/0030805 A1 | 1/2014 | Kasuto et al. |
| 2014/0051162 A1 | 2/2014 | Nankervis |
| 2014/0051167 A1 | 2/2014 | Nankervis et al. |
| 2014/0112893 A1 | 4/2014 | Tom et al. |
| 2014/0186937 A1 | 7/2014 | Smith et al. |
| 2014/0193895 A1 | 7/2014 | Smith et al. |
| 2014/0193911 A1 | 7/2014 | Newby et al. |
| 2014/0242039 A1 | 8/2014 | Meiron et al. |
| 2014/0248244 A1 | 9/2014 | Danilkovitch et al. |
| 2014/0315300 A1 | 10/2014 | Oh et al. |
| 2014/0342448 A1 | 11/2014 | Nagels |
| 2015/0004693 A1 | 1/2015 | Danilkovitch et al. |
| 2015/0104431 A1 | 4/2015 | Pittenger et al. |
| 2015/0111252 A1 | 4/2015 | Hirschel et al. |
| 2015/0125138 A1 | 5/2015 | Karnieli et al. |
| 2015/0175950 A1 | 6/2015 | Hirschel et al. |
| 2015/0225685 A1 | 8/2015 | Hirschel et al. |
| 2015/0247122 A1 | 9/2015 | Tom et al. |
| 2015/0259749 A1 | 9/2015 | Santos et al. |
| 2016/0362650 A1 | 12/2016 | Wojciechowski et al. |
| 2016/0362652 A1 | 12/2016 | Page et al. |
| 2018/0010082 A1 | 1/2018 | Jaques et al. |
| 2018/0030398 A1 | 2/2018 | Castillo |
| 2018/0155668 A1 | 6/2018 | Hirschel et al. |
| 2019/0194628 A1 | 6/2019 | Rao et al. |

FOREIGN PATENT DOCUMENTS

| | | |
|---|---|---|
| DE | 3833925 A1 | 9/1989 |
| DE | 4007703 A1 | 9/1991 |
| DE | 10244859 A1 | 4/2004 |
| DE | 10327988 A1 | 7/2004 |
| DE | 102012200939 A1 | 7/2013 |
| EP | 0220650 A2 | 5/1987 |
| EP | 750938 A1 | 1/1997 |
| EP | 906415 A1 | 4/1999 |
| EP | 959980 A1 | 12/1999 |
| EP | 1007631 A1 | 6/2000 |
| EP | 1028737 A1 | 8/2000 |
| EP | 1028991 A1 | 8/2000 |
| EP | 1066052 A2 | 1/2001 |
| EP | 1066060 A2 | 1/2001 |
| EP | 1084230 A2 | 3/2001 |
| EP | 1147176 A1 | 10/2001 |
| EP | 1220611 A1 | 7/2002 |
| EP | 1223956 A1 | 7/2002 |
| EP | 1325953 A1 | 7/2003 |
| EP | 1437404 A1 | 7/2004 |
| EP | 1437406 A2 | 7/2004 |
| EP | 1447443 A1 | 8/2004 |
| EP | 1452594 A1 | 9/2004 |
| EP | 1062321 B1 | 12/2004 |
| EP | 1484080 A1 | 12/2004 |
| EP | 1498478 A1 | 1/2005 |
| EP | 1036057 B1 | 10/2005 |
| EP | 1605044 A2 | 12/2005 |
| EP | 1756262 A1 | 2/2007 |
| EP | 1771737 A1 | 4/2007 |
| EP | 1882030 A1 | 1/2008 |
| EP | 1908490 A1 | 4/2008 |
| EP | 1971679 A2 | 9/2008 |
| EP | 1991668 A2 | 11/2008 |
| EP | 2200622 A1 | 6/2010 |
| EP | 2208782 A2 | 7/2010 |
| EP | 2264145 A1 | 12/2010 |
| EP | 2027247 B1 | 1/2011 |
| EP | 2303293 A1 | 4/2011 |
| EP | 2311938 A1 | 4/2011 |
| EP | 2331957 A1 | 6/2011 |
| EP | 2334310 A2 | 6/2011 |
| EP | 2334783 A2 | 6/2011 |
| EP | 2361968 A1 | 8/2011 |
| EP | 2366775 A1 | 9/2011 |
| EP | 2465922 A2 | 6/2012 |
| EP | 2481819 A1 | 8/2012 |
| EP | 2548951 A1 | 1/2013 |
| EP | 2561066 A1 | 2/2013 |
| EP | 2575831 A1 | 4/2013 |
| EP | 2591789 A2 | 5/2013 |
| EP | 2624845 A2 | 8/2013 |
| EP | 2626417 A1 | 8/2013 |
| EP | 2641606 A1 | 9/2013 |
| EP | 2689008 A1 | 1/2014 |
| EP | 2694639 A1 | 2/2014 |
| EP | 2697362 A2 | 2/2014 |
| EP | 2739720 A1 | 6/2014 |
| EP | 2807246 A1 | 12/2014 |
| GB | 1414671 A | 11/1975 |
| GB | 2297980 A | 8/1996 |
| GB | 2360789 A | 10/2001 |
| HU | 3285 U | 5/2007 |
| JP | H02245177 A | 9/1990 |
| JP | 2003/052360 A | 2/2003 |
| JP | 2003510068 A | 3/2003 |
| JP | 2005278564 A | 10/2005 |

(56) References Cited

FOREIGN PATENT DOCUMENTS

| | | |
|---|---|---|
| JP | 2007000038 A | 1/2007 |
| JP | 2012506257 A | 3/2012 |
| JP | 5548207 B2 | 7/2014 |
| JP | 2019516029 A | 6/2019 |
| JP | 2019525765 A | 9/2019 |
| KR | 101228026 B1 | 1/2013 |
| KR | 20150002762 A | 1/2015 |
| KR | 101504392 B1 | 3/2015 |
| KR | 101548790 B1 | 8/2015 |
| KR | 101553040 B1 | 9/2015 |
| KR | 20170076679 A | 7/2017 |
| KR | 20180027501 A | 3/2018 |
| KR | 102027596 B1 | 10/2019 |
| KR | 20200034790 A | 3/2020 |
| KR | 20200058433 A | 5/2020 |
| MY | 115206 A | 4/2003 |
| WO | 86/02379 A1 | 4/1986 |
| WO | WO 86/02378 | 4/1986 |
| WO | 88/01643 A1 | 3/1988 |
| WO | 89/12676 A1 | 12/1989 |
| WO | 90/02171 A1 | 3/1990 |
| WO | WO-9013306 A2 | 11/1990 |
| WO | WO-9105238 A1 | 4/1991 |
| WO | 91/07485 A1 | 5/1991 |
| WO | WO-9106641 A1 | 5/1991 |
| WO | WO-9109194 A1 | 6/1991 |
| WO | 92/10564 A1 | 6/1992 |
| WO | WO-94/25571 A1 | 11/1994 |
| WO | 95/04813 A1 | 2/1995 |
| WO | 95/21911 A1 | 8/1995 |
| WO | 95/24468 A1 | 9/1995 |
| WO | WO-96/29395 A1 | 9/1996 |
| WO | WO-96/39035 A1 | 12/1996 |
| WO | WO-97/05826 A1 | 2/1997 |
| WO | 97/16527 A1 | 5/1997 |
| WO | WO-97/29792 A1 | 8/1997 |
| WO | WO-97/39104 A1 | 10/1997 |
| WO | WO-1997-040137 A1 | 10/1997 |
| WO | 98/22588 A2 | 5/1998 |
| WO | WO-98/31403 A1 | 7/1998 |
| WO | 98/53046 A1 | 11/1998 |
| WO | WO-98/51317 A1 | 11/1998 |
| WO | WO-98/51785 A1 | 11/1998 |
| WO | WO-99/05180 A1 | 2/1999 |
| WO | WO-99/24391 A1 | 5/1999 |
| WO | WO-99/24490 A1 | 5/1999 |
| WO | WO-99/27167 A1 | 6/1999 |
| WO | WO-99/49015 A2 | 9/1999 |
| WO | WO-00/06704 A2 | 2/2000 |
| WO | WO-0009018 A1 | 2/2000 |
| WO | WO 00/12676 | 3/2000 |
| WO | WO-OO/16420 A1 | 3/2000 |
| WO | WO-OO/17326 A1 | 3/2000 |
| WO | WO-00/29002 A2 | 5/2000 |
| WO | WO-0032225 A1 | 6/2000 |
| WO | WO-00/44058 A2 | 7/2000 |
| WO | 00/46354 A1 | 8/2000 |
| WO | WO-0054651 A2 | 9/2000 |
| WO | WO-0056405 A2 | 9/2000 |
| WO | WO-00/59933 A2 | 10/2000 |
| WO | WO-00/69449 A2 | 11/2000 |
| WO | 00/75275 A2 | 12/2000 |
| WO | WO-00/75196 A1 | 12/2000 |
| WO | WO-00/77236 A2 | 12/2000 |
| WO | WO-2001/000783 A2 | 1/2001 |
| WO | WO-2001/011011 A2 | 2/2001 |
| WO | WO-2001/018174 A2 | 3/2001 |
| WO | WO-2001/021766 A2 | 3/2001 |
| WO | 01/23520 A1 | 4/2001 |
| WO | WO-2001/025402 A1 | 4/2001 |
| WO | WO-2001/029189 A2 | 4/2001 |
| WO | WO-0122810 A2 | 4/2001 |
| WO | WO-2001/034167 A1 | 5/2001 |
| WO | WO-2001/049851 A1 | 7/2001 |
| WO | WO-2001/054706 A2 | 8/2001 |
| WO | WO-2001-094541 A2 | 12/2001 |
| WO | 02/28996 A1 | 4/2002 |
| WO | WO-2002/042422 A2 | 5/2002 |
| WO | WO-2002/057430 A2 | 7/2002 |
| WO | WO-2002/092794 A2 | 11/2002 |
| WO | WO-2002/101385 A1 | 12/2002 |
| WO | WO-2003/010303 A1 | 2/2003 |
| WO | WO-2003/014313 A2 | 2/2003 |
| WO | WO-2003/016916 A1 | 2/2003 |
| WO | WO-2003/023018 A2 | 3/2003 |
| WO | WO-2003/023019 A1 | 3/2003 |
| WO | WO-2003/025167 A2 | 3/2003 |
| WO | WO-2003/029402 A2 | 4/2003 |
| WO | 03/039459 A2 | 5/2003 |
| WO | WO-2003/040336 A2 | 5/2003 |
| WO | WO-2003/042405 A2 | 5/2003 |
| WO | WO-2003/046161 A2 | 6/2003 |
| WO | WO-2003/055989 A2 | 7/2003 |
| WO | WO-2003/061685 A1 | 7/2003 |
| WO | WO-2003/061686 A1 | 7/2003 |
| WO | WO-2003/068961 A2 | 8/2003 |
| WO | WO-2003/072064 A2 | 9/2003 |
| WO | WO-2003/078609 A1 | 9/2003 |
| WO | WO-2003/078967 A2 | 9/2003 |
| WO | WO-2003/080816 A2 | 10/2003 |
| WO | WO-2003/082145 A2 | 10/2003 |
| WO | WO-2003/085099 A2 | 10/2003 |
| WO | WO-2003/089631 A1 | 10/2003 |
| WO | WO-2003/091398 A2 | 11/2003 |
| WO | WO-2003/095631 A1 | 11/2003 |
| WO | 03/105663 A2 | 12/2003 |
| WO | WO-2004/001697 A1 | 12/2003 |
| WO | WO-2004/012226 A2 | 2/2004 |
| WO | WO-2004/016779 A1 | 2/2004 |
| WO | WO-2004/018526 A1 | 3/2004 |
| WO | WO-2004/018655 A2 | 3/2004 |
| WO | WO-2004/026115 A2 | 4/2004 |
| WO | WO-2004/029231 A1 | 4/2004 |
| WO | WO-2004/042023 A2 | 5/2004 |
| WO | WO-2004/042033 A2 | 5/2004 |
| WO | WO-2004/042040 A1 | 5/2004 |
| WO | WO-2004/044127 A2 | 5/2004 |
| WO | WO-2004/044158 A2 | 5/2004 |
| WO | WO-2004/046304 A1 | 6/2004 |
| WO | WO-2004/050826 A2 | 6/2004 |
| WO | WO-2004/053096 A2 | 6/2004 |
| WO | WO-2004/055155 A2 | 7/2004 |
| WO | WO-2004/056186 A1 | 7/2004 |
| WO | WO-2004/065616 A2 | 8/2004 |
| WO | WO-2004/069172 A2 | 8/2004 |
| WO | WO-2004/070013 A2 | 8/2004 |
| WO | WO-2004/072264 A2 | 8/2004 |
| WO | WO-2004/073633 A2 | 9/2004 |
| WO | WO-2004/074464 A1 | 9/2004 |
| WO | WO-2004/076642 A2 | 9/2004 |
| WO | WO-2004/076653 A1 | 9/2004 |
| WO | 2004/090112 A2 | 10/2004 |
| WO | WO-2004/087870 A2 | 10/2004 |
| WO | WO-2004/094588 A2 | 11/2004 |
| WO | WO-2004/096975 A2 | 11/2004 |
| WO | WO-2004/104166 A2 | 12/2004 |
| WO | WO-2004/106499 A1 | 12/2004 |
| WO | WO-2004/113513 A2 | 12/2004 |
| WO | WO-2005/001033 A2 | 1/2005 |
| WO | WO-2005/001081 A1 | 1/2005 |
| WO | WO-2005/003320 A2 | 1/2005 |
| WO | WO-2005/007799 A1 | 1/2005 |
| WO | WO-2005/010172 A2 | 2/2005 |
| WO | WO-2005/011524 A1 | 2/2005 |
| WO | WO-2005/012480 A2 | 2/2005 |
| WO | WO-2005/012510 A1 | 2/2005 |
| WO | WO-2005/012512 A1 | 2/2005 |
| WO | WO-05014775 A2 | 2/2005 |
| WO | WO-2005/028433 A2 | 3/2005 |
| WO | WO-05044972 A2 | 5/2005 |
| WO | WO-2005/056747 A2 | 6/2005 |
| WO | WO-05051316 A2 | 6/2005 |
| WO | WO-2005/063303 A1 | 7/2005 |
| WO | WO-2005/075636 A1 | 8/2005 |

(56) References Cited

FOREIGN PATENT DOCUMENTS

| WO | 2005087915 A2 | 9/2005 |
|---|---|---|
| WO | 2005/104755 A2 | 11/2005 |
| WO | WO-2005/107760 A1 | 11/2005 |
| WO | WO-2006/009291 A1 | 1/2006 |
| WO | WO-2006/032075 A1 | 3/2006 |
| WO | WO-2006/032092 A1 | 3/2006 |
| WO | 2006/037022 A2 | 4/2006 |
| WO | WO-2006/108229 A1 | 10/2006 |
| WO | WO-2006/113881 A2 | 10/2006 |
| WO | WO-2006/121445 A2 | 11/2006 |
| WO | WO-06124021 A1 | 11/2006 |
| WO | WO-06129312 A2 | 12/2006 |
| WO | 2007/038572 A2 | 4/2007 |
| WO | 2007/059473 A2 | 5/2007 |
| WO | 2007/117765 A2 | 10/2007 |
| WO | WO-2007/115367 A1 | 10/2007 |
| WO | WO-2007/115368 A1 | 10/2007 |
| WO | 2007/136821 A1 | 11/2007 |
| WO | WO-2007/136760 A2 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A2 | 12/2007 |
| WO | WO-2008/006168 A1 | 1/2008 |
| WO | WO-2008/011664 A1 | 1/2008 |
| WO | WO-2008/017128 A1 | 2/2008 |
| WO | WO-2008/028241 A1 | 3/2008 |
| WO | WO-08040812 A1 | 4/2008 |
| WO | 2008/073635 A2 | 6/2008 |
| WO | 2008/109674 A2 | 9/2008 |
| WO | WO-2008/116261 A1 | 10/2008 |
| WO | WO-2008/149129 A1 | 12/2008 |
| WO | 2009/034186 A2 | 3/2009 |
| WO | WO-2009/026635 A1 | 3/2009 |
| WO | WO-09058146 A1 | 5/2009 |
| WO | WO-09080054 A1 | 7/2009 |
| WO | WO-09081408 A2 | 7/2009 |
| WO | WO-2009/140452 A2 | 11/2009 |
| WO | WO-09132457 A1 | 11/2009 |
| WO | WO-2009/144720 A1 | 12/2009 |
| WO | WO-10005527 A1 | 1/2010 |
| WO | WO-2010/019886 A1 | 2/2010 |
| WO | WO-10014253 A2 | 2/2010 |
| WO | WO-10019997 A1 | 2/2010 |
| WO | WO-2010/026575 A2 | 3/2010 |
| WO | WO-2010/026573 A1 | 3/2010 |
| WO | WO-2010/026574 A2 | 3/2010 |
| WO | 2010/036760 A1 | 4/2010 |
| WO | WO-2010/059487 A1 | 5/2010 |
| WO | WO-10061377 A2 | 6/2010 |
| WO | WO-10068710 A2 | 6/2010 |
| WO | WO-10071826 A2 | 6/2010 |
| WO | WO-10083385 A2 | 7/2010 |
| WO | WO-10111255 A1 | 9/2010 |
| WO | WO-10119036 A1 | 10/2010 |
| WO | WO-10123594 A2 | 10/2010 |
| WO | WO-2011/025445 A1 | 3/2011 |
| WO | 2011/098592 A1 | 8/2011 |
| WO | 2011/130617 A2 | 10/2011 |
| WO | WO-2011/132087 A1 | 10/2011 |
| WO | WO-2011/147967 A1 | 12/2011 |
| WO | WO-2012/072924 A1 | 6/2012 |
| WO | WO-2012/127320 A1 | 9/2012 |
| WO | WO-2012/138968 A1 | 10/2012 |
| WO | WO-2012/140519 A2 | 10/2012 |
| WO | 2012/171026 A2 | 12/2012 |
| WO | 2012/171030 A2 | 12/2012 |
| WO | 2013/085682 A1 | 6/2013 |
| WO | WO-2013/110651 A1 | 8/2013 |
| WO | WO-2014/037862 A1 | 3/2014 |
| WO | WO-2014/037863 A1 | 3/2014 |
| WO | WO-2014/068508 A2 | 5/2014 |
| WO | WO-2014/128634 A1 | 8/2014 |
| WO | WO-2014/128306 A1 | 8/2014 |
| WO | WO-2014/131846 A1 | 9/2014 |
| WO | WO-2014/141111 A1 | 9/2014 |
| WO | WO-2015/004609 A2 | 1/2015 |
| WO | 2015/059714 A1 | 4/2015 |
| WO | 2015/069943 A1 | 5/2015 |
| WO | 2015/073913 A1 | 5/2015 |
| WO | 2015/118148 A1 | 8/2015 |
| WO | 2015/118149 A1 | 8/2015 |
| WO | WO-2015/131143 A1 | 9/2015 |
| WO | 2016/130940 A1 | 8/2016 |
| WO | 2017/072201 A2 | 5/2017 |
| WO | 2017/158611 A1 | 9/2017 |
| WO | 2017/207822 A1 | 12/2017 |
| WO | 2018/183426 A1 | 10/2018 |
| WO | 2019/155032 A1 | 8/2019 |
| WO | 2019/238919 A1 | 12/2019 |
| WO | 2020/020569 A1 | 1/2020 |
| WO | 2020/079274 A1 | 4/2020 |

OTHER PUBLICATIONS

International Search Report and Written Opinion, PCT/US2016/040855, dated Dec. 21, 2016.

Invitation to Pay Additional Fees and the Partial International Search, PCT/US2016/040855, dated Sep. 28, 2016.

Jin et al., "Ligand-Independent Activation of Vascular Endothelial Growth Factor Receptor 2 by Fluid Shear Stress Regulates Activation of Endothelial Nitric Oxide Synthase", Circulation Research, vol. 93, No. 4, pp. 354-363, Aug. 22, 2003.

Martin et al., "The Role of Bioreactors in Tissue Engineering", Trend in Biotechnology, vol. 22, No. 2, pp. 80-86, Feb. 1, 2004.

Abumiya et al., "Shear Stress Induces Expression of Vascular Endothelial Growth Factor Receptor Flk-1/KDR Through the CT-Rich Sp1 Binding Site," Arteriosclerosis, Thrombosis, and Vascular Biology, vol. 22, pp. 907-913, Jun. 2002.

Akiyama et al., "Ultrathin Poly(N-isopropylacrylamide) Grafted Layer on Polystyrene Surfaces for Cell Adhesion/Detachment Control," Langmuir, vol. 20, No. 13, pp. 5506-5511, May 26, 2004.

Akram et al., "Mesenchymal Stem Cells Promote Alveolar Epithelial Cell Wound Repair in vitro through Distinct Migratory and Paracrine Mechanisms," Respiratory Research, vol. 14, No. 9, pp. 1-16, 2013.

Alenazi et al., "Modified Polyether-sulfone Membrane: a Mini Review," Designed Monomers And Polymers, vol. 20, No. 1, pp. 532-546, 2017.

Anamelechi et al., "Streptavidin Binding and Endothelial Cell Adhesion to Biotinylated Fibronectin," Langmuir, vol. 23, No. 25, pp. 12583-12588, Dec. 4, 2007.

Azar et al., "Heart Rates of Male and Female Sprague—Dawley and Spontaneously Hypertensive Rats Housed Singly or in Groups," Journal of the American Association for Laboratory Animal Science, vol. 50, No. 2, pp. 175-184, Mar. 2011.

Bai et al., "Expansion of Primitive Human Hematopoietic Stem Cells by Culture in a Zwitterionic Hydrogel," Nature Medicine, vol. 25, pp. 1566-1575, Oct. 2019.

Barker et al., "CD34+ Cell Content of 126 341 Cord Blood Units in the US Inventory: Implications for Transplantation and Banking," Blood Advances, vol. 3, No. 8, pp. 1267-1271, Apr. 23, 2019.

Beacher-Allan et al., "CD4+CD25high Regulatory Cells in Human Peripheral Blood," The Journal of Immunology, vol 167, pp. 1245-1253, 2001.

Boitano et al., "Aryl Hydrocarbon Receptor Antagonists Promote the Expansion of Human Hematopoietic Stem Dells," Science, vol. 329, No. 5997, pp. 1345-1348, Sep. 10, 2010. Corrected May 6, 2011.

Brunstein et al., "Infusion of ex vivo Expanded T Regulatory Cells in Adults Transplanted with Umbilical Cord Blood Safety Profile and Detection Kinetics," Blood, vol. 117, No. 3, pp. 1061-1070, Jan. 20, 2011.

Bryce et al., "In vitro Micronucleus Assay Scored by Flow Cytometry Provides a Comprehensive Evaluation of Cytogenetic Damage and Cytotoxicity," Mutation Research, vol. 630, pp. 78-91, Mar. 19, 2007.

(56) References Cited

OTHER PUBLICATIONS

Bryce et al., "Interlaboratory Evaluation of a Flow Cytometric, High Content in vitro Micronucleus Assay," Mutation Research, vol. 650, pp. 181-195, Jan. 7, 2008.
Camacho Villa et al., "CD133+CD34+ and CD133+CD38+ Blood Progenitor Cells as Predictors of Platelet Engraftment in Patients Undergoing Autologous Peripheral Blood Stem Cell Transplantation," Transfusion and Apheresis Science, vol. 46, pp. 239-244, 2012.
Cano et al., "Immobilization of endo-1,4-βxylanase on Polysulfone Acrylate Membranes: Synthesis and Characterization," Journal of Membrane Science, vol. 280, pp. 383-388, Feb. 28, 2006.
Carvell and Dowd, "On-line Measurements and Control of Viable Cell Density in Cell Culture Manufacturing Processes Using Radio Frequency Impedance," Cytotechnology, vol. 50, pp. 35-48, 2006.
Carvell et al., "Monitoring Live Biomass in Disposable Bioreactors," BioProcess International, vol. 14, No. 3, pp. 10-48, Mar. 2016.
Cuchiara et al., "Covalent Immobilization of SCF and SDF1α for in vitro Culture of Hematopoietic Progenitor Cells," Acta Biomaterials, vol. 9, No. 12, pp. 9258-9269, Dec. 2013.
Da Silva et al., "Smart Thermoresponsive Coatings and Surfaces for Tissue Engineering: Switching Cell-Material Boundaries," Trends in Biotechnology, vol. 15, No. 12, pp. 577-583, 2007.
Hao et al., "A Functional Comparison of CD34+ CD38—Cells in Cord Blood and Bone Marrow," Blood, vol. 86, No. 10, pp. 3745-3753, Nov. 15, 1995.
Harimoto et al., "Novel Approach for Achieving Double-Layered Cell Sheets Co-Culture: Overiaying Endothelial Cell Sheets onto Monolayer Hepatocytes Utilizing Temperature-Responsive Culture Dishes," Journal of Biomedical Materia Research, vol. 62, pp. 464-470, 2002.
Högstedt et al., "Frequency and Size Distribution of Micronuclei in Lymphocytes Stimulated with Phytohemagglutinin and Pokeweed Mitogen in Workers Exposed to Piperazine," Hereditas, vol. 109, pp. 139-142, 1988.
Horwitz et al., "Phase I/II Study of Stem-Cell Transplantation Using a Single Cord Blood Unit Expanded Ex Vivo with Nicotinamide," Journal of Clinical Oncology, vol. 37, No. 5, pp. 367-376, Dec. 4, 2018.
Itkin and Lapidot, "SDF-1 Keeps HSC Quiescent at Home," Blood, vol. 117, No. 2, pp. 373-374, Jan. 13, 2011.
Jang et al., "Syndecan-4 Proteoliposomes Enhance Fibroblast Growth Factor-2 (FGF-2)-Induced Proliferation, Migration, and Neovascularization of Ischemic Muscle," PNAS, vol. 109, No. 5, pp. 1679-1684, Jan. 31, 2012.
Johansson et al., "Pancreatic Islet Survival and Engraftment Is Promoted by Culture on Functionalized Spider Silk Matrices," PLoS ONE, pp. 1-21, Jun. 19, 2015.
Klein et al., "Affinity Membranes Prepared from Hydrophilic Coatings on Microporous Polysulfone Hollow Fibers," Journal of Membrane Science, vol. 90, pp. 69-80, 1994.
Koestenbauer et al., "Protocols for Hematopoietic Stem Cell Expansion from Umbilical Cord Blood," Cell Transplantation, vol. 18, pp. 1059-1068, May 6, 2009.
Koller et al., "Clinical-scale Human Umbilical Cord Blood Cell Expansion in a Novel Automated Perfusion Culture System," Bone Marrow Transplantation, vol. 21, pp. 653-663, 1998.
Lang et al., "Generation of Hematopoietic Humanized Mice in the Newborn BALB/C-Rag2null Il2rynull Mouse Model: A Multivariable Optimization Approach," Clinical Immunology, vol. 140, pp. 102-116, Apr. 14, 2011.
Lataillade et al., "Chemokine SDF-1 Enhances Circulating CD341 Cell Proliferation in Synergy with Cytokines: Possible Role in Progenitor Survival," Blood, vol. 95, No. 3, pp. 756-768, Feb. 1, 2000.
Lee et al., "Long-Term Outcomes Following CD19 Car T Cell Therapy for B-ALL Are Superior in Patients Receiving a Fludarabine/Cyclophosphamide Preparative Regimen and Post-CAR Hematopoietic Stem Cell Transplantation," Blood, vol. 128, No. 22, Ab. 218, Dec. 2, 2016.
Li et al., "Heparin-induced Conformation Changes of Fibronectin within the Extracellular Matrix Promote hMSC Osteogenic Differentiation," Biomaterials Science, vol. 3, pp. 73-84, 2015.
Malin et al., "Noninvasive Prediction of Glucose by Near-Infrared Diffuse Reflectance Spectroscopy," Clinical Chemistry, vol. 45, No. 9, 1651-1658, 1999.
Marek-Trzonkowska et al., "Administration of CD4+ CD25high CD127- Regulatory T Cells Preserves 0-Cell Function in Type 1 Diabetes in Children," Diabetes Care, vol. 35, No. 9, pp. 1817-1820, Sep. 2012.
Murugappan et al., "Human Hematopoietic Progenitor Cells Grow Faster under Rotational Laminar Flows," Biotechnology Progress - Cell Culture & Tissue Engineering, Online, Apr. 22, 2010.
Nelson et al., "Emergent Patterns of Growth Controlled by Multicellular Form and Mechanics," PNAS, vol. 102, No. 33, pp. 11594-11599, Aug. 16, 2005.
Nicolette et al., "In Vitro Micronucleus Screening of Pharmaceutical Candidates by Flow Cytometry in Chinese Hamster V79 Cells," Environmental and Molecular Mutagenesis, vol. 52, pp. 355-362, Oct. 20, 2010.
Nugent et al., "Adventitial Endothelial Implants Reduce Matrix Metalloproteinase-2 Expression and Increase Luminal Diameter in Porcine Arteriovenous Grafts," Journal of Vascular Surgery, vol. 46, No. 3, pp. 548-556.e2, Sep. 2007.
Dkano et al., "Mechanism of Cell Detachment from Temperature-Modulated, Hydrophilic-Hydrophobic Polymer Surfaces," Biomaterials, vol. 16, No. 4, pp. 297-303, 1995.
Putnam et al., "Expansion of Human Regulatory T-Cells from Patients with Type 1 Diabetes," Diabetes, vol. 58, pp. 352-662, Mar. 2009.
Rahmahwati et al., "The Synthesis of Polyethersulfone (PES) Derivatives for the Immobilization of Lipase Enzyme," Key Engineering Materials, vol. 811, pp. 14-21, Jul. 8, 2019.
Rodrigues et al., "Stem Cell Cultivation in Bioreactors," Biotechnology Advances, vol. 29, pp. 815-829, Jun. 25, 2011.
Ronco et al., "Blood and Dialysate Flow Distributions in Hollow-Fiber Hemodialyzers Analyzed by Computerized Helical Scanning Technique," Journal of the American Society of Nephrology, vol. 13, pp. S53-S61, 2002.
Ryu and Gomelsky, "Near-infrared Light Responsive Synthetic c-di-GMP Module for Optogenetic Applications," ACS Synthetic Biology, vol. 3, pp. 802-810, Jan. 28, 2014.
Shimizu et al., "Fabrication of Pulsatile Cardiac Tissue Grafts Using a Novel 3-Dimensional Cell Sheet Manipulation Technique and Temperature-Responsive Cell Culture Surfaces," Circulation Research, vol. 90, e40-e48, pp. 1-9, Feb. 22, 2002.
Smith et al., "Expansion of Neutrophil Precursors and Progenitors in Suspension Cultures of CD34+ Cells Enriched from Human Bone Marrow," Experimental Hematology, vol. 21, pp. 870-877, 1993.
Streltsova et al., "Recurrent Stimulation of Natural Killer Cell Clones with K562 Expressing Membrane-Bound Interleukin-21 Affects Their Phenotype, Interferon-γProduction, and Lifespan," International Journal of Molecular Sciences, vol. 20, No. 443, pp. 1-18, 2019.
Takezawa et al., "Cell Culture on a Thermo-responsive Polymer Surface," Nature, Bio/Technology, vol. 8, pp. 854-856, Sep. 1990.
Tiziani et al., "Metabolomic Profiling of Drug Response in Acute Myeloid Leukaemia Cell lines," PLoS One, vol. 4, Issue 1, e4251, Jan. 22, 2009.
Chang et al., "Membrane Bioreactors: Present and Prospects", Advances in Biochemical Engineering, 1991, pp. 27-64, vol. 44.
Chang, Ho Nam, "Membrane Bioreactors: Engineering Aspects", Biotech. Adv., 1987, pp. 129-145, vol. 5.
Edgington, Stephen M., "New Horizons for Stem-Cell Bioreactors", Biotechnology, Oct. 1992, pp. 1099-1106, vol. 10.
Gastens et al., "Good Manufacturing Practice-Compliant Expansion of Marrow-Derived Stem and Progenitor Cells for Cell Therapy", Cell Transplantation, 2007, pp. 685-696, vol. 16.
Gramer et al., "Screening Tool for Hollow-Fiber Bioreactor Process Development", Biotechnol. Prog., 1998, pp. 203-209, vol. 14.

(56) References Cited

OTHER PUBLICATIONS

Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.
Infanger et al., "Simulated weightlessness changes the cytoskeleton and extracellular matrix proteins in papillary thyroid carcinoma cells", Cell and Tissue Research, 2006, 324(2): 267-277.
Jones et al., "Genetic stability of bone marrow-derived human mesenchymal stromal cells in the Quantum System", Cytotherapy, 2013; 15: 1323-1339.
Liu et al., "Ex vivo Expansion of Hematopoietic Stem Cells Derived from Umbilical Cord Blood in Rotating Wall Vessel", Journal of Biotechnology, 2006, 124:592-601.
Nankervis et al., "Shear Stress Conditions in the Quantum Cell Expansion System", Poster Session—Termis Am Annual Conference 2013, Nov. 12, 2013.
Nguyen et al., "Quantum® Cell Expansion System: Automated Expansion of Human Mesenchymal Stem Cells from Precultured Cells Using the Quantum Cell Expansion System", Terumo BCT, Inc., 2012.
Nielsen, Lars Keld, "Bioreactors for Hematopoietic Cell Culture", Annu. Rev. Biomed. Eng., 1999, vol. 1, pp. 129-152.
Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.
Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 182-193.
Garlie et al., "T Cells Coactivated with Immobilized Anti-CD3 and Anti-CD28 as Potential Immunotherapy for Cancer," Journal of Immunotherapy, vol. 22, No. 4, pp. 336-345, 1999.
GE Healthcare UK Limited, "The Effect of Rocking Rate and Angle on T Cell Cultures Grown in Xuri(TM) Cell Expansion Systems," Cell therapy bioreactor systems, Application note 29-1166-55 AA, pp. 1-4, www.gelifesciences.com/xuri, Aug. 2014.
Ueda et al., "Interaction of Natural Killer Cells with Neutrophils Exerts a Significant Antitumor Immunity in Hematopoietic Stem Cell Transplantation Recipients," Cancer Medicine, vol. 5, No. 1, pp. 49-60, 2015.
Urbich et al., "Fluid Shear Stress-Induced Transcriptional Activation of the Vascular Endothelial Growth Factor Receptor-2 Gene Requires Sp1-Dependent DNA Binding," FEBS Letters, 535, pp. 87-93, 2003.
Von Laer, D., "Loss of CD38 Antigen on CD34 CD38 Cells during Short-Term Culture," Leukemia, Correspondence, pp. 947-948, 1999.
Wagner et al., "Phase I/II Trial of StemRegenin-1 Expanded Umbilical Cord Blood Hematopoietic Stem Cells Supports Testing as a Stand-Alone Graft," Cell Stem Cell, vol. 18, pp. 143-155, Jan. 7, 2016.
Weaver et al., "An Analysis of Engraftment Kinetics as a Function of the CD34 Content of Peripheral Blood Progenitor Cell Collections in 692 Patients After the Adminstration of Myeloablative Chemotherapy," Blood, vol. 86, No. 10, pp. 3961-3969, Nov. 15, 1995.
Yang et al., "Suspension Culture of Mammalian Cells Using Thermosensitive Microcarrier that Allows Cell Detachment Without Proteolytic Enzyme Treatment," Cell Transplantation, vol. 19, pp. 1123-1132, 2010.
Yi et al., "A Readily Modified Polyethersulfone with Amino-Substituted Groups: Its Amphiphilic Copolymer Synthesis and Membrane Application," Polymer, vol. 53, pp. 350-358, Dec. 2, 2011.
Zheng et al., "Differential Effects of Cyclic and Static Stretch on Coronary Microvascular Endothelial Cell Receptors and Vasculogenic/Angiogenic Responses," American Journal of Physiology—Heart and Circulatory Physiology, vol. 295, H794-H800, Aug. 2008.
Aronowski, et al., An Alternative Method for the Quantitation of Neuronal Damage after Experimental Middle Cerebral Artery Occlusion in Rats: Analysis of Behavioral Deficit. Journal Of Cerebral Blood Flow and Metabolism. 1996,16:705-713.
Bazarian, et al., Long-Term Neurologic Outcomes after Traumatic Brain Injury. The Journal of Head Trauma Rehabilitation. 2009, 24(6):439-451.
Blum et al., A Mitogen-Activated Protein Kinase Cascade in the Ca1/Ca2 Subfield of the Dorsal Hippocampus Is Essential for Long-Term Spatial Memory The Journal of Neuroscience May 1, 1999,19(9):3535-3544.
Creed et al., Concussive Brain Trauma in the Mouse Results in Acute Cognitive Deficits and Sustained Impairment of Axonal Function. Journal of Neurotrauma Apr. 2011, 28:547-563.
Dash et al., Injection of the cAMP-Responsive Element into the Nucleus of Aplysia Sensory Neurons Blocks Long-Term Facilitation Nature. Jun. 21, 1990, 345:718-721.
Dash et al., Intrahippocampal Wortmannin Infusion Enhances Long-Term Spatial and Contextual Memories. Learning & Memory. 2002, 9:167-177.
Dash et al., Involvement of the Glycogen Synthase Kinase-3 Signaling Pathway in TBI Pathology and Neurocognitive Outcome. PLoS One. Sep. 2011, 6(9):e24648:1-11.
Dash et al., Sulforaphane Improves Cognitive Function Administered Following Traumatic Brain Injury. Neuroscience Letters. 2009, 460:103-107.
Dash et al., Valproate Administered after Traumatic Brain Injury Provides Neuroprotection and Improves Cognitive Function in Rats PLoS One. Jun. 2010, 5(6):e11383:1-13.
Dejana et al., Interendothelial Junctions and their Role in the Control of Angiogenesis, Vascular Permeability and Leukocyte Transmigration. Thrombosis and Haemostasis. 2001, 86:308-315.
Dejana et al., The Control of Vascular Integrity by Endothelial Cell Junctions: Molecular Basis and Pathological mplications. Developmental Cell. Feb. 17, 2009, 16:209-221.
Dejana et al., The Role of Adherens Junctions and VE-cadherin in the Control of Vascular Permeability. Journal of Cell Science. May 2008, 121(13):2115-2122.
Dixon et al., A Controlled Cortical Impact Model of Traumatic Brain Injury in the Rat. Journal of Neuroscience Methods. 1991, 39:253-262.
Fischbach et al, Cell-Based Therapeutics: The Next Pillar of Medicine. Science Translational Medicine. Apr. 3, 2013, 5 (179):1-6.
Goldring et al., Assessing the Safety of Stem Cell Therapeutics. Cell Stem Cell. Jun. 3, 2011, 8:618-628.
Hall et al., Spatial and Temporal Characteristics of Neurodegeneration after Controlled Cortical Impact in Mice: More than a Focal Brain Injury. Journal of Neurotrauma. 2005, 22(2):252-265.
Hamm et al., Cognitive Deficits Following Traumatic Brain Injury Produced by Controlled Cortical Impact. Journal of Neurotrauma. 1992, 9(1):11-20.
Lampugnani et al., Endothelial Cell-To-Cell Junctions. Structural Characteristics and Functional Role in the Regulation of Vascular Permeability and Leukocyte Extravasation. Bailliere's Clinical Haematology. Sep. 1993, 6 (3):539-558.
Lee et al., Allogeneic Human Mesenchymal Stem Cells for Treatment of E. Coli Endotoxin-Induced Acute Lung Injury in the Ex Vivo Perfused Human Lung. PNAS Sep. 22, 2009, 106(38):16357-16362.
Markgraf et al., Injury Severity and Sensitivity to Treatment After Controlled Cortical Impact in Rats. Journal of Neurotrauma. 2001, 18(2):175-188.
Matthay et al, Therapeutic Potential of Mesenchymal Stem Cells for Severe Acute Lung Injury. Chest. Oct. 2010, 138(4):965-972.
Menge et al, Mesenchymal Stem Cells Regulate Blood-Brain Barrier Integrity through TIMP3 Release After Traumatic Brain Injury. Science Translational Medicine Nov. 21, 2012, 4(161):1-11.
Onyszchuk et al., Post-Acute Pathological Changes in the Thalamus and Internal Capsule in Aged Mice Following Controlled Cortical

(56) References Cited

OTHER PUBLICATIONS

Impact Injury: A Magnetic Resonance Imaging, Iron Histochemical, and Glial Immunohistochemical Study. Neuroscience Letters. 2009, 452:204-208.
Pati et al., Bone Marrow Derived Mesenchymal Stem Cells Inhibit Inflammation and Preserve Vascular Endothelial Integrity in the Lungs after Hemorrhagic Shock. PLoS One. Sep. 2011, 6(9):e25171:1-14.
Pati et al., Human Mesenchymal Stem Cells Inhibit Vascular Permeability by Modulating Vascular Endothelial Cadherin/Beta-Catenin Signaling Stem Cells and Development. 2011, 20(1):89-101.
Abumiya, et al. at National Cardiovascular Center Research Institute in Japan, suggest that subjecting human umbilical vein endothelial cells (HUVECs) to laminar shear stress for a period of 8 hours increased the relative expression of VEGFR-2 mRNA (Ateriosclerosis, Thrombosis, and Vascular Biology, 2002).
Afzali B, Edozie FC, Fazekasova H, Scotta C, Mitchell PJ, Canavan JB, Kordasti SY, Chana PS, Ellis R, Lord GM, John S, Hilton R, Lechler RI, Lombardi G. Comparison of regulatory T cells in hemodialysis patients and healthy controls: implications for cell therapy in transplantation. Clin J Am Soc Nephrol. 2013;8(8):1396-405.
Akram, Khondoker M., et al. "Mesenchymal stem cells promote alveolar epithelial cell wound repair in vitro through distinct migratory and paracrine mechanisms." Respiratory research 14.1 (2013): 1-16, reference not provided.
Almeida L, Lochner M, Berod L, Sparwasser T. Metabolic pathways in T cell activation and lineage differentiation. Semin Immunol. 2016;28(5):514-524.
Amy Putnam, Todd M. Brusko, Michael R. Lee, Weihong Liu, Gregory L. Szot, Taumoha Ghosh, Mark A. Atkinson, and Jeffrey A. Bluestone. Expansion of human regulatory T-Cells from patients with Type 1 Diabetes. Diabetes, 58: 652-662, 2009.
Anurathapan et al., "Engineered T cells for cancer treatment," Cytotherapy, vol. 16, pp. 713-733, 2014.
Arrigoni, Chiara, et al. "Rotating versus perfusion bioreactor for the culture of engineered vascular constructs based on hyaluronic acid." Biotechnology and bioengineering 100.5 (2008): 988-997.
Baecher-Allan, Clare, et al. "CD4+ CD25high regulatory cells in human peripheral blood." The Journal of Immunology 167.3 (2001): 1245-1253.
Bai/Delaney (Nohla Therapeutics) showed that expanding Cord Blood-derived CD34+CD38-CD45RA- HSPCs in a biodegradable zwitterionic hydrogel with a rNotch ligand cocktail for 24 days mitigated HSPC differentiation and promoted self-renewal of lymphoid and myeloid cell phenotypes in an NSG mouse model (Nature Medicine, 2019).
Ballas CB, Zielske SP, Gerson SL (2002) Adult bone marrow stem cells for cell and gene therapies: implications for greater use. J Cell Biochem Suppl 38: 20-28.
Ballke C, Gran E, Baekkevold ES, Jahnsen FL. Characterization of Regulatory T-Cell Markers in CD4+ T Cells of the Upper Airway Mucosa. PLoS One. 2016;11(2):e0148826.
Baraniak PR, McDevitt TC (2010) Stem cell paracrine actions and tissue regeneration. Regen Med 5(1): 121-143.
Barckhausen C, Rice B, Balla S, et al. (2016) GMP-Compliant Expansion of Clinical-Grade Human Mesenchymal Stromal/Stem Cells Using a Closed Hollow Fiber Bioreactor. Methods Mol Biol 1416:389-412.
Bending D, Pesenacker AM, Ursu S, Wu Q, Lorn H, Thirugnanabalan B, Wedderburn LR. Hypomethylation at the regulatory T cell-specific demethylated region in CD25hi T cells is decoupled from FOXP3 expression at the inflamed site in childhood arthritis. J Immunol. 2014;193(6):2699-708.
Berendse M, Grounds MD, Lloyd CM (2003) Myoblast structure affects subsequent skeletal myotube morphology and sarcomere assembly. Exp Cell Res 291(2): 435-450.
Bernard, A., Payton, Mar. 1995. "Fermentation and Growth of *Escherichia coli* for Optimal Protein Production".
Berney SM, Schaan T, Wolf RE, van der Heyde H, Atkinson TP. CD2 (OKT 11) augments CD3-mediated intracellular signaling events in human T lymphocytes. J Investig Med. 2000;48(2):102-9.
Bioheart Clinical Trial Clinica 1302 Apr. 18, 2008.
Blache C, Chauvin JM, Marie-Cardine A, Contentin N, Pommier P, Dedreux I, Francois S, Jacquot S, Bastit D, Boyer 0. Reduced frequency of regulatory T cells in peripheral blood stem cell compared to bone marrow transplantations. Biol Blood Marrow Transplant. 2010;16(3):430-4.
Bluestone et al. Type 1 diabetes immunotherapy using polyclonal regulatory T cells. Science Translational Medicine 7(315):1-34, 2015.
Bluestone JA, Tang Q. Treg cells-the next frontier of cell therapy. Science. 2018;362(6411):154-155.
Bojun Li et al. Heparin-induced conformation changes of fibronectin within the extracellular matrix promote hMSC osteogenic differentiation. Biomaterials Science 3: 73-84, 2015.
Boquest AC, Shahdadfar A, Brinchmann JE, Collas P. Isolation of Stromal Stem Cells from Human Adipose Tissue. Methods Mol Biol. 2006;325:35-46. doi: 10.1385/1-59745-005-7:35. PMID: 16761717.
Borden, M. and Longo, M., "Dissolution Behavior of Lipid Monolayer-Coated, Air-Filled Microbubbles: Effect of Lipid Hydrophobic Chain Length," Langmuir, vol. 18, pp. 9225-9233, 2002.
Bourke, Sharon L., and Joachim Kohn. "Polymers derived from the amino acid L-tyrosine: polycarbonates, polyarylates and copolymers with poly (ethylene glycol)." Advanced drug delivery reviews 55.4 (2003): 447-466.
Brand, K. and Hermfisse, U., "Aerobic Glycolysis by Proliferating Cells: a Protective Strategy against Reactive Oxygen Species," The FASEB Journal, vol. 11, pp. 388-395, Apr. 1997.
Brentjens et al., "CD19-Targeted T Cells Rapidly Induce Molecular Remission in Adults with Chemotherapy-Refractory Acute Lympohblastic Leukemia," Science Translational Medicine, vol. 5, Issue 177, pp. 1-9, Mar. 20, 2013.
Brentjens et al., "Safety and Persistance of Adoptively Transferred Autologous CD19-Target T Cells in Patients with Relapsed or Chemotherapy Refractory B-Cell Leukemias," Blood, vol. 118, No. 18, pp. 4817-4828, Nov. 3, 2011.
C. H. Weaver, et al. An Analysis of Engraftment Kinetics as a function of the CD34 Content of the Peripheral Blood Progenitor Cell Collections in 692 Patients After the Administration of Myeloblative Chemotherapy. Blood 86(10): 3691-3969, 1995.
Carswell, K. and Papoutsakis, E. "Culture of Human T Cells in Stirred Bioreactors for Cellular Immunotherapy Applications: Shear, Proliferation, and the IL-2 Receptor," Biotechnology and Bioengineering, vol. 68, No. 3, pp. 329-338, May 5, 2000.
Celeste Nelson et al. in Christopher Chen's Lab demonstrated, in separate experiments, that curved surfaces with a radius of curvature (200 ?m) that is greater than the cell diameter and surfaces that have undulating special patterning (depressions) increase the patterned growth of ECs [PNAS 102(33): 11594-11599, 2005].
Chapman NM, Chi H. mTOR signaling, Tregs and immune modulation. Immunotherapy. 2014;6(12):1295-311.
Chaudhry A, Samstein RM, Treuting P, Liang Y, Pils MC, Heinrich JM, Jack RS, Wunderlich FT, Bruning JC, Muller W, Rudensky AY. Interleukin-10 signaling in regulatory T cells is required for suppression of Th17 cell-mediated inflammation. Immunity. 2011 ;34(4):566-78.
Chen, C. and Broden, M., "The Role of Poly(theylene glycol) Brush Architecture in Complement Activation on Targeted Microbubble Surfaces," Biomaterials, vol. 32, No. 27, pp. 6579-6587, Jun. 17, 2011.
Choi W, Kwon SJ, Jin HJ, et al. (2017) Optimization of culture conditions for rapid clinical-scale expansion of human umbilical cord blood-derived mesenchymal stem cells. Clin Transl Med 6(1): 38.
Chullikana A, Majumdar AS, Gottipamula S, et al. (2015) Randomized, double-blind, phase I/II study of intravenous allogeneic mesenchymal stromal cells in acute myocardial infarction. Cytotherapy 17(3): 250-261.

(56) References Cited

OTHER PUBLICATIONS

Coeshott C, Vang B, Jones M, Nankervis B. Large-scale expansion and characterization of CD3(+) T-cells in the Quantum((R)) Cell Expansion System. J Transl Med. 2019;17(1):258.
Coombes JL, Robinson NJ, Maloy KJ, Uhlig HH, Powrie F. Regulatory T cells and intestinal homeostasis. Immunol Rev. 2005;204:184-94.
Coquillard C. mTOR Signaling in Regulatory T cell Differentiation and Expansion. SOJ Immunology. 2015;3(1):1-10.
Davila et al., "Efficacy and Toxicity Management of 19-28z Car T Cell Therapy in B cell Acute Lymphoblastic Leukemia," Science Translational Medicine, vol. 6, No. 224, pp. 1-10, Feb. 19, 2014.
Del Pino A, Ligero G, Lopez MB, et al. (2015) Morphology, cell viability, karyotype, expression of surface markers and plasticity of three primary cell line cultures before and after the cryostorage in LN2 and GN2. Cryobiology 70(1): 1-8.
Delaney, Colleen, et al. "Notch-mediated expansion of human cord blood progenitor cells capable of rapid myeloid reconstitution." Nature medicine 16.2 (2010): 232-236.
Ding, Zhongli, Guohua Chen, and Allan S. Hoffman. "Synthesis and purification of thermally sensitive oligomer? enzyme conjugates of poly (N-isopropylacrylamide)? trypsin." Bioconjugate chemistry 7.1 (1996): 121-125.
Dominici M, Le Blanc K, Mueller I, et al. (2006) Minimal criteria for defining multipotent mesenchymal stromal cells. The International Society for Cellular Therapy position statement. Cytotherapy 8(4): 315-317.
Durrani S, Konoplyannikov M, Ashraf M, Haider KH (2010) Skeletal myoblasts for cardiac repair. Regen Med 5(6): 919-932.
Esensten JH, Muller YD, Bluestone JA, Tang Q. Regulatory T-cell therapy for autoimmune and autoinflammatory diseases: The next frontier. J Allergy Clin Immunol. 2018;142(6):1710-1718.
Fakin R, Hamacher J, Gugger M, Gazdhar A, Moser H, Schmid RA. Prolonged amelioration of acute lung allograft rejection by sequential overexpression of human interleukin-10 and hepatocyte growth factor in rats. Exp Lung Res. 2011 ;37(9):555-62.
Fedorov et al., "PD-1—and CTLA-4-Based Inhibitory Chimeric Antigen Receptors (iCARs) Divert Off-Target Immunotherapy Responses," Science Translational Medicine, vol. 5, No. 215, pp. 1-12, Dec. 11, 2013.
Ferreira LMR, Muller YD, Bluestone JA, Tang Q. Next-generation regulatory T cell therapy. Nat Rev Drug Discov. 2019;18(10):749-769.
Fisk, Nicholas M., et al. "Can routine commercial cord blood banking be scientifically and ethically justified?." PLoS medicine 2.2 (2005): e44.
Forbes Jun. 23, 2014 article "Will this man cure cancer?".
Fowler DH. Rapamycin-resistant effector T-cell therapy. Immunol Rev. 2014;257(1):210-25.
Fraser H, Safinia N, Grageda N, Thirkell S, Lowe K, Fry LJ, Scotta C, Hope A, Fisher C, Hilton R, Game D, Harden P, Bushell A, Wood K, Lechler RI, Lombardi G. A Rapamycin-Based GMP-Compatible Process for the Isolation and Expansion of Regulatory T Cells for Clinical Trials. Mol Ther Methods Clin Dev. 2018;8:198-209.
Frauwirth KA, Riley JL, Harris MH, Parry RV, Rathmell JC, Plas DR, Elstrom RL, June CH, Thompson CB. The CD28 signaling pathway regulates glucose metabolism. Immunity. 2002;16(6):769-77.
Fuchs A, Gliwinski M, Grageda N, Spiering R, Abbas AK, Appel S, Bacchetta R, Battaglia M, Berglund D, Blazar B, Bluestone JA, Bornhauser M, Ten Brinke A, Brusko TM, Cools N, Cuturi MC, Geissler E, Giannoukakis N, Golab K, Hafler DA, van Ham SM, Hester J et al. Minimum Information about T Regulatory Cells: A Step toward Reproducibility and Standardization. Front Immunol. 2017;8:1844.
G0211: Study for Gamma Irradiation of Bioreactor Membranes, undated, author unknown, 3 pages.
Galgani M, De Rosa V, La Cava A, Matarese G. Role of Metabolism in the Immunobiology of Regulatory T Cells. J Immunol. 2016;197(7):2567-75.

Gedaly R, De Stefano F, Turcios L, Hill M, Hidalgo G, Mitov Ml, Alstott MC, Butterfield DA, Mitchell HC, Hart J, Al-Attar A, Jennings CD, Marti F. mTOR Inhibitor Everolimus in Regulatory T Cell Expansion for Clinical Application in Transplantation. Transplantation. 2019;103(4):705-715.
Gimble, Jeffrey M., Adam J. Katz, and Bruce A. Bunnell. "Adipose-derived stem cells for regenerative medicine." Circulation research 100.9 (2007): 1249-1260.
Gingras AC, Raught B, Sonenberg N. Regulation of translation initiation by FRAP/mTOR. Genes Dev. 2001;15(7):807-26.
Godin, Michel, et al. "Measuring the mass, density, and size of particles and cells using a suspended microchannel resonator." Applied physics letters 91.12 (2007): 123121.
Golab K, Leveson-Gower D, Wang XJ, Grzanka J, Marek-Trzonkowska N, Krzystyniak A, Millis JM, Trzonkowski P, Witkowski P. Challenges in cryopreservation of regulatory T cells (Tregs) for clinical therapeutic applications. Int Immunopharmacol. 2013;16(3):371-5.
Griesche, Nadine, et al. "A simple modification of the separation method reduces heterogeneity of adipose-derived stem cells." cells tissues organs 192.2 (2010): 106-115.
Gutcher I, Donkor MK, Ma Q, Rudensky AY, Flavell RA, Li MO. Autocrine transforming growth factor-beta1 promotes in vivo Th17 cell differentiation. Immunity. 2011 ;34(3):396-408.
Haack-Sorensen M, Follin B, Juhl M, et al. (2016) Culture expansion of adipose derived stromal cells. A closed automated Quantum Cell Expansion System compared with manual flask-based culture. J Transl Med 14(1): 319.
Hami et al., "GMP Production and Testing of Xcellerated T Cells for the Treatment of Patients with CLL," Cytotherapy, pp. 554-562, 2004.
He N, Fan W, Henriquez B, Yu RT, Atkins AR, Liddle C, Zheng Y, Downes M, Evans RM. Metabolic control of regulatory T cell (Treg) survival and function by Lkb1. Proc Natl Acad Sci USA. 2017;114(47):12542-12547.
He X, Landman S, Bauland SC, van den Dolder J, Koenen HJ, Joosten I. A TNFR2-Agonist Facilitates High Purity Expansion of Human Low Purity Treg Cells. PLoS One. 2016;11(5):e0156311.
Heskins, Michael, and James E. Guillet. "Solution properties of poly (N-isopropylacrylamide)." Journal of Macromolecular Science—Chemistry 2.8 (1968): 1441-1455.
Hill JA, Feuerer M, Tash K, Haxhinasto S, Perez J, Melamed R, Mathis D, Benoist C. Foxp3 transcription-factor-dependent and -independent regulation of the regulatory T cell transcriptional signature. Immunity. 2007;27(5):786-800.
Högstedt, Benkt, Anita Karlsson, and Anders Holmen. "Frequency and size distribution on micronuclei in lymphocytes stimulated with phytohemagglutinin and pokeweed mitrogen in workers exposed to piperazine." Hereditas 109 ((1988): 139-142.
Hollyman et al., "Manufacturing Validation of Biologicall Functional T Cells Targeted to CD19 Antigen for Autologous Adoptive Cell Therapy," J Immunother, vol. 32, No. 2, pp. 169-180, Feb.-Mar. 2009.
http://www.ucdenver.edU/academics/colleges/medicalschool/centers/cancercenter/Research/s haredresources/Animallmaging/smallanimalimaging/Pages/MRI.aspx.
ISCT Webinar "Volume Reduction technology for Large Scale Harvest or Post-thaw Manipulation of Cellular Therapeutics".
Iwashima, Shigejiro, et al. "Novel culture system of mesenchymal stromal cells from human subcutaneous adipose tissue." Stem cells and development 18.4 (2009): 533-544.
Jarocha D, Stangel-Wojcikiewicz K, Basta A, Majka M (2014) Efficient myoblast expansion for regenerative medicine use. Int J Mol Med 34(1): 83-91.
Jo CH, Lee YG, Shin WH, et al. (2014) Intra-articular injection of mesenchymal stem cells for the treatment of osteoarthritis of the knee: a proof-of-concept clinical trial. Stem Cells 32(5): 1254-1266.
John Carvell, et al. Monitoring Live Biomass in Disposable Bioreactors, BioProcess International 14(3)s, Mar. 2016.
John Nicolette, et al. (Abbott Laboratories). In Vitro Micronucleus Screening of Pharmaceutical Candidates by Flow Cyto9metry in Chinese Hamster V79 Cells, Environmental and Molecular Mutagenesis 00:000-000, 2010.

(56) References Cited

OTHER PUBLICATIONS

John P. Carvell and Jason E. Dowd. On-line measurements and control of viable cell density in cell culture manufacturing processes using radio frequency impedance. Cytotechnology 50: 35-48, 2006.
Johnson, Patrick A., et al. "Interplay of anionic charge, poly (ethylene glycol), and iodinated tyrosine incorporation within tyrosine-derived polycarbonates: Effects on vascular smooth muscle cell adhesion, proliferation, and motility." Journal of Biomedical Materials Research Part A: An Official Journal of The Society for Biomaterials, The Japanese Society for Biomaterials, and The Australian Society for Biomaterials and the Korean Society for Biomaterials 93.2 (2010): 505-514.
Johnston LC, Su X, Maguire-Zeiss K, Horovitz K, Ankoudinova I, Guschin D, Hadaczek P, Federoff HJ, Bankiewicz K, Forsayeth J. Human interleukin-10 gene transfer is protective in a rat model of Parkinson's disease. Mol Ther. 2008;16(8):1392-9.
Jones2016ISCT 2016 Poster 69.
Joy, Abraham, et al. "Control of surface chemistry, substrate stiffness, and cell function in a novel terpolymer methacrylate library." Langmuir 27.5 (2011): 1891-1899.
Kalamasz et al., "Optimization of Human T-Cell Expansion Ex Vivo Using Magnetic Beads Conjugated with Anti-CD3 and Anti-CD28 Antibodies," J Immunother, vol. 27, No. 5, pp. 405-418, Sep.-Oct. 2004.
Klapper et al., "Single-Pass, Closed-System Rapid Expansion of Lymphocyte Cultures for Adoptive Cell Therapy," Journal of Immunological Methods, 345, pp. 90-99, Apr. 21, 2009.
Korpanty et al., "Tageting Vascular Enothelium with Avidin Microbubbles," Ultrasound in Medicine and Biology, vol. 31, No. 9, pp. 1279-1283, May 24, 2005.
Krauss et al., "Signaling Takes a Breath—New Quantitative Perspectives on Bioenergetics and Signal Transduction," Immunity, vol. 15, pp. 497-502, Oct. 2001.
Kulikov, A. V., et al. "Application of multipotent mesenchymal stromal cells from human adipose tissue for compensation of neurological deficiency induced by 3-nitropropionic acid in rats." Bulletin of experimental biology and medicine 145.4 (2008): 514-519.
Kumar P, Marinelarena A, Raghunathan D, Ragothaman VK, Saini S, Bhattacharya P, Fan J, Epstein AL, Maker AV, Prabhakar BS. Critical role of 0X40 signaling in the TCR-independent phase of human and murine thymic Treg generation. Cell Mol Immunol. 2019;16(2):138-153.
Kwan, J. and Borden, M., "Lipid Monolayer Collapse and Microbubble Stability," Advances in Colloid and Interface Science, vols. 183-184, pp. 82-99, Aug. 21, 2012.
Lee et al., "Continued Antigen Stimulation Is Not Reguired During CD4+ T Cell Clonal Expansion," The Journal of Immunology, 168, pp. 1682-1689, 2002.
Levine, B., "T Lymphocyte Engineering ex vivo for Cancer and Infectious Disease," Expert Opinion on Biological Therapy, vol. 4, No. 4, pp. 475-489, 2008.
Lum et al., "Ultrasound Radiation Force Enables Targeted Deposition of Model Drug Carriers Loaded on Microbubbles," Journal of Controlled Release, 111, pp. 128-134, 2006.
M. R. Koller, et al. Clinical-scale human umbilical cord blood cell expansion in a novel automated perfusion culture system. Bone Marrow Transplantation 21:653-663, 1998.
Malone et al., "Characterization of Human Tumor-Infiltrating Lymphocytes Expanded in Hollow-Fiber Bioreactors for Immunotherapy of Cancer," Cancer Biotherapy & Radiopharmaceuticals, vol. 16, No. 5, pp. 381-390, 2001.
Mao AS, Mooney DJ (2015) Regenerative medicine: current therapies and future directions. Proc Natl Acad Sci USA 112(47): 14452-14459.
Maria Streltsova, Dean Lee (Nationwide Children's Hospital, OSU, Columbus, OH) et al. (Int'l Journal of Molecular Sciences, 2019).
Mathew et al. A Phase I Clinical Trials I with Ex Vivo Expanded Recipient Regulatory T cells in Living Donor Kidney Transplants. Nature, Scientific Reports 8:7428 (1-12), 2018.
Maynard CL, Harrington LE, Janowski KM, Oliver JR, Zindl CL, Rudensky AY, Weaver CT. Regulatory T cells expressing interleukin 10 develop from Foxp3+ and Foxp3- precursor cells in the absence of interleukin 10. Nat Immunol. 2007;8(9):931-41.
McKenna DH, Jr., Sumstad D, Kadidlo DM, et al. Optimization of cGMP purification and expansion of umbilical cord blood-derived T-regulatory cells in support of first-in-human clinical trials. Cytotherapy 2017;19:250-62.
McLimans W, Kinetics of Gas Diffusion in Mammalian Cell Culture Systems. Biotechnology and Bioengineering 1968; 10:725-740.
McMurtrey, Richard J. "Analytic models of oxygen and nutrient diffusion, metabolism dynamics, and architecture optimization in three-dimensional tissue constructs with applications and insights in cerebral organoids." Tissue Engineering Part C: Methods 22.3 (2016): 221-249.
Miska J, Lee-Chang C, Rashidi A, Muroski ME, Chang AL, Lopez-Rosas A, Zhang P, Panek WK, Cordero A, Han Y, Ahmed AU, Chandel NS, Lesniak Ms. HIF-1 alpha Is a Metabolic Switch between Glycolytic-Driven Migration and Oxidative Phosphorylation-Driven Immunosuppression of Tregs in Glioblastoma. Cell Rep. 2019;27(1):226-237 e4.
Miyara M, Yoshioka Y, Kitoh A, Shima T, Wing K, Niwa A, Parizot C, Taflin C, Heike T, Valeyre D, Mathian A, Nakahata T, Yamaguchi T, Nomura T, Ono M, Amoura Z, Gorochov G, Sakaguchi S. Functional delineation and differentiation dynamics of human CD4+ T cells expressing the FoxP3 transcription factor. Immunity. 2009;30(6):899-911.
Nankervis B, Jones M, Vang B et al. (2018) Optimizing T Cell Expansion in a Hollow-Fiber Bioreactor. Curr Stem Cell Rep. Advanced online publication, https://doi.org/10.1007/s40778-018-0116-x.
Nankervis, Brian, et al. "Optimizing T cell expansion in a hollow-fiber bioreactor." Current Stem Cell Reports 4.1 (2018): 46-51.
Nedoszytko B, Lange M, Sokolowska-Wojdylo M, Renke J, Trzonkowski P, Sobjanek M, Szczerkowska-Dobosz A, Niedoszytko M, Gorska A, Romantowski J, Czarny J, Skokowski J, Kalinowski L, Nowicki R. The role of regulatory T cells and genes involved in their differentiation in pathogenesis of selected inflammatory and neoplastic skin diseases. Part II: The Treg role in skin diseases pathogenesis. Postepy Dermatol Alergol. 2017;34(5):405-417.
Nehlin JO, Just M, Rustan AC (2011) Human myotubes from myoblast cultures undergoing senescence exhibit defects in glucose and lipid metabolism. Biogerontology 12: 349-365.
New victories for adult Stem Cell Research New York Feb. 6, 2007.
Newton R, Priyadharshini B, Turka LA. Immunometabolism of regulatory T cells. Nat Immunol. 2016;17(6):618-25.
Ng TH, Britton GJ, Hill EV, Verhagen J, Burton BR, Wraith DC. Regulation of adaptive immunity; the role of interleukin-10. Front Immunol. 2013;4:129.
Nikolaychik, V. V., M. M. Samet, and P. I. Lelkes. "A New, Cryoprecipitate Based Coating For Improved Endothelial Cell Attachment And Growth On Medical Grade Artificial Surfaces." ASAIO Journal (American Society for Artificial Internal Organs: 1992) 40.3 (1994): M846-52.
Nish SA, Schenten D, Wunderlich FT, Pope SD, Gao Y, Hoshi N, Yu S, Yan X, Lee HK, Pasman L, Brodsky I, Yordy B, Zhao H, Bruning J, Medzhitov R. T cell-intrinsic role of IL-6 signaling in primary and memory responses. Elife. 2014;3:e01949.
Niwayama, Jun, et al. "Analysis of hemodynamics during blood purification therapy using a newly developed noninvasive continuous monitoring method." Therapeutic Apheresis and Dialysis 10.4 (2006): 380-386.
Okano et al. (Tokyo Women's Medical College, Japan) demonstrated the recovery of endothelial cells and hepatocytes from plasma-treated polystyrene dishes grafted with PNIAAm (Journal of Biomedical Materials Research, 1993).
Onishi Y, Fehervari Z, Yamaguchi T, Sakaguchi S. Foxp3+ natural regulatory T cells preferentially form aggregates on dendritic cells in vitro and actively inhibit their maturation. Proc Natl Acad Sci USA. 2008;105(29):10113-8.
Pacella I, Procaccini C, Focaccetti C, Miacci S, Timperi E, Faicchia D, Severa M, Rizzo F, Coccia EM, Bonacina F, Mitro N, Norata GD, Rossetti G, Ranzani V, Pagani M, Giorda E, Wei Y, Matarese G,

(56) References Cited

OTHER PUBLICATIONS

Barnaba V, Piconese S. Fatty acid metabolism complements glycolysis in the selective regulatory T cell expansion during tumor growth. Proc Natl Acad Sci USA. 2018;115(28):E6546-E6555.

Parhi, Purnendu, Avantika Goias, and Erwin A. Vogler. "Role Of Proteins And Water In The Initial Attachment Of Mammalian Cells To Biomedical Surfaces: A Review." Journal of Adhesion Science and Technology 24.5 (2010): 853-888.

Peters JH, Preijers FW, Woestenenk R, Hilbrands LB, Koenen HJ, Joosten I. Clinical grade Treg: GMP isolation, improvement of purity by CD127 Depletion, Treg expansion, and Treg cryopreservation. PLoS One. 2008;3(9):e3161.

Peters, R.; Jones, M.; Brecheisen, M.; Startz, T.; Vang, B.; Nankervis, B.; Frank, N.; Nguyen, K. (2012) TerumoBCT. https://www.terumobct.com/location/north-america/products-and-services/Pages/Quantum-Materials.aspx.

Porter CM, Horvath-Arcidiacono JA, Singh AK, Horvath KA, Bloom ET, Mohiuddin MM. Characterization and expansion of baboon CD4+CD25+ Treg cells for potential use in a non-human primate xenotransplantation model. Xenotransplantation. 2007;14(4):298-308.

Povsic TJ, O'Connor CM, Henry T, et al. (2011) A double-blind, randomized, controlled, multicenter study to assess the safety and cardiovascular effects of skeletal myoblast implantation by catheter delivery in patients with chronic heart failure after myocardial infarction. Am Heart J 162(4): 654-662.

Prockop, Darwin J., Carl A. Gregory, and Jeffery L. Spees. "One strategy for cell and gene therapy: harnessing the power of adult stem cells to repair tissues." Proceedings of the National Academy of Sciences 10Q.suppl_1 (2003): 11917-11923.

Q. L. Hao, et al. A functional comparison of CD34+ CD38= cells in cord blood and bone marrow. Blood 86:3745-3753, 1995.

Rey-Jurado, Emma, et al. "Assessing the importance of domestic vaccine manufacturing centers: an overview of immunization programs, vaccine manufacture, and distribution."Frontiers in immunology 9 (2018): 26.

Roballo KC, Dhungana S, Z. J, Oakey J, Bushman J. Localized delivery of immunosuppressive regulatory T cells to peripheral nerve allografts promotes regeneration of branched segmental defects. Biomaterials. 2019;209:1-9.

Rodrigues, C., Fernandes, T., Diogo, M., Lobato da Silva, C., Cabral, J. Stem Cell Cultivation in Bioreactors. 2011. Biotechnology Advances v. 29, pp. 815-829.

Ronco C1, Levin N, Brendolan A, Nalesso F, Cruz D, Ocampo C, Kuang D, Bonello M, De Cal M, Corradi V, Ricci Z. Flow distribution analysis by helical scanning in polysulfone hemodialyzers: effects of fiber structure and design on flow patterns and solute clearances. Hemodial Int. Oct. 2006; 10(4):380-8.

Ronco, C., Brendolan, A., Crepaldi, C., Todighiero, M., Scabardi, M. Blood and Dialysate Flow Distributions in Hollow-Fiber Hemodialyzers Analyzed by Computerized Helical Scanning Technigue. 2002. Journal of the American Society of Nephrology. V. 13, pp. S53-S61.

Rosenblum MD, Way SS, Abbas AK. Regulatory T cell memory. Nat Rev Immunol. 2016;16(2):90-101.

Rubtsov YP, Rasmussen JP, Chi EY, Fontenot J, Castelli L, Ye X, Treating P, Siewe L, Roers A, Henderson WR, Jr., Muller W, Rudensky AY. Regulatory T cell-derived interleukin-10 limits inflammation at environmental interfaces. Immunity. 2008;28(4):546-58.

Rudensky, Alexander Y. "Regulatory T cells and Foxp3." Immunological reviews 241.1 (2011): 260-268.

S. Koestenbauer, et al. Protocols for Hematopoietic Stem Cell Expansion from Umbilical Cord Blood. Cell Transplantation 18:1059-1068, 2009.

S. L. Smith, et al. Expansion of neutrophil precursors and progenitors in suspension cultures of CD34+ cells enriched from human bone marrow. Experimental Hematology 21:870-877, 1993.

Safinia N, Grageda N, Scotta C, Thirkell S, Fry LJ, Vaikunthanathan T, Lechler RI, Lombardi G. Cell Therapy in Organ Transplantation: Our Experience on the Clinical Translation of Regulatory T Cells. Front Immunol. 2018;9:354.

Sahay A, Scobie KN, Hill AS, O'Carroll CM, Kheirbek MA, Burghardt NS, Fenton AA, Dranovsky A, Hen R. Increasing adult hippocampal neurogenesis is sufficient to improve pattern separation. Nature. 2011;472:466-470.

Sakaguchi S, Sakaguchi N, Asano M, Itoh M, Toda M. Immunologic self-tolerance maintained by activated T cells expressing IL-2 receptor alpha-chains (CD25). Breakdown of a single mechanism of self-tolerance causes various autoimmune diseases. J Immunol. 1995;155(3):1151-64.

Sakaguchi S, Sakaguchi N, Shimizu J, Yamazaki S, Sakihama T, Itoh M, Kuniyasu Y, Nomura T, Toda M, Takahashi T. Immunologic tolerance maintained by CD25+ CD4+ regulatory T cells: their common role in controlling autoimmunity, tumor immunity, and transplantation tolerance. Immunol Rev. 2001;182:18-32.

Schild, Howard G. "Poly (N-isopropylacrylamide): experiment, theory and application." Progress in polymer science 17.2 (1992): 163-249.

Schmitz R, Alessio A, Kina P. The Physics of PET/CT scanners. Imaging Research Laboratory, Department of Radiology, University of Washington http://depts.washington.edu/imreslab/education/Physics%20of%20PET.pdf.

Schwartz RH. T cell anergy. Annu Rev Immunol. 2003;21:305-34.

Shevkoplyas et al., "The Force Acting on a Superparamagnetic Bead due to an Applied Magnetic Field," Lab on a Chip, 7, pp. 1294-1302, 2007.

Shimazu Y, Shimazu Y, Hishizawa M, Hamaguchi M, Nagai Y, Sugino N, Fujii S, Kawahara M, Kadowaki N, Nishikawa H, Sakaguchi S, Takaori-Kondo A. Hypomethylation of the Treg-Specific Demethylated Region in FOXP3 Is a Hallmark of the Regulatory T-cell Subtype in Adult T-cell Leukemia. Cancer Immunol Res. 2016;4(2):136-45.

Shimizu et al. (TWMU & Heart Institute of Japan) described the detachment of avian cardiomyocytes from PIPAAm matrixes that were observed to pulse spontaneously with neovascularization in layered sheets three (3) weeks after transplantation (Circulation Research, 2002).

Sigma-Aldrich Cheimcals Mitomycin C (M4287) Msds, v4.4, Jul. 7, 2011.

Sirsi, S. and Borden, M., "Microbubble Composition, Properties, and Biomedical Applications," Bubble Science, Engineering & Technolology, vol. 1, No. 1 -2, pp. 3-17, 2009.

Smith C, Okern G, Rehan S, et al. Ex vivo expansion of human T cells for adoptive immunotherapy using the novel Xeno-free CTS Immune Cell Serum Replacement. Clinical & Translational Immunology 2015;4:e31.

Somerville et al., "Clinical Scale Rapid Expansion of Lymphocytes for Adoptive Cell Transfer Therapy in the WAVE® Bioreactor," Journal of Translational Medicine, vol. 10, No. 69, pp. 1-11, 2012.

Somerville, R. and Dudley, M., "Bioreactors Get Personal," Oncolmmunology, vol. 1, No. 8, pp. 1435-1437, Nov. 2012.

Spectrum Labs KrosFlo Research Iii TFF System, undated, Spectrum Laboratories, Inc., 4 pages.

Stafano Tiziani, et al. Metabolomic Profiling of Drug Response in Acute Myeloid Leukaemia Cell lines. PLOSone 4(1): e4251 (Jan. 22, 2009).

StAR_Abstract, undated, author unknow, 1 page.

Startz et al. May 2016 TBCT T-cell White Paper.

Startz, T., et al. "Maturation of dendritic cells from CD14+ monocytes in an automated functionally closed hollow fiber bioreactor system." Cytotherapy 16.4 (2014): S29.

Steven M. Bryce, et al. (Litron Laboratories). In vitro micronucleus assay scored by flow cytometry provides a comprehensive evaluation of cytogenetic damage and cytotoxicity. Mutation Research 630(1-2): 78-91, 2007.

Steven M. Bryce, et al. (Novartis Pharma AG, Johnson & Johnson Pharmaceutical Research, GlaxoSmithKline). Interlaboratory evaluation of a flow cytometric, high content in vitro micronucleus assay. Genetic Toxicology and Environmental Mutagenesis 650:181-195, 2008.

(56) References Cited

OTHER PUBLICATIONS

Stuart, Martien A. Cohen, et al. "Emerging applications of stimuli-responsive polymer materials." Nature materials 9.2 (2010): 101-113.
Su LF, Del Alcazar D, Stelekati E, Wherry EJ, Davis MM. Antigen exposure shapes the ratio between antigen-specific Tregs and conventional T cells in human peripheral blood. Proc Natl Acad Sci USA. 2016;113(41):E6192-E6198.
The effect of rocking rate and angle on T cell cultures grown in Xuri™ Cell Expansion Systems, Aug. 2014, GE Healthcare UK Limited, 4 pages.
Trzonkowski et al., "Ex Vivo Expansion of CD4+ CD25+ T Regulatory Cells for Immunosuppressive Therapy," Cytometry Part A, 75A, pp. 175-188, 2009.
Trzonkowski, Piotr, et al. "First-in-man clinical results of the treatment of patients with graft versus host disease with human ex vivo expanded CD4+ CD25+ Cd 127? T regulatory cells." Clinical immunology 133.1 (2009): 22-26.
Tsvetkov, Ts, et al. "Isolation and cryopreservation of human peripheral blood monocytes." Cryobiology 23.6 (1986): 531-536.
Underwood, P. Anne, et al. "Effects of base material, plasma proteins and FGF2 on endothelial cell adhesion and growth." Journal of Biomaterials Science, Polymer Edition 13.8 (2002): 845-862.
Urbich, et al. from the Goethe-Universitat, demonstrated that human endothelial cells increased VEGFR-2 mRNA expression when exposed to 5-15 dynes/cm2 of constant shear force for a period of 6-24 hours (FEBS, 2002).
van der Net JB, Bushell A, Wood KJ, Harden PN. Regulatory T cells: first steps of clinical application in solid organ transplantation. Transpl Int. 2016;29(1):3-11.
van der Windt GJ, Pearce EL. Metabolic switching and fuel choice during T-cell differentiation and memory development. Immunol Rev. 2012;249(1):27-42.
Vera et al., "Accelerated Production of Antigen-Specific T-Cells for Pre-Clinical and Clinical Applications Using Gas-Permeable Rapid Expansion Cultureware (G-Rex)," J Immunother, vol. 33, No. 3, pp. 305-315, Apr. 2010.
Villa, Alma Y. Camacho, et al. "CD133+ CD34+ and CD133+ CD38+ blood progenitor cells as predictors of platelet engraftment in patients undergoing autologous peripheral blood stem cell transplantation." Transfusion and Apheresis Science 46.3 (2012): 239-244.
Visser EP1, Disselhorst JA, Brom M, Laverman P, Gotthardt M, Oyen WJ, Boerman OC. Spatial resolution and sensitivity of the Inveon small-animal PET scanner. J Nucl Med. Jan. 2009;50(1):139-47.
Walker, Peter A., et al. "Direct intrathecal implantation of mesenchymal stromal cells leads to enhanced neuroprotection via an NF?B-mediated increase in interleukin-6 production." Stem cells and development 19.6 (2010): 867-876.
Wang R, Dillon CP, Shi LZ, Milasta S, Carter R, Finkelstein D, McCormick LL, Fitzgerald P, Chi H, Munger J, Green DR. The transcription factor Myc controls metabolic reprogramming upon T lymphocyte activation. Immunity. 2011 ;35(6):871-82.
Wang, Jiamian, John A. Jansen, and Fang Yang. "Electrospraying: possibilities and challenges of engineering carriers for biomedical applications—a mini review." Frontiers in Chemistry 7 (2019): 258.
Ward H, Vigues S, Poole S, Bristow AF. The rat interleukin 10 receptor: cloning and sequencing of cDNA coding for the alpha-chain protein sequence, and demonstration by western blotting of expression in the rat brain. Cytokine. 2001;15(5):237-40.
Wawman, Rebecca Ellen, Helen Bartlett, and Ye Htun Oo. "Regulatory T cell metabolism in the hepatic microenvironment." Frontiers in immunology 8 (2018): 1889.
Weber et al., "White Paper on Adoptive Cell Therapy for Cancer with Tumor-Infiltrating Lymphocytes: A Report of the CTEP Subcommittee on Adoptive Cell Therapy," Clinical Cancer Research, vol. 17, No. 7, pp. 1664-1673, Apr. 1, 2011.
Weiss RA, Weiss MA, Beasley KL, Munavalli G (2007) Autologous cultured fibroblast injection for facial contour deformities: a prospective, placebo-controlled, Phase III clinical trial. Dermatol Surg 33(3): 263-268.
Widdel, F. 2010. "Theory and measurement of bacterial growth" http://www.mpi-bremen.de/Binaries/Binary13037/Wachstumsversuch.pdf.
Yamada, Noriko, et al. "Thermo-responsive polymeric surfaces; control of attachment and detachment of cultured cells." Die Makromolekulare Chemie, Rapid Communications 11.11 (1990): 571-576.
Yoshinari, Masao, et al. "Effect of cold plasma-surface modification on surface wettability and initial cell attachment." International Journal of Biomedical and Biological Engineering 3.10 (2009): 507-511.
Zappasodi et al., "The Effect Of Artificial Antigen-Presenting Cells with Preclustered Anit-CD28/-CD3/LFA-1 Monoclonal Antibodies on the Induction of ex vivo Expansion of Functional Human Antitumor T Cells," Haematologica, vol. 93, No. 10, pp. 1523-1534, 2008.
Zemmour D, Zilionis R, Kiner E, Klein AM, Mathis D, Benoist C. Publisher Correction: Singlecell gene expression reveals a landscape of regulatory T cell phenotypes shaped by the TCR. Nat Immunol. 2018;19(6):645.
Zeng B, Kwak-Kim J, Liu Y, Liao AH. Treg cells are negatively correlated with increased memory B cells in pre-eclampsia while maintaining suppressive function on autologous B-cell proliferation. Am J Reprod Immunol. 2013:70(6):454-63.
Zheng, et al at the University of Iowa have shown that the differential effects of pulsatile blood flow and cyclic stretch are an important growth stimulus (American Journal of Physiology—Heart and Circulatory Physiology, 2008).
Claudio G. Brunstein, Jeffrey S. Miller, Qing Cao, Daivd H. McKenna, Keii L. Hippen, Julie Curtsinger, Todd Defor, Bruce L. Levine, Carl H. June, Pablo Rubinstein, Philip B. McGlave, Bruce R. Blazar, and John E. Wagner. Infusion of ex vivo expanded T regulatory cells in adults transplanted with umbilical cord blood: safety profile and detection kinetics. Blood, 117(3): 1061-1070,2010.
Kim, Do-Hyung, et al. "mTOR interacts with raptor to form a nutrient-sensitive complex that signals to the cell growth machinery." Cell 110.2 (2002): 163-175.
Kishore M, Cheung KCP, Fu H, Bonacina F, Wang G, Coe D, Ward EJ, Colamatteo A, Jangani M, Baragetti A, Matarese G, Smith DM, Haas R, Mauro C, Wraith DC, Okkenhaug K, Catapano AL, De Rosa V, Norata GD, Marelli-Berg FM. Regulatory T Cell Migration Is Dependent on Glucokinase-Mediated Glycolysis. Immunity. 2017;47(5):875-889 e10.
Klysz D, Tai X, Robert PA, Craveiro M, Cretenet G, Oburoglu L, Mongellaz C, Floess S, Fritz V, Matias Ml, Yong C, Surh N, Marie JC, Huehn J, Zimmermann V, Kinet S, Dardalhon V, Taylor N. Glutamine-dependent alpha-ketoglutarate production regulates the balance between T helper 1 cell and regulatory T cell generation. Sci Signal. 2015;8(396):ra97.
Lindstein, Tullia, et al. "Regulation of lymphokine messenger RNA stability by a surface-mediated T cell activation pathway." Science 244.4902 (1989): 339-343.
Liotta, Francesco, et al. "Frequency of regulatory T cells in peripheral blood and in tumour-infiltrating lymphocytes correlates with poor prognosis in renal cell carcinoma." BJU international 107.9 (2011): 1500-1506.
Liu W, Putnam AL, Xu-Yu Z, Szot GL, Lee MR, Zhu S, Gottlieb PA, Kapranov P, Gingeras TR, Fazekas de St Groth B, Clayberger C, Soper DM, Ziegler SF, Bluestone Ja. CD127 expression inversely correlates with FoxP3 and suppressive function of human CD4+ T reg cells. J Exp Med. 2006;203(7):1701-1711.
Ueda, Ryosuke, et al. "Interaction of natural killer cells with neutrophils exerts a significant antitumor immunity in hematopoietic stem cell transplantation recipients." *Cancer medicine* 5.1 (2015): 49-60.
Jin, H., and J. Bae. "Neuropeptide Y regulates the hematopoietic stem cell microenvironment and prevents nerve injury in the bone marrow." *22nd Annual ISCT Meeting* (2016): S29.

(56) References Cited

OTHER PUBLICATIONS

Horwitz, Mitchell E., et al. "Phase I/II study of stem-cell transplantation using a single cord blood unit expanded ex vivo with nicotinamide." *Journal of Clinical Oncology* 37.5 (2019): 367-373.

Goh, Celeste, Sowmya Narayanan, and Young S. Hahn. "Myeloid-derived suppressor cells: the dark knight or the joker in viral infections?." *Immunological reviews* 255A (2013): 210-221.

Pati, Shibani, and Todd E. Rasmussen. "Cellular therapies in trauma and critical care medicine: Looking towards the future." *PLoS Medicine* 14.7 (2017): e1002343.

Pati, Shibani, et al. "Lyophilized plasma attenuates vascular permeability, inflammation and lung injury in hemorrhagic shock." *PLoS one* 13.2 (2018): e0192363.

* cited by examiner

CELL GROWTH WITH MECHANICAL STIMULI

CROSS-REFERENCE TO RELATED APPLICATION(S)

This patent application is a continuation of, and claims priority to, PCT International Patent Application No. PCT/US2016/040855, entitled "CELL GROWTH WITH MECHANICAL STIMULI," filed Jul. 1, 2016, which claims priority to U.S. Provisional Patent Application No. 62/188,332 entitled "ENDOTHELIAL CELL GROWTH," filed Jul. 2, 2015, both of which are hereby incorporated by reference in their entirety as if set forth herein in full.

BACKGROUND

Cell Expansion Systems (CESs) may be used to expand and differentiate a variety of cell types that may be used for both research and therapeutic purposes. Some cell types may positively respond to mechanical stimuli when expanded. In other words, subjecting the cell types to mechanical stimuli enhances their growth and proliferation. One example of a cell type that is a candidate to be grown in a CES and that responds positively to mechanical stimulus is endothelial cells. Endothelial cells play an important role in the development of vascular remodeling. As such, there is a need to design expansion methods for regenerative medicine that take into consideration the growing conditions that that may be used to efficiently grow cells, such as endothelial cells, ex vivo.

Embodiments of the present invention have been made in light of these and other considerations. However, the relatively specific problems discussed above do not limit the applicability of the embodiments of the present invention.

SUMMARY

The summary is provided to introduce aspects of some embodiments of the present invention in a simplified form, and is not intended to identify key or essential elements of the present invention, nor is it intended to limit the embodiments of the present invention.

Embodiments provide for methods and apparatuses that may be used in growing particular cell types that show improved growth/proliferation in response to mechanical stimulus, such as endothelial cells. Embodiments may include the use of hollow fiber membranes that may have inner diameters that provide a radius of curvature greater than a dimension (e.g., length or diameter) of a cell. In addition, embodiments may provide an undulating surface, pulsating flow rates, and other features that provide mechanical stimuli, which promotes or enhances the growth of the cells.

BRIEF DESCRIPTION OF THE DRAWINGS

Non-limiting and non-exhaustive embodiments are described with reference to the following figures.

DETAILED DESCRIPTION

Figure 1A:
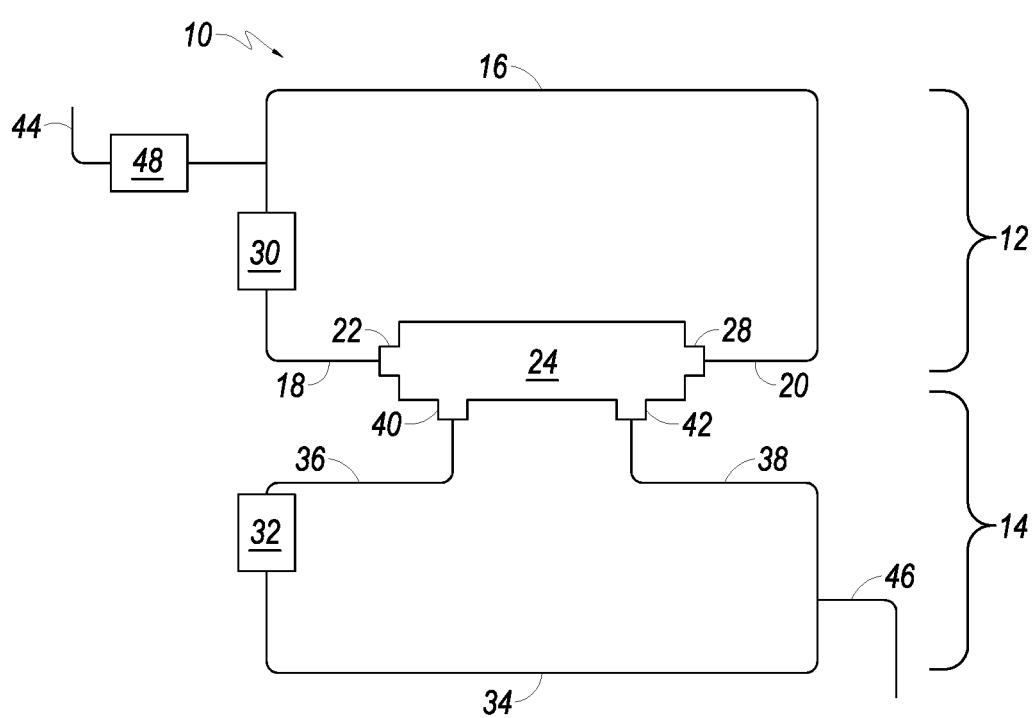
FIG. 1A depicts one embodiment of a cell expansion system (CES).

The principles of the present invention may be further understood by reference to the following detailed description and the embodiments depicted in the accompanying drawings. It should be understood that although specific features are shown and described below with respect to detailed embodiments, the present invention is not limited to the embodiments described below. It is noted that several embodiments are described with respect to loading or growing endothelial cells. However, the present invention is not limited to use with endothelial cells. Rather, the specific embodiments may be implemented with other cell types, some non-limiting examples including mesenchymal stem cells, fibroblasts, myoblasts, cardiomyocytes, etc.

Reference will now be made in detail to the embodiments illustrated in the accompanying drawings and described below. Wherever possible, the same reference numbers are used in the drawings and the description to refer to the same or like parts.

A schematic of an example cell expansion system (CES) 10 is depicted in FIG. 1A. CES 10 includes first fluid circulation path 12 and second fluid circulation path 14. First fluid flow path 16 has at least opposing ends 18 and 20 fluidly associated with a cell growth chamber 24 (also referred to herein as a "bioreactor"). Specifically, opposing end 18 may be fluidly associated with a first inlet 22 of cell growth chamber 24, and opposing end 20 may be fluidly associated with first outlet 28 of cell growth chamber 24. Fluid in first circulation path 12 may flow through the bioreactor. In those embodiments where the bioreactor is a hollow fiber bioreactor, the fluid may flow through the interior of hollow fiber of a hollow fiber membrane disposed in cell growth chamber 24 (hollow fiber membranes are described in more detail below). Further, first fluid flow controller 30 may be operably connected to first fluid flow path 16, and control the flow of fluid in first circulation path 12.

Second fluid circulation path 14 includes second fluid flow path 34, cell growth chamber 24, and a second fluid flow controller 32. The second fluid flow path 34 has at least opposing ends 36 and 38. Opposing ends 36 and 38 of second fluid flow path 34 are fluidly associated with inlet port 40 and outlet port 42 respectively of cell growth chamber 24. Fluid flowing through cell growth chamber 24, may, in embodiments, be in contact with the outside of a hollow fiber membrane in the cell growth chamber 24. Second fluid circulation path 14 may be operably connected to second fluid flow controller 32.

First and second fluid circulation paths 12 and 14 may in embodiments be separated in cell growth chamber 24 by a hollow fiber membrane. In these embodiments, fluid in first fluid circulation path 12 flows through the intracapillary ("IC") space, including the interior, of the hollow fibers in the cell growth chamber 24. First circulation path 12 is thus referred to as the "IC loop." Fluid in second fluid circulation path 14 flows through the extracapillary ("EC") space in the cell growth chamber 24. Second fluid circulation path 14 is thus referred to as the "EC loop." Fluid in first fluid circulation path 12 can flow in either a co-current or counter-current direction with respect to flow of fluid in second fluid circulation path 14. That is, fluid can flow clockwise or counter-clockwise in both the IC and EC loops, or they can flow in opposite directions.

Fluid inlet path 44 is fluidly associated with first fluid circulation path 12. Fluid inlet path 44 allows fluid to flow into first fluid circulation path 12, while fluid outlet path 46 allows fluid to leave CES 10. It is noted that in some embodiments a second fluid inlet path may be associated with second fluid circulation path 14 and a second outlet path may be associated with first fluid circulation path 12. Third fluid flow controller 48 is operably associated with fluid inlet path 44. A fourth fluid flow controller (not shown) may be associated with fluid outlet path 46, in some embodiments.

Fluid flow controllers as used herein can be a pump, valve, clamp, or combinations thereof. Multiple pumps, valves, and clamps can be arranged in any combination. In various embodiments, the fluid flow controller is or includes a peristaltic pump. In further embodiments, fluid circulation paths, inlet ports, and outlet ports can be constructed of tubing of any material.

Various components may be referred to herein as "operably associated." As used herein, "operably associated" refers to components that are linked together in operable fashion, and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g. a peristaltic pump that pumps fluids through flexible tubing by compressing the exterior of the tube).

Generally, any kind of fluid, including buffers, protein containing fluid, and cell-containing fluid can flow through the various circulations paths, inlet paths, and outlet paths. As used herein, "fluid," "media," and "fluid media" may refer to material (including liquids) being circulated though the various paths (e.g., inlet paths, circulation paths, outlet paths, etc.).

Figure 1B:
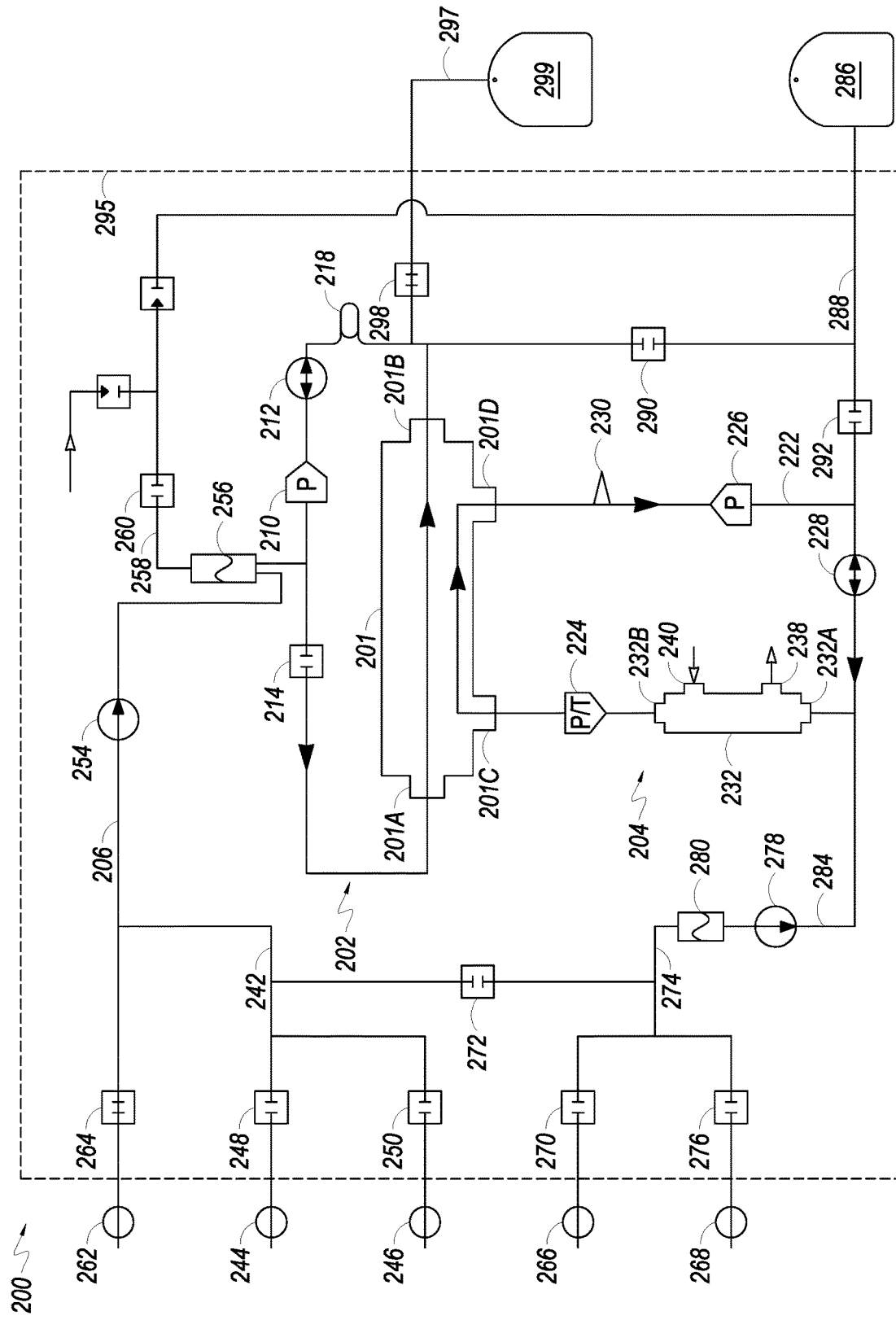
FIG. 1B depicts a second embodiment of a CES.

FIG. 1B depicts an example of a more detailed cell expansion system 200. CES 200 includes a first fluid circulation path 202 (also referred to as the "intracapillary loop" or "IC loop") and second fluid circulation path 204 (also referred to as the "extracapillary loop" or "EC loop"). First fluid flow path 206 is fluidly associated with a cell growth chamber (e.g., bioreactor 201) through fluid circulation path 202. Fluid flows into bioreactor 201 through IC inlet port 201A, through hollow fibers in bioreactor 201, and exits via IC outlet port 201B. Pressure sensor 210 measures the pressure of media leaving bioreactor 201. In addition to pressure, sensor 210 may in embodiments also be a temperature sensor that detects the media pressure and temperature during operation. Media flows through IC circulation pump 212 which can be used to control the rate of media flow, e.g., circulation rate in the IC loop. IC circulation pump 212 may pump the fluid in a first direction (e.g., clockwise or counter-clockwise) or second direction opposite the first direction. Exit port 201B can be used as an inlet in the reverse direction. Media entering the IC loop 202 may enter through valve 214. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES 200 and modifications to the schematic shown are within the scope of the one or more present embodiments.

With regard to the IC loop 202, samples of media can be obtained from sample coil 218 during operation. Media then returns to IC inlet port 201A to complete fluid circulation path 202. Cells grown/expanded in bioreactor 201 can be flushed out of bioreactor 201 into harvest bag 299 through valve 298 and line 297. Alternatively, when valve 298 is closed, the cells may be redistributed, e.g., circulated back, within bioreactor 201 for further growth or loading.

Fluid in second fluid circulation path 204 enters bioreactor 201 via EC inlet port 201C, and leaves bioreactor 201 via EC outlet port 201D. Media in the EC loop 204 is in contact with the outside of the hollow fibers in bioreactor 201, thereby allowing diffusion of small molecules into and out of the hollow fibers that may be within bioreactor 201.

Pressure/temperature sensor 224 disposed in the second fluid circulation path 204 and allows the pressure and temperature of media to be measured before the media enters the EC space of the bioreactor 201. Sensor 226 allows the pressure and temperature of media in the second fluid circulation path 204 to be measured after it leaves the cell growth chamber 201. With regard to the EC loop 204, samples of media can be obtained from sample port 230 or a sample coil during operation.

After leaving EC outlet port 201D of bioreactor 201, fluid in second fluid circulation path 204 passes through EC circulation pump 228 to gas transfer module 232. EC circulation pump 228 is also capable of being switched to pump the fluid in an opposite direction. Second fluid flow path 222 is fluidly associated with gas transfer module 232 via an inlet port 232A and an outlet port 232B of gas transfer module 232. In operation, fluid media flows into gas transfer module 232 via inlet port 232A, and exits gas transfer module 232 via outlet port 232B. Gas transfer module 232 adds oxygen to and removes bubbles from media in the CES 200. In various embodiments, media in second fluid circulation path 204 is in equilibrium with gas entering gas transfer module 232. The gas transfer module 232 can be any appropriately sized device known in the art and useful for oxygenation or gas transfer. Air or gas flows into gas transfer module 232 via filter 240 and out of oxygenator or gas transfer device 232 through filter 238. Filters 238 and 240 reduce or prevent contamination of oxygenator 232 and associated media. Air or gas purged from the CES 200 during portions of a priming sequence can vent to the atmosphere via the gas transfer module 232.

In the configuration depicted for CES 200, fluid media in first fluid circulation path 202 and second fluid circulation path 204 flows through bioreactor 201 in the same direction (a co-current configuration). The CES 200 can also be configured to flow in a counter-current configuration.

In accordance with at least one embodiment, media, including cells (from a source such as a cell container, e.g. a bag) can be attached at attachment point 262, and fluid media from a media source can be attached at attachment point 246. The cells and media can be introduced into first fluid circulation path 202 via first fluid flow path 206. Attachment point 262 is fluidly associated with the first fluid flow path 206 via valve 264, and attachment point 246 is fluidly associated with the first fluid flow path 206 via valve 250. A reagent source may be fluidly connected to point 244 and be associated with fluid inlet path 242 via valve 248, or second fluid inlet path 274 via valves 248 and 272.

Air removal chamber (ARC) 256 is fluidly associated with first circulation path 202. The air removal chamber 256 may include one or more sensors including an upper sensor and lower sensor to detect air, a lack of fluid, and/or a gas/fluid interface, e.g., an air/fluid interface, at certain measuring positions within the air removal chamber 256. For example, ultrasonic sensors may be used near the bottom and/or near the top of the air removal chamber 256 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 200 during portions of the priming sequence or other protocols can vent to the atmosphere out air valve 260 via line 258 that is fluidly associated with air removal chamber 256.

An EC media source may be attached to EC media attachment point 268 and a wash solution source may be attached to wash solution attachment point 266, to add EC media and/or wash solution to either the first and/or second fluid flow path. Attachment point 266 may be fluidly associated with valve 270 that is fluidly associated with first fluid circulation path 202 via valve 272 and path 242. Alternatively, attachment point 266 can be fluidly associated with second fluid circulation path 204 via second fluid inlet path 274 and EC inlet path 284 by opening valve 270 and closing valve 272. Likewise, attachment point 268 is fluidly associated with valve 276 that may be fluidly associated with first fluid circulation path 202 via first fluid inlet path 242 and valve 272. Alternatively, attachment point 268 may be fluidly associated with second fluid inlet path 274 by opening valve 276 and closing valve distribution 272.

In the IC loop 202, fluid may be initially advanced by the IC inlet pump 254. In the EC loop 204, fluid is initially advanced by the EC inlet pump 278. An air detector 280, such as an ultrasonic sensor, may also be associated with the EC inlet path 284.

In at least one embodiment, first and second fluid circulation paths 202 and 204 are connected to waste line 288. When valve 290 is opened, IC media can flow through waste line 288 and to waste bag 286. Likewise, when valve 292 is opened, EC media can flow to waste bag 286.

After cells have been grown in bioreactor 201, they may be harvested via cell harvest path 297. Cells from cell growth chamber 201 can be harvested by pumping the IC media containing the cells through cell harvest path 297, with valve 298 open, into cell harvest bag 299.

Figure 1C:
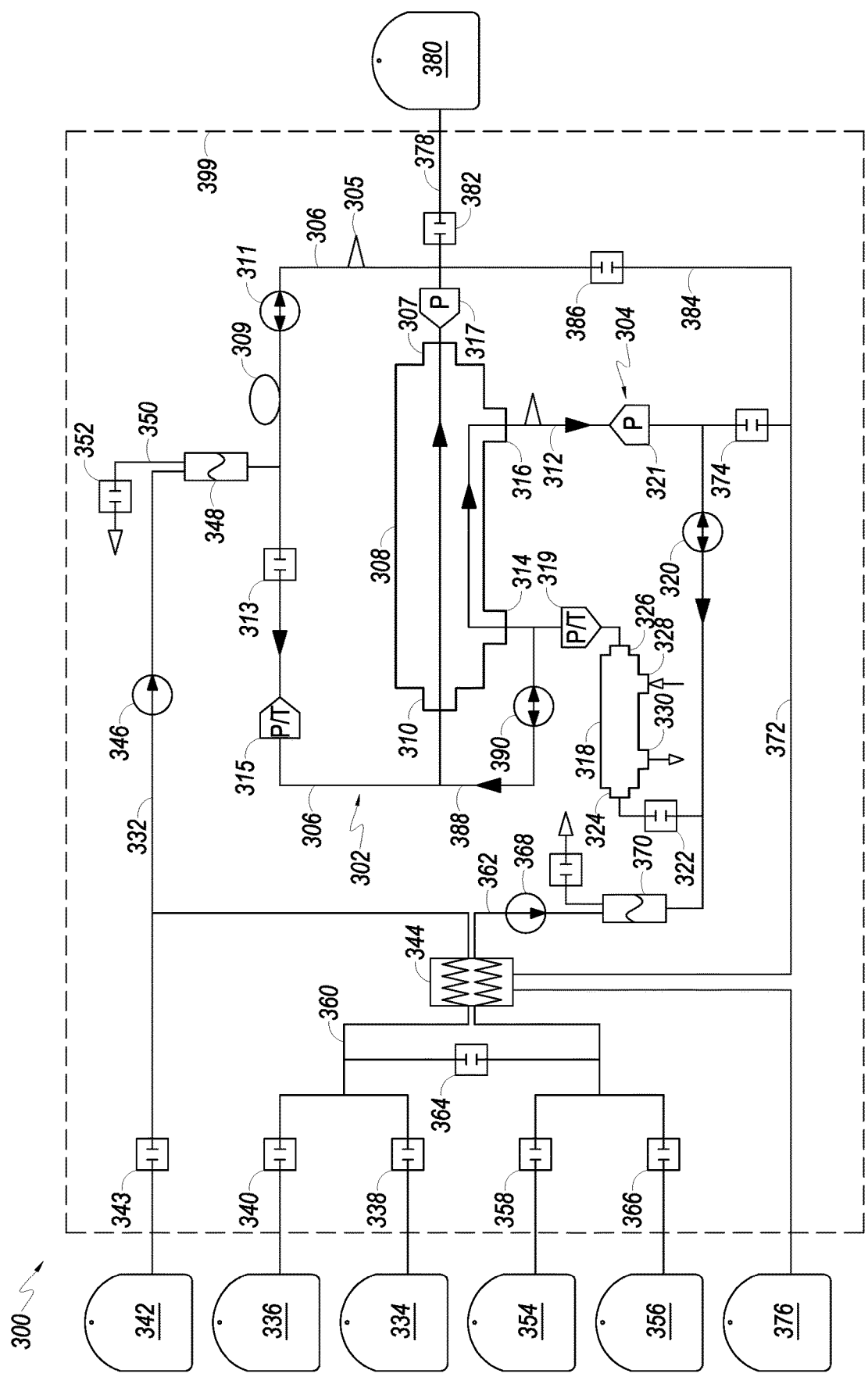
FIG. 1C depicts a third embodiment of a CES.

Various components of the CES 200 can be contained or housed within a machine or housing 295, such as cell expansion machine, wherein the machine maintains cells and media at a predetermined temperature. It is further noted that in embodiments, components of CES 200 may be combined with other CES's such as CES 10 (FIG. 1A) or CES 300 (FIG. 1C). In other embodiments, a CES may include fewer components than shown in FIGS. 1A-C and still be within the scope of the present disclosure.

FIG. 1C depicts another embodiment of a CES. CES 300 includes first fluid circulation path 302 (also referred to as the "intracapillary (IC) loop") and second fluid circulation path 304 (also referred to as the "extracapillary loop" or "EC loop").

First fluid flow path 306 is fluidly associated with cell growth chamber 308 through first fluid circulation path 302. Fluid may flow into cell growth chamber 308 through inlet port 310, (e.g., through hollow fibers) in cell growth chamber 308, and exit via outlet port 307. Pressure gauge 317 measures the pressure of media leaving cell growth chamber 308. Media may flow through valve 313 and pump 311, which can be used to control the rate of media flow in the IC loop 302. Samples of media can be obtained from sample port 305 or sample coil 309 during operation. Pressure/temperature gauge 315 disposed in first fluid circulation path 302 allows detection of media pressure and temperature during operation. Media then returns to inlet port 310 to complete fluid circulation path 302. Cells expanded in cell growth chamber 308 can be flushed out of cell growth chamber 308 or redistributed within hollow fibers for further growth.

Second fluid circulation path 304 includes second fluid flow path 312 that is fluidly associated with cell growth chamber 308 in a loop. Fluid in second fluid circulation path 304 may enter cell growth chamber 308 via inlet port 314, and leaves cell growth chamber 308 via outlet port 316.

Media is in contact with the outside of the hollow fibers in the cell growth chamber 308, allowing diffusion of small molecules into and out of the hollow fibers.

Pressure/temperature gauge 319 disposed in the second circulation path 304 allows the pressure and temperature of media to be measured before the media enters the EC space of the cell growth chamber 308. Pressure gauge 321 allows the pressure of media in the second circulation path 304 to be measured after it leaves the cell growth chamber 308.

After leaving outlet port 316 of cell growth chamber 308, fluid in second fluid circulation path 304 passes through pump 320 and valve 322 to oxygenator 318. Second fluid flow path 312 is fluidly associated with oxygenator 318 via oxygenator inlet port 324 and oxygenator outlet port 326. In operation, fluid media flows into oxygenator 318 via oxygenator inlet port 324, and exits oxygenator 318 via oxygenator outlet port 326.

Oxygenator 318 adds oxygen to media in the CES 300. In various embodiments, media in second fluid circulation path 304 is in equilibrium with gas entering oxygenator 318. The oxygenator can be any oxygenator known in the art. Gas flows into oxygenator 318 via filter 328 and out of oxygenator 318 through filter 330. Filters 328 and 330 reduce or prevent contamination of oxygenator 318 and associated media.

In the configuration depicted for CES 300, fluid media in first circulation path 302 and second circulation path 304 flow through cell growth chamber 308 in the same direction (a co-current configuration). Those of skill in the art will recognize that CES 300 can also be configured in a counter-current configuration. Those of skill in the art will recognize that the respective inlet and outlet ports can be disposed in the cell growth chamber 308 at any location.

Cells and fluid media can be introduced to fluid circulation path 302 via first fluid inlet path 332. Fluid container 334 and fluid container 336 are fluidly associated with first fluid inlet path 332 via valves 338 and 340 respectively. Likewise, cell container 342 is fluidly associated with first fluid circulation path 302 via valve 343. Cells and fluid may in some embodiments proceed through heat exchanger 344, pump 346, and into drip chamber 348 before entering path 302. In embodiments where cells from container 342 are passed through heat exchanger 344, an additional line (not shown) would be used to connect container 342 to heat exchanger 344. Drip chamber 348 is fluidly associated with first circulation path 302. Overflow from drip chamber 348 can flow out of drip chamber 348 from overflow line 350 via valve 352.

Additional fluid can be added to first or second fluid circulation paths 302 and 304 from fluid container 354 and fluid container 356. Fluid container 354 is fluidly associated with valve 358 which is fluidly associated with first fluid circulation path 302 via valve 364, path 360, and path 332. Alternatively, fluid container 354 is fluidly associated with second fluid inlet path 362. Likewise, fluid container 356 is fluidly associated with valve 366, which is fluidly associated with first fluid circulation path 302 via first fluid inlet path 360. Alternatively, fluid container 356 is fluidly associated with second fluid inlet path 362.

Second fluid inlet path 362 is configured to allow fluid to flow through heat exchanger 344, pump 368, before entering drip chamber 370. Second fluid inlet path 362 continues to second fluid circulation path 304. Overflow fluid from second fluid circulation path 304 can flow out via overflow line 372 through valve 374 to waste container 376.

Cells can be harvested via cell harvest path 378. Cells from cell growth chamber 308 can be harvested by pumping media containing the cells through cell harvest path 378 to cell harvest bag 380, when valve 382 is opened.

First and second fluid circulation paths 302 and 304 are connected by connector path 384. When valve 386 is opened, media can flow through connector path 384 between first and second circulation paths 302 and 304. Likewise, pump 390 can pump media through another connector path 388 between first and second fluid circulation paths 302 and 304.

Various components of the CES 300 can be contained within incubator 399. Incubator 399 may maintain cells and media at a constant temperature.

As will be recognized by those of skill in the art, any number of fluid containers (e.g. media bags) can be fluidly associated with the CES 300 in any combination. It will further be noted that the location of the drip chamber 348, or sensors independent of the drip chamber 348, can be at any location in the CES 300 before inlet port 310.

CES's 200 and 300 can include additional components. For example, one or more pump loops (not shown) can be added at the location of peristaltic pumps on a CES. The pump loops may be made of polyurethane (PU) (available as Tygothane C-210A)). Alternatively, a disposable cassette for organizing the tubing lines and which may also contain tubing loops for the peristaltic pumps may also be included as part of the disposable.

A detachable flow circuit (also referred to herein as a "detachable flow circuit") may also be provided in some embodiments. The detachable flow circuit may in embodiments incorporate portions of a cell expansion system (e.g., portions of CES 10, 200 and 300) and be configured to attach to more permanent fixed portions of the CES (e.g., other portions of CES 10, 200 and 300). The fixed portions of the CES may include peristaltic pumps. In various embodiments, the fixed portions of the CES can include valves and/or clamps.

The detachable flow circuit can include a first fluid flow path having at least two ends. The first end may be configured to be fluidly associated with a first end of a cell growth chamber, and a second end of the first fluid flow path configured to fluidly associated with a second end of the cell growth chamber (see, e.g., paths 12, 202, and 302).

Likewise, the detachable flow circuit can include a second fluid flow path having at least two ends. Portions of the detachable flow circuit can be configured to be fluidly associated with an oxygenator and/or bioreactor. The detachable flow circuit can include a second fluid flow path that may be configured to fluidly associate with the oxygenator and cell growth chamber (see, e.g., paths 14, 204, and 304).

In various embodiments, the detachable flow circuit may be detachably and disposably mounted to a fluid flow controller. The detachable flow circuit can include detachable fluid conduits (e.g. flexible tubing) that connect portions of the CES.

In further embodiments, the detachable flow circuit can include a cell growth chamber, oxygenator, as well as bags for containing media and cells. In various embodiments, the components can be connected together, or separate. Alternatively, detachable flow circuit can include one or more portions configured to attach to fluid flow controllers, such as valves, pumps, and combinations thereof. In variations where peristaltic pumps are used, the detachable circuit module can include a peristaltic loop configured to fit around a peristaltic portion of the tubing. In various embodiments, the peristaltic loop can be configured to be fluidly associated with the circulations paths, inlet paths, and outlet paths. The detachable flow circuit can be combined in a kit with instructions for its assembly or attachments to fluid flow controllers, such as pumps and valves.

Embodiments provide for using a number of different methods to introduce cells into bioreactors of CES. As described in greater detail below, embodiments include methods and systems that distribute cells in the bioreactor to promote consistent expansion of cells.

According to embodiments, cells can be grown ("expanded") in either the IC loop or the EC loop. Adherent and non-adherent suspension cells can be expanded. In one embodiment, the lumen of the cell growth chamber fibers can be coated with fibronectin. Divalent cation-free (e.g. calcium and magnesium-free) PBS may be added to a CES system for example. After adherent cells are introduced into a cell growth chamber, e.g., chamber 24, 201, or 308 they may be incubated for a sufficient time to adhere to the hollow fibers. IC and EC media may be circulated to ensure sufficient nutrients are supplied to the cells to allow them to grow.

The flow rate of the IC loop and EC loop can be adjusted to a specific value. In various embodiments, the flow rate of the IC loop and EC loops can be, independently set to, about 2, about 4, about 6, about 8, about 10, about 15, about 20, about 25, about 30, about 35, about 40, about 45, about 50, about 60, about 70, about 80, about 90, about 100, about 200, about 300, about 400 or even about 500 mL/minute. In various embodiments, the flow rates for the IC circuit loop may be set from about 10 to about 20 mL/minute, and the flow rate of the EC circuit loop may be set from 20 to about 30 mL per minute (allowing media to flow through an oxygenator and re-establish oxygen levels). Additional media may be pumped into the CES at a lower flow rate (e.g. 0.1 mL per minute in some embodiments) to replace media that evaporates through a gas exchange module(s) such as gas exchange/oxygenators 232 and 218. In various embodiments, the EC loop removes cellular waste, and the IC loop includes growth factors in the media.

CES's may provide a great deal of flexibility in varying growth conditions and criteria. Cells can be kept in suspension in the IC loop by circulating media continuously. Alternatively, media circulation can be stopped, causing cells to settle. Fresh media can be added to the IC loop by ultrafiltration to accommodate excess volume without removing cells. EC media circulation allows for exchange of gas, nutrients, waste products, and addition of new media without removing cells.

Expanded cells can include adherent cells, non-adherent cells, or a co-culture of any combination of cells. Some non-limiting examples of cells that maybe grown in embodiments of a CES, include, without limitation, stem cells (e.g., mesenchymal, hematopoietic, etc.), fibroblasts, keratinocytes, progenitor cells, endothelial cells, cardiomyocytes, other fully differentiated cells, and combinations thereof.

In embodiments, to harvest adherent cells, the IC and EC media may be replaced with media that is free of divalent cations (e.g. divalent cation-free PBS). In one embodiment, trypsin may be loaded into a first circulation path, and allowed to incubate with adherent cells for a period of time (in some embodiments about 5 to about 10 minutes). The trypsin may then be flushed from the system. A shearing force may be applied to the cells by increasing the flow rate through cell growth chamber, and adherent cells that are released from the cell growth chamber may be pumped to a cell harvest bag.

When non-adherent cells are expanded, the cells can be flushed from the circulating IC circuit. Adherent cells remain in the cell growth chamber, while non-adherent cells are removed.

The CES can be used to perform a variety of cell expansion methods. In one embodiment, a seeded population of cells can be expanded. Cells are introduced, or seeded, into the CES. In certain circumstances, the lumen of the hollow fibers can be conditioned to allow cell adhesion. Cells are then added to the cell growth chamber, and adherent cells adhere to the hollow fibers, while non-adherent cells (e.g. hematopoietic stem cells, or HSCs) do not adhere. The non-adherent cells can be flushed from the system. After incubation for a period of time, the adherent cells can be released and harvested.

The cell growth chamber of the cell expansion system in embodiments includes a hollow fiber membrane comprised of a plurality of semi-permeable hollow fibers separating first and second fluid circulation paths. Embodiments of hollow fibers, hollow fiber membranes, and bioreactors are described below in greater detail.

Figure 2:
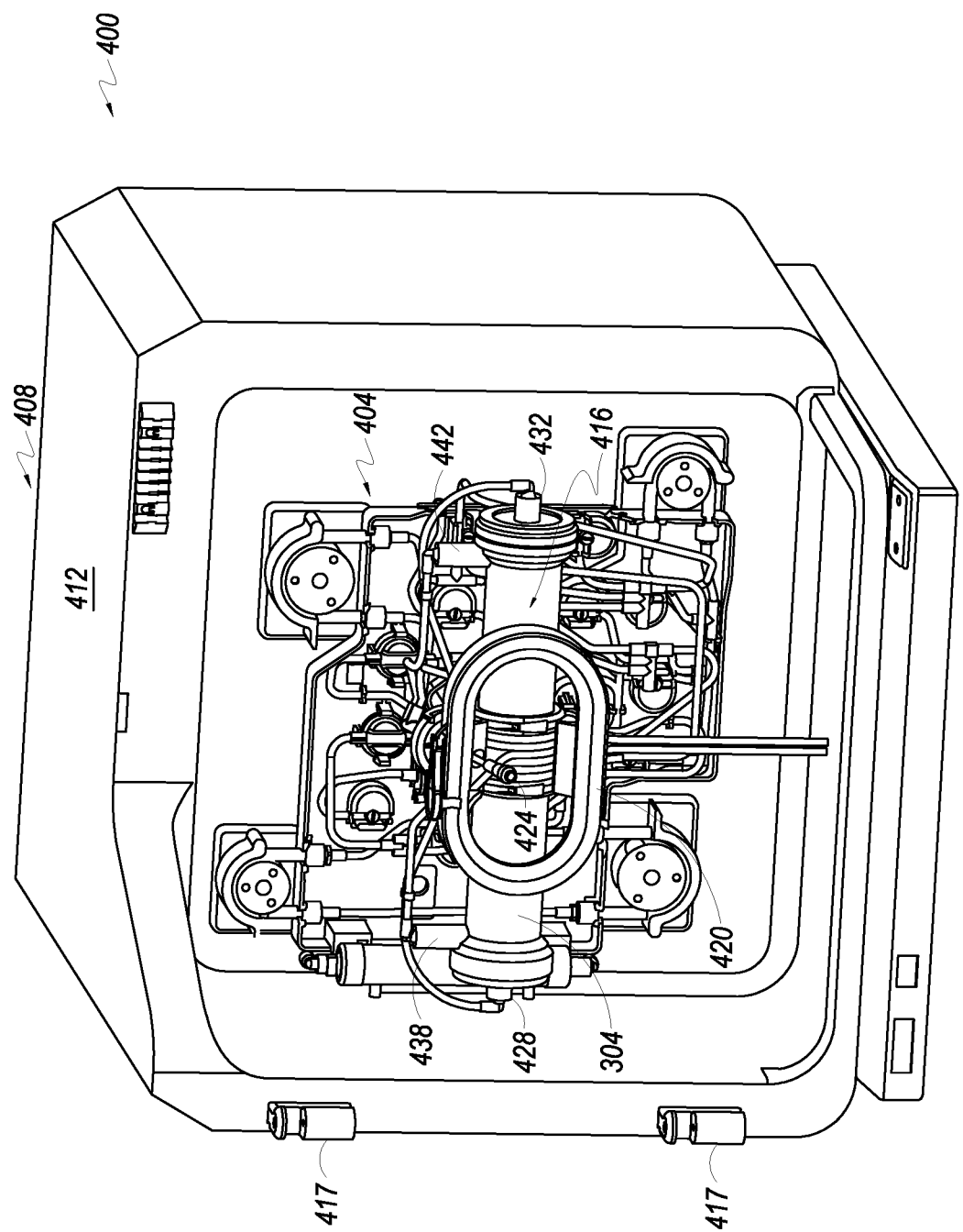
FIG. 2 illustrates a perspective view of a portion of a CES, including a detachably attached flow circuit, according to an embodiment.

Referring now to FIG. 2, a portion of an embodiment of a CES 400 is shown in perspective view. CES 400 includes both a detachable flow circuit 404 that may be disposable (in embodiments) and a permanent portion 408. The permanent portion 408 includes a back 412. For clarity, the front (or door) of the permanent portion 408 is not shown; however, the front may be attached to the back 412, such as by hinges 417, thereby allowing the front to comprise a door or hatch that can be opened to access the detachable flow circuit, which include a bioreactor 416. Attached to the bioreactor 416 may be a spool 420 for tubing and a sampling port 424.

As shown in FIG. 2, bioreactor 416 includes a first inlet port 428, a first outlet port 432, a second inlet port 438, and a second outlet port 442. In embodiments, first inlet port 428 and first outlet port 432 may be part of an IC circulation loop (e.g. 12, 202, and/or 302). Second inlet port 438 and second outlet port 442 may be part of an EC circulation loop (e.g. 14, 204, and/or 304)

In embodiments, CES 400 may control the temperature of detachable flow circuit 404. The detachable flow circuit 404 and its components may be connected to permanent portion 408 and the front closed to enclose the detachable flow circuit 404. Permanent portion 408 may then include heating elements, cooling elements, etc. to control the temperature inside permanent portion 408 to a desired temperature for growing cells in bioreactor 416 of detachable flow circuit 404.

Figure 3A:
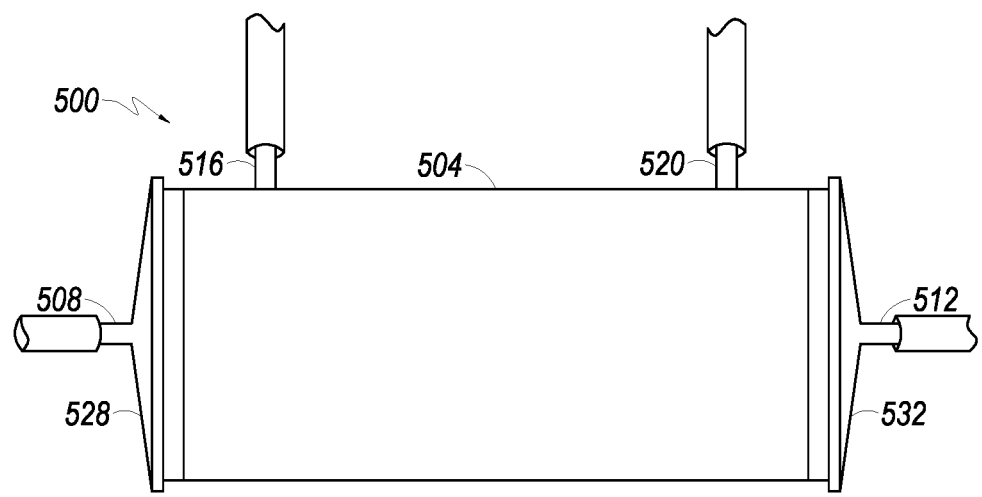
FIG. 3A depicts a side view of an embodiment of a hollow fiber cell growth chamber.
Figure 3B:
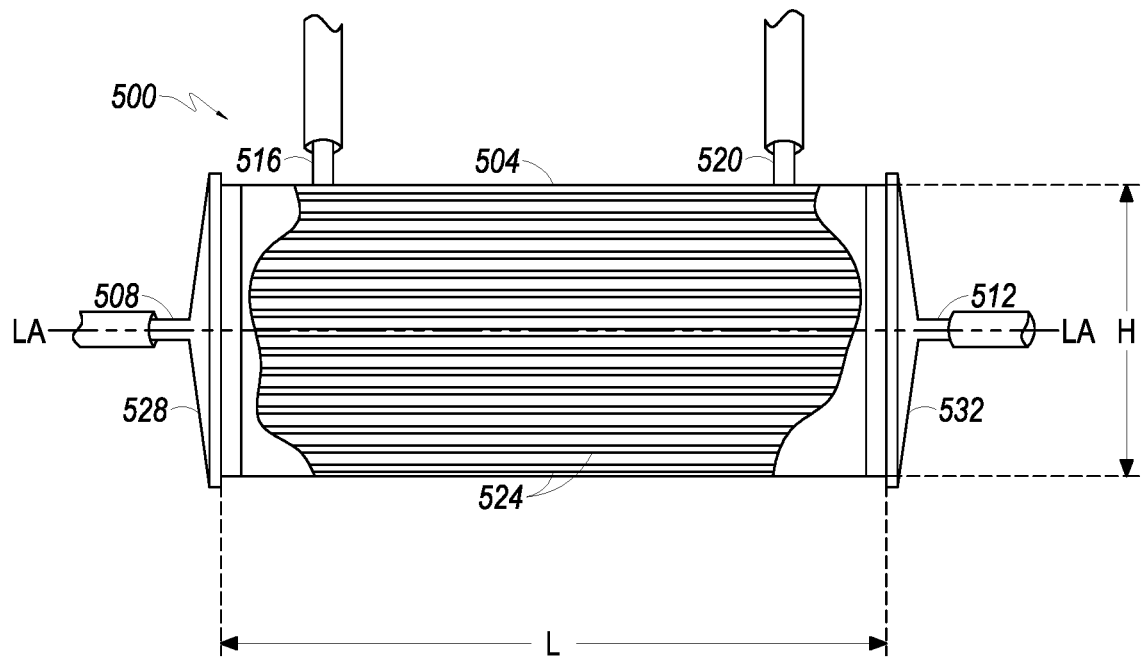
FIG. 3B depicts a cut-away side view of the bioreactor shown in FIG. 3A.

Referring now to FIGS. 3A and 3B, embodiments of a cell growth chamber 500 are depicted in FIGS. 3A and 3B, which may be referred to as a "bioreactor." FIG. 3B depicts a cut-away and side view of a hollow fiber cell growth chamber 500. Cell growth chamber 500 is bounded by cell growth chamber housing 504. Cell growth chamber housing 504 further includes four openings, or ports: inlet port 508, outlet port 512, inlet port 516, and outlet port 520. In addition, chamber 500 has a longitudinal axis LA-LA as shown in FIG. 3B. Longitudinal axis LA-LA is generally parallel to a length dimension "L" of cell growth chamber 500. Longitudinal axis LA-LA is generally perpendicular to a height dimension "H" of cell growth chamber 500.

Fluid in the first circulation path may enter cell growth chamber 500 through inlet port 508, pass into and through the intracapillary side of a plurality of hollow fibers 524 (referred to in various embodiments as the intracapillary ("IC") side or "IC space" of a hollow fiber membrane), and out of cell growth chamber 500 through outlet port 512. The terms "hollow fiber," "hollow fiber capillary," and "capillary" may be used interchangeably. A plurality of hollow fibers 524 are collectively referred to as a "membrane." Fluid in the second circulation path flows in the cell growth chamber through inlet port 516, comes in contact with the outside of the hollow fibers 524 (referred to as the "EC side" or "EC space" of the membrane), and exits cell growth chamber 500 via outlet port 520. Cells can be contained within the first circulation path or second circulation path, and can be on either the IC side or EC side of the membrane.

Although cell growth chamber housing 504 is depicted as cylindrical in shape, it can have other shapes, in other embodiments. Cell growth chamber housing 504 can be made of any type of biocompatible polymeric material. Various other cell growth chamber housings may differ in shape and size.

Those of skill in the art will recognize that the term cell growth chamber does not imply that all cells being grown or expanded in a CES are grown in the cell growth chamber. In many embodiments, adherent cells can adhere to membranes disposed in the growth chamber, or may grow within the associated tubing. Non-adherent cells (also referred to as "suspension cells") can also be grown. Cells can be grown in other areas within the first or second fluid circulation path.

For example, the ends of hollow fibers 524 can be potted to the sides of the cell growth chamber 500 by a connective material (also referred to herein as "potting" or "potting material"). The potting can be any suitable material for binding the hollow fibers 524, provided that the flow of media and cells into the hollow fibers is not obstructed and that fluid (e.g., liquid) flowing into the cell growth chamber 500 through the IC inlet port flows only into the hollow fibers 524. An exemplary potting material includes, but is not limited to polyurethane. Other suitable binding or adhesive components may also be used in embodiments. In various embodiments, the hollow fibers 524 and potting may be cut through perpendicular to a central axis of the hollow fibers 524 at each end to permit fluid flow into and out of the IC side. End caps 528 and 532 may be disposed at the ends of the cell growth chamber.

Fluid entering cell growth chamber 500 via inlet port 516 is in contact with the outside of hollow fibers 524. This portion of the hollow fiber cell growth chamber is referred to as the "extracapillary (EC) space." Small molecules (e.g. water, oxygen, lactate, etc.) can diffuse through the hollow fibers 524 from the interior of the hollow fiber to the EC space, or from the EC space to the IC space. Large molecular weight molecules such as growth factors are typically too large to pass through the hollow fibers 524, and remain in the IC space of the hollow fibers. In embodiments in which cells are grown in the IC space, the EC space is used as a medium reservoir to supply nutrients to the cells and remove the byproducts of cellular metabolism. The media may be replaced as needed. Media may also be circulated through an oxygenator to exchange gasses as needed.

In various embodiments, cells can be loaded into the hollow fibers 524 by any of a variety of methods, including by syringe. The cells may also be introduced into the cell growth chamber 500 from a fluid container, such as a bag, which may be fluidly associated with the cell growth chamber. Some specific examples of method for loading cells into bioreactor/hollow fibers are discussed below (see, e.g., FIG. 12).

Hollow fibers 524 may in embodiments allow cells to grow in the intracapillary space (i.e. inside the hollow fiber lumen) of the fibers. Hollow fibers 524 may be large enough to allow cell adhesion in the lumen without substantially impeding the flow of media through the hollow fiber lumen. In embodiments, the inner diameter of the hollow fiber can be greater than or equal to about 50 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 1000 microns, about 1100 microns, about 1200 microns, about 1300 microns, about 1400 microns, about 1500 microns, about 1600 microns, about 1700 microns, about 1800 microns, about 1900 microns, about 2000 microns, about 3000 microns, about 4000 microns, about 5000 microns, about 6000 microns, about 7000 microns, about 8000 microns, about 9000 microns, or even greater than or equal to about 10000 microns.

Likewise, in embodiments, the outer diameter of the hollow fibers 524 can be less than or equal to about 10000 microns, about 9000 microns, about 8000 microns, about 7000 microns, about 6000 microns, about 5000 microns, about 4000 microns, about 3000 microns, about 2000 microns, about 1000 microns, about 900 microns, about 800 microns, about 700 microns, about 650 microns, about 700 microns, about 650 microns, about 600 microns, about 550 microns, about 500 microns, about 450 microns, about 400 microns, about 350 microns, about 300 microns, about 250 microns, about 200 microns, about 150 microns, or even less than or equal to about 100 microns. The hollow fiber wall thickness may be sufficiently thin and have other characteristics (e.g., porous) to allow diffusion of small molecules.

Any number of hollow fibers can be used in a cell growth chamber according to embodiments, provided the hollow fibers can be fluidly associated with the inlet and outlet ports of the cell growth chamber. In embodiments, the cell growth chamber can include a number of hollow fibers greater than or equal to about 1000, about 2000, about 3000, about 4000, about 5000, about 6000, about 7000, about 8000, about 9000, about 10000, about 11000 or even greater than or equal to about 12000. In other embodiments, the cell growth chamber can include a number of hollow fibers less than or equal to about 15000, about 14000, about 13000, about 12000, about 11000, about 10000, about 9000, about 8000, about 7000, about 6000, about 5000, about 4000, about 3000, or even less than or equal to about 2000. In other various embodiments, the length of the hollow fibers can be greater than or equal to about 100 millimeters, about 200 millimeters, about 300 millimeters, about 400 millimeters, about 500 millimeters, about 600 millimeters, about 700 millimeters, about 800 millimeters, or even about 900 millimeters. In some embodiments, the cell growth chamber may include about 9000 hollow fibers that have an average length of about 295 millimeters, an average inner diameter of 215 microns, and an average outer diameter of about 315 microns.

Hollow fibers may be constructed of any material capable of forming a size sufficient to form fibers capable of transporting fluid (e.g., liquid) from the cell growth chamber inlet port to the cell growth chamber outlet port. In various embodiments, the hollow fibers can be constructed from plastic adherent materials capable of binding to certain types of cells, such as adherent stem cells (e.g. MSCs) as one non-limiting example. In various other embodiments, hollow fibers can be treated with compounds such as fibronectin to form adherent surfaces.

In certain embodiments, the hollow fibers may be made of a semi-permeable, biocompatible polymeric material. One such polymeric material which can be used is a blend of polyamide, polyarylethersulfone and polyvinylpyrrolidone (referred to herein as "PA/PAES/PVP"). The semi-permeable membrane may allow transfer of nutrients, waste and dissolved gases through the membrane between the EC space and IC space. In various embodiments, the molecular transfer characteristics of the hollow fiber membranes may be chosen to minimize loss of expensive reagents necessary for cell growth such as growth factors, cytokines etc. from the hollow fiber, while allowing metabolic waste products to diffuse through the membrane into the hollow fiber lumen side to be removed.

In embodiments, one outer layer of each PA/PAES/PVP hollow fiber may be characterized by a homogenous and open pore structure with a defined surface roughness. The openings of the pores may be in the size range of about 0.5 to about 3 microns, and the number of pores on the outer surface of the fibers may be in the range of about 10,000 to about 150,000 pores per $mm^2$. This outer layer may have a thickness of from about 1 to about 10 microns. The next layer in each hollow fiber may be a second layer having the form of a sponge structure and, in embodiments may have a thickness of from about 1 to about 15 microns. This second layer may serve as a support for the outer layer. A third layer next to the second layer may have the form of finger-like structures. This third layer may provide mechanical stability and a high void volume which may give the membrane a low resistance to transporting molecules through the membrane. During use, the finger-like voids may be filled with fluid and the fluid may give a lower resistance for diffusion and convection than a matrix with a sponge-filled structure having a lower void volume. This third layer may have a thickness of about 20 to about 60 microns.

In further embodiments, the hollow fiber membrane can include between about 65 to about 95% by weight of at least one hydrophobic polymer and between about 5 to about 35% by weight of at least one hydrophilic polymer. The hydrophobic polymer may be chosen from the group consisting of polyamide (PA), polyaramide (PAA), polyarylethersulphone (PAES), polyethersulphone (PES), polysulphone (PSU), polyarylsulphone (PASU), polycarbonate (PC), polyether, polyurethane (PUR), polyetherimide and copolymer mixtures of any of the above polymers, such as polyethersulphone or a mix of polyarylethersulphone and polyamide. In additional embodiments, the hydrophilic polymer may be chosen from the group consisting of polyvinylpyrrolidone (PVP), polyethylene glycol (PEG), polyglycolmonoester, water soluble cellulosic derivates, polysorbate and polyethylene-polypropylene oxide copolymers.

In other embodiments, the fibers may have a combination of features that provide optimized conditions for growing a particular cell. As may be appreciated, some cell types may prefer particular structural features for optimum growth. In embodiments, hollow fibers may include features that optimize the growth of some cells types by providing a mechanical stimulus. Non-limiting examples of these cell types include endothelial cells and cardiomyocytes. For example, the hollow fibers may have a growth surface (i.e., interior surface) that has a radius of curvature that is greater than a dimension (e.g., diameter, length, etc.) of the cells. In embodiments, for use in growing endothelial cells, the hollow fibers may have an inner diameter less than about 300 microns, less than about 275 microns, less than about 250 microns, or even less than about 225 microns. In other embodiments, the hollow fibers may have an inner diameter greater than about 50 microns, about 100 microns, greater than about 150 microns, or even greater than about 200 microns. In other embodiments, for growing endothelial cells, the hollow fibers may have inner diameters that are between about 150 microns and about 250 microns, such as between about 160 microns and about 240 microns, between about 170 microns and about 230 microns, between about 180 microns and about 220 microns, or even between about 190 microns and about 210 microns.

In addition to inner diameter, growing of cells may be enhanced by providing an undulating, e.g., a surface with some texture. In some embodiments, the hollow fibers may include an interior surface that includes features that provide an uneven or undulating surface. For example, in some embodiments for growing endothelial cells, the interior surface of the hollow fiber may have features that provide some surface roughness. The features may generally extend parallel to a longitudinal axis of the hollow fiber. In other embodiments, the features may extend perpendicular to the longitudinal axis of the hollow fiber. As a result of these features, the interior surface of the hollow fiber may have a surface roughness of between about 10 nanometers and about 100 nanometers, such as between about 20 nanometers and about 90 nanometers, between about 30 nanometers and about 80 nanometers, or even between about 40 nanometers and about 70 nanometers. In other embodiments for growing endothelial cells, the interior surface of the hollow fibers may have a surface roughness that is greater than about 10 nanometers, greater than about 15 nanometers, greater than about 20 nanometers, greater than about 25 nanometers, greater than about 30 nanometers, greater than about 35 nanometers, greater than about 40 nanometers, or even greater than about 45 nanometers. In other embodiments for growing endothelial cells, the interior surface of the hollow fibers may have a surface roughness that is less than about 150 nanometers, less than about 140 nanometers, less than about 130 nanometers, less than about 120 nanometers, less than about 110 nanometers, less than about 110 nanometers, less than about 90 nanometers, less than about 85 nanometers, less than about 80 nanometers, less than about 75 nanometers, less than about 70 nanometers, less than about 65 nanometers, less than about 60 nanometers, or even less than about 55 nanometers.

Figure 4:
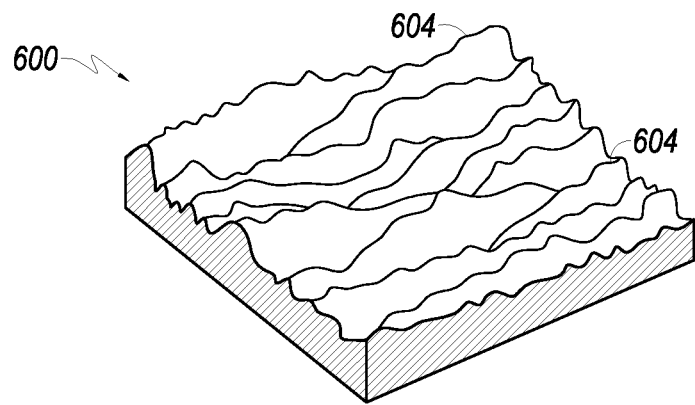
FIG. 4 illustrates surface features of an uncoated surface of a hollow fiber that may be used in embodiments.
Figure 5:
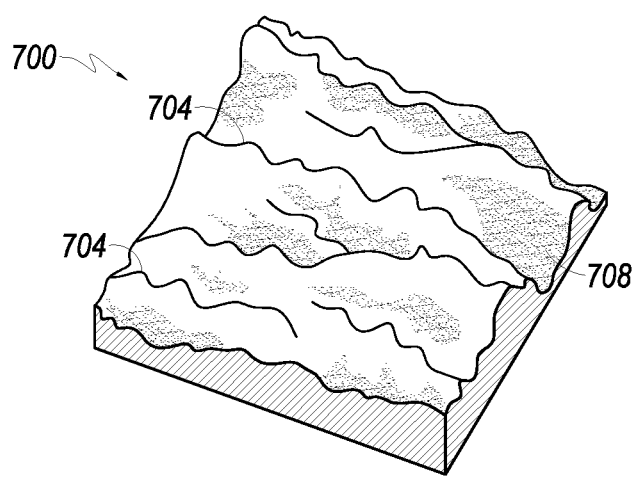
FIG. 5 illustrates surface features of a coated surface of a hollow fiber that may be used in embodiments.

FIGS. 4 and 5 illustrate a representation of surface features (604, 704) on an inside surface (600, 700), e.g., lumen wall, of hollow fibers, according to embodiments. The features (604, 704) provide an undulating surface that, as indicated below, may promote the growth of some cells, e.g., endothelial cells. FIG. 4 illustrates an embodiment of an uncoated surface 600 from an interior of a hollow fiber and illustrates features 604. The features are elongated and undulating and create surface roughness. FIG. 5 illustrates an embodiment of an interior surface 700 of a hollow fiber coated with fibronectin 708. FIG. 5 illustrates features 704 similar to features 604. As illustrated in FIGS. 4 and 5, embodiments of hollow fibers provide features that create an undulating surface. Features 604 and 704 may in some embodiments extend along a length of the hollow fiber. In other embodiments, the features 604 and 708 may extend perpendicular, or at some other angle, with respect to a length dimension of the hollow fiber.

Further, depending upon the type of cells to be expanded, the hollow fibers may be treated with a substance, such as fibronectin 708, to enhance cell growth and/or adherence of the cells to the lumen wall. The substance can then be removed or deactivated in order to detach the cells from the surface of the hollow fiber.

It is noted that in some embodiments, a combination of structural features of a growth surface, e.g., hollow fiber, may enhance growth of certain cell types. For example, in some embodiments, the combination of a radial surface with a radius of curvature greater than an average cell dimension, such as a length or diameter (e.g., hollow fiber with inner diameter of about 215±10 µm in some embodiments) with an undulating 3D surface topography (e.g., ±20-40 nm) in a hollow fiber membrane bioreactor may be used to advance cell priming and proliferation, e.g., endothelial cells. In addition, the other adherent cell types such as neural stem cells or mesenchymal stem cells may also be more efficiently (e.g., under optimized conditions) grown using the structural features described. These are merely some examples.

It is noted that the structural features described above (surface roughness and fiber inner diameter) for enhancing the growth of some cells is provided merely for illustrative purposes. In other embodiments, the hollow fiber diameter, surface roughness, or other structural features, may be changed depending on the cell type being expanded in the cell growth chamber to enhance growth of different cell types.

Figure 6:
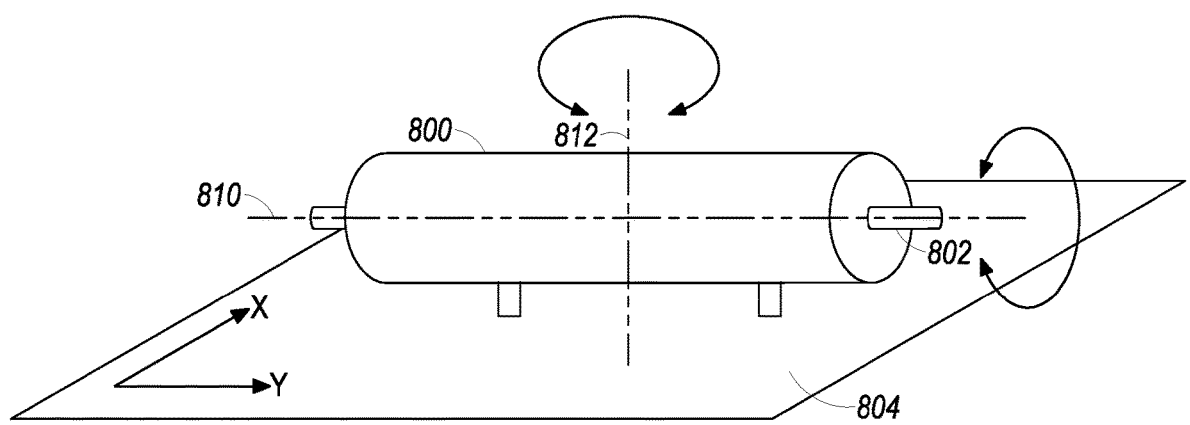
FIG. 6 depicts an embodiment of a rocking device for moving a cell growth chamber rotationally or laterally during operation of a CES.

In addition to structural features, some embodiments provide for creating conditions in a CES controlled by fluid flow that optimizes growth of cells. As one example, a CES can include a device configured to move or "rock" a cell growth chamber relative to other components of the cell expansion system by attaching it to a rotational and/or lateral rocking device. FIG. 6 shows one such device, in which a bioreactor 800 is rotationally connected to two rotational rocking components, and a lateral rocking component.

A first rotational rocking device component 802 rotates the bioreactor 800 around longitudinal axis 810 of the bioreactor. Bioreactor 800 is also connected to lateral rocking device 804. Rotational rocking device component 802 is rotationally associated to bioreactor 800. The rotational rocking device 802 then rotates bioreactor 800 around longitudinal axis 810 of the bioreactor. Rotation can occur in a clockwise or counter-clockwise direction. Bioreactor 800 can be rotated continuously in a single direction around central axis 810 in a clockwise or counterclockwise direction. Alternatively, bioreactor 800 can rotate in alternating fashion, first clockwise, then counterclockwise around longitudinal axis 810.

The CES can also include a second rotational rocking component that rotates bioreactor 800 around rotational axis 812 so that longitudinal axis 810 is moved. Rotational axis 812 passes through the center of point of bioreactor 800 and is normal to longitudinal axis 810. Bioreactor 800 can be rotated continuously in a single direction around rotational axis 812 in a clockwise or counterclockwise direction. Alternatively, bioreactor 800 can be rotated around rotational axis 812 in an alternating fashion, first clockwise, then counterclockwise. In various embodiments, bioreactor 800 can also be rotated around rotational axis 812 and positioned in a horizontal or vertical orientation.

Lateral rocking component 804 is laterally associated with bioreactor 800. The plane of lateral rocking component 804 moves laterally in the −x and −y directions. The settling of cells in the bioreactor 800 is thereby reduced with the movement of cell-containing media within the hollow fibers.

The rotational and/or lateral movement of the rocking device can reduce the settling of cells within the device and reduce the likelihood of cells becoming trapped within a portion of the bioreactor 800. The rate of cells settling in the cell growth chamber (e.g., bioreactor 800) is proportional to the density difference between the cells and the suspension media according to Stoke's Law. In certain embodiments, a 180 degree rotation with a pause (e.g., having a total combined time of 30 seconds) repeated may keep non-adherent cells suspended. A minimum rotation of about 180 degrees may be performed in some embodiments; however, one could use rotation of up to 360 degrees or greater in other embodiments. Different rocking components can be used separately, or can be combined in any combination. For example, a rocking component that rotates bioreactor 800 around central axis 810 can be combined with the rocking component that rotates bioreactor 800 around axis 812. Likewise, clockwise and counterclockwise rotation around different axes can be performed independently in any combination.

It is noted that the rocking devices, and their components, described above, may be implemented in embodiments using any appropriate structure. For example, in embodiments, one or more motors may be used as rocking devices, or components (e.g. 802 and 804) of rocking devices. In one embodiment, the rocking devices may be implemented using embodiments shown and described in U.S. Pat. No. 8,399, 245 entitled ROTATION SYSTEM FOR CELL GROWTH CHAMBER OF A CELL EXPANSION SYSTEM AND METHOD OF USE THEREFOR, issued Mar. 19, 2013, which is hereby incorporated by reference in its entirety as if set forth herein in full.

FIGS. 7-11 illustrate various positions of a bioreactor 900 according to embodiments. As described below, some embodiments provide for rotating a bioreactor during various steps. The steps may be performed as part of a process of loading cells into a bioreactor/CES, while in other embodiments; the steps may be performed as part of a process of growing or feeding cells that have been loaded into a bioreactor/CES. As described in greater detail below, in some embodiments, the rotation of the bioreactor from and to various positions may provide conditions (e.g., fluid flow) for creating conditions that enhance growth of some cell types, e.g., endothelial cells.

Figure 7:
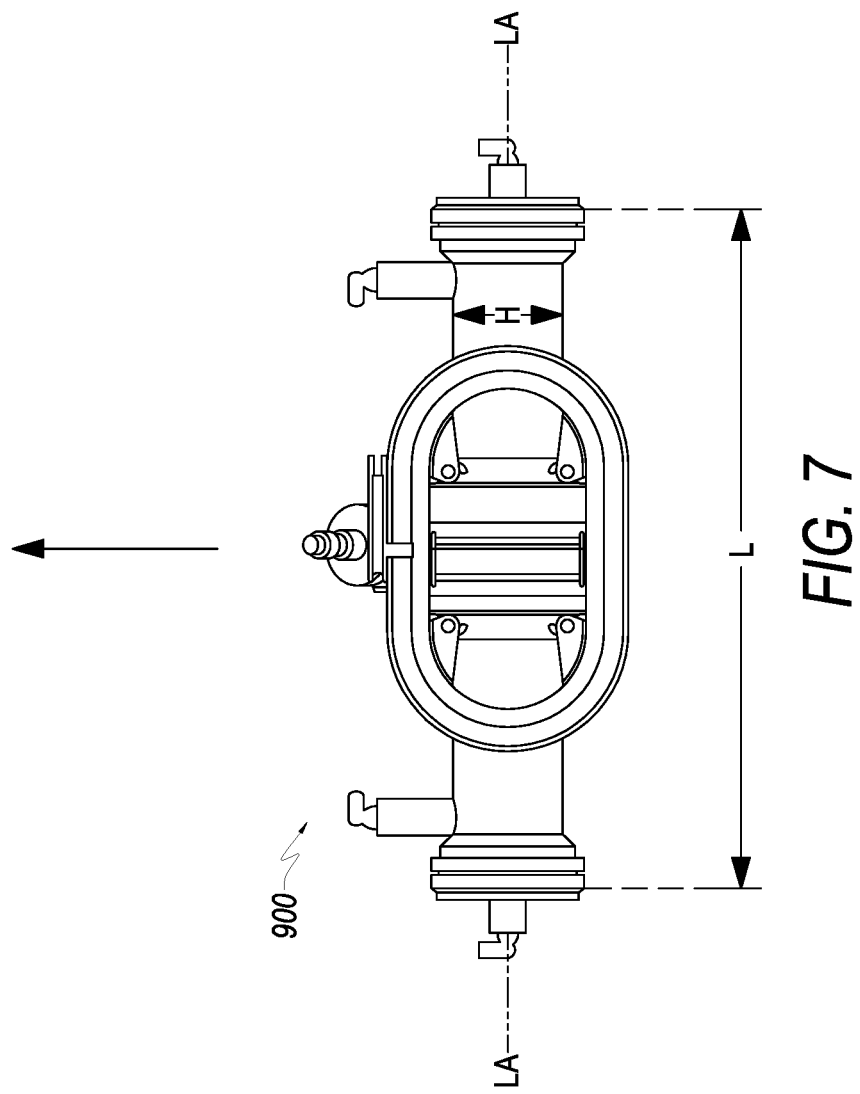
FIG. 7 illustrates an embodiment of a cell growth chamber (e.g., bioreactor) with a longitudinal axis LA-LA in an initial position.
Figure 8:
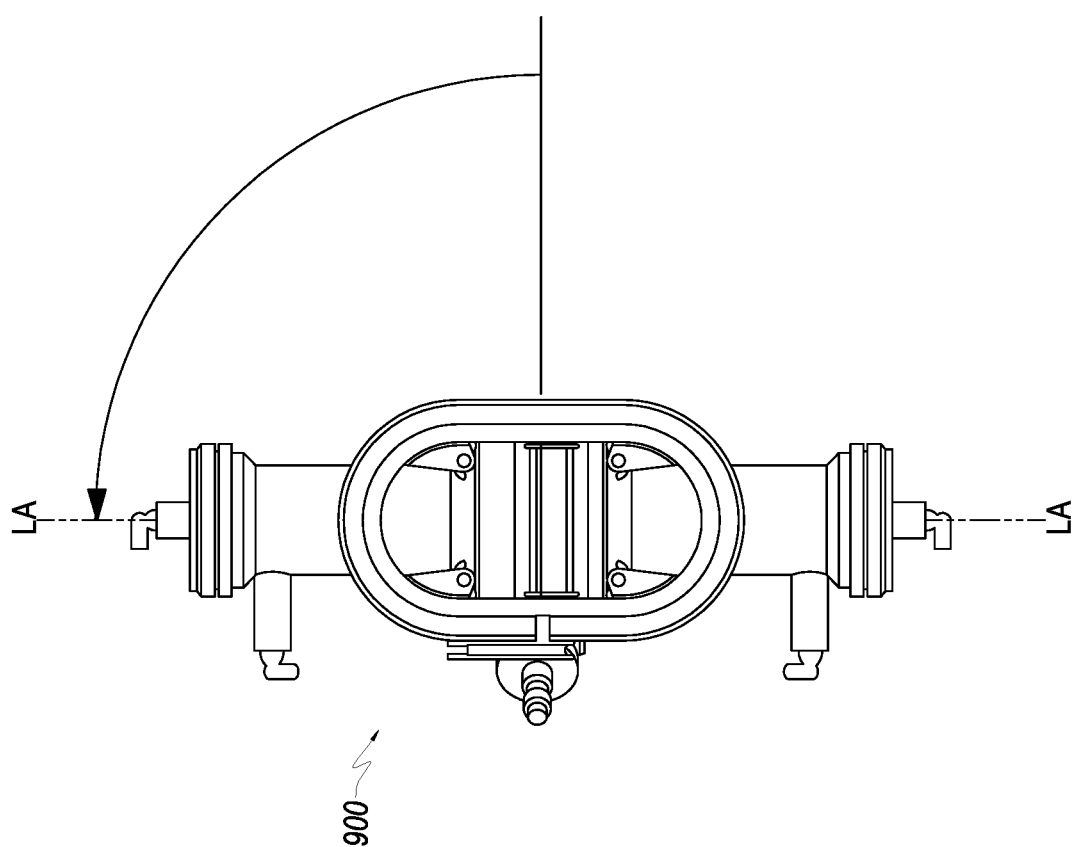
FIG. 8 illustrates an embodiment of the cell growth chamber of FIG. 7 with the longitudinal axis LA-LA moved 90 degrees from the initial position.
Figure 9:
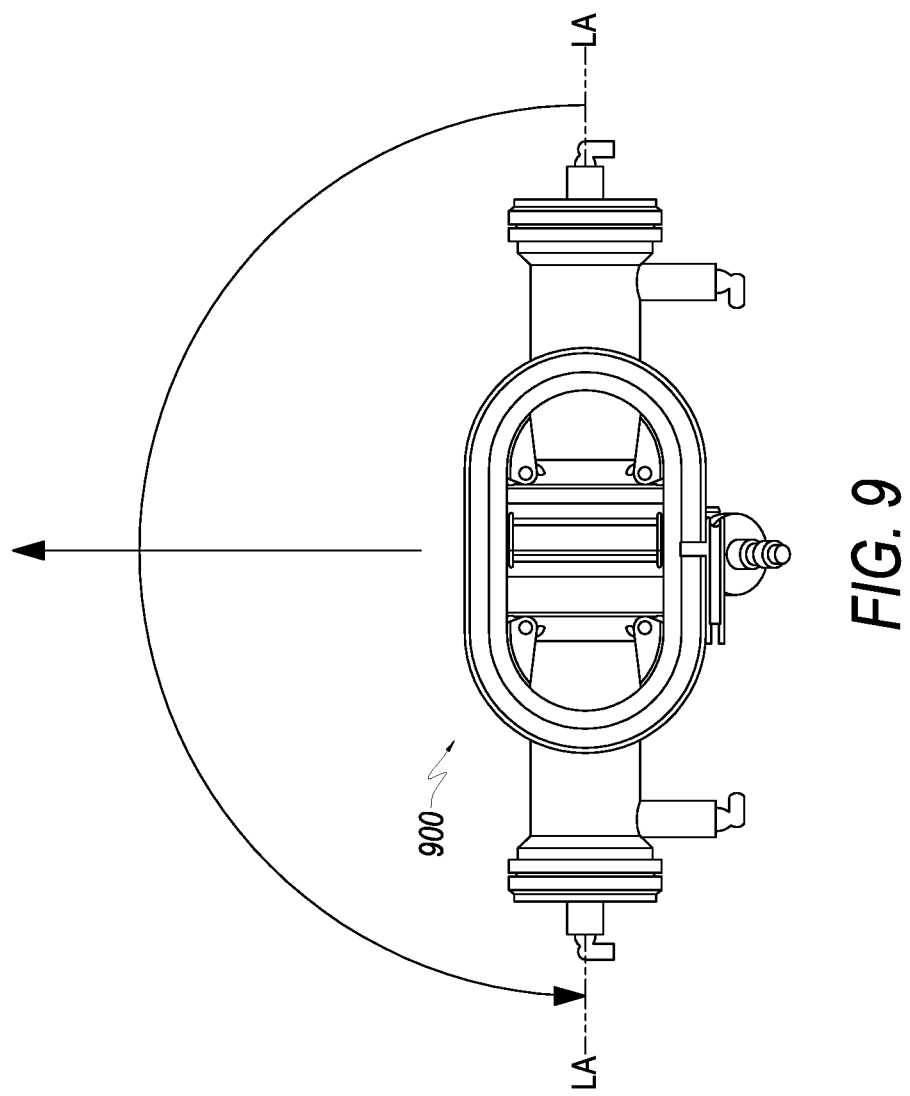
FIG. 9 illustrates an embodiment of the cell growth chamber of FIG. 7 with the longitudinal axis LA-LA moved 180 degrees from the initial position.
Figure 10:
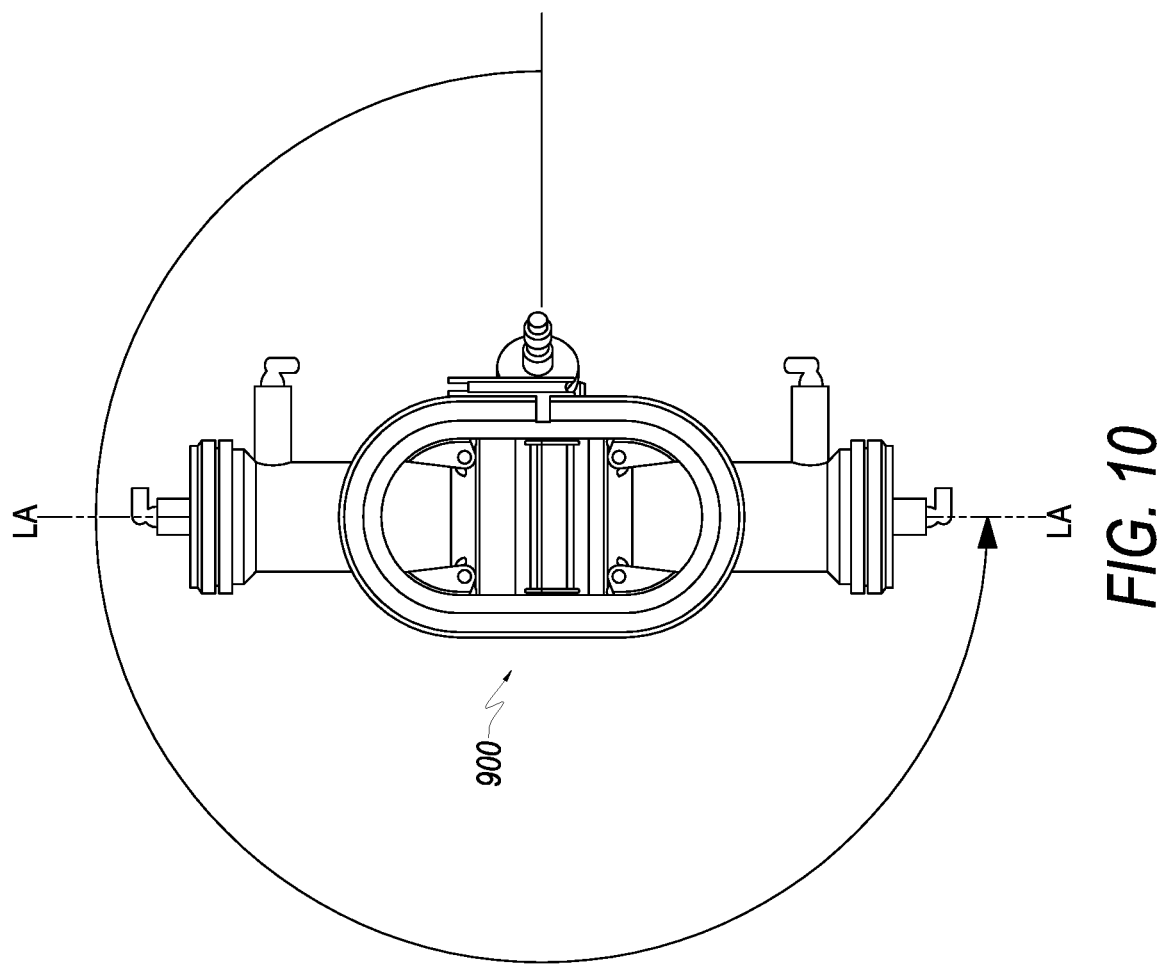
FIG. 10 illustrates an embodiment of the cell growth chamber of FIG. 7 with the longitudinal axis LA-LA moved 270 degrees from the initial position.
Figure 11:
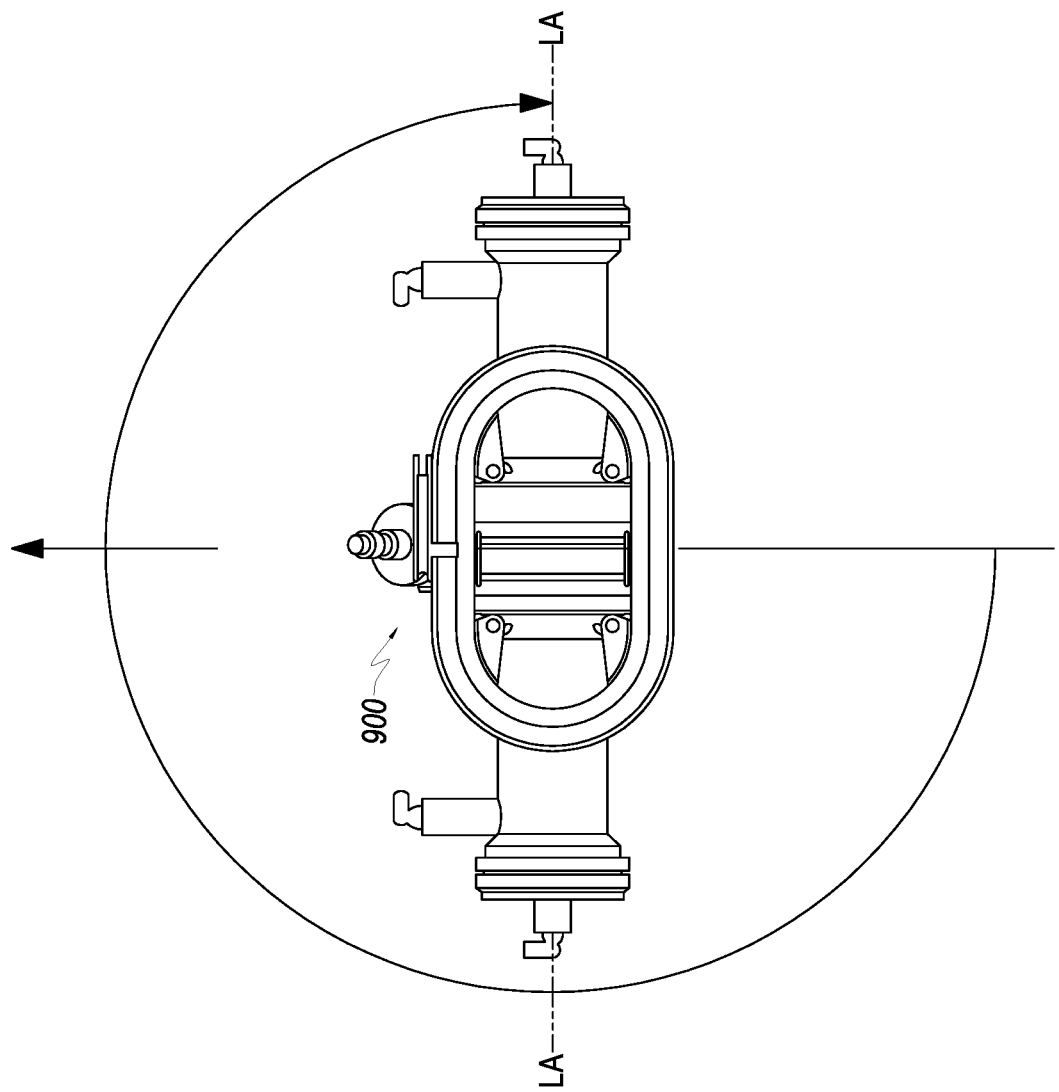
FIG. 11 illustrates an embodiment of the cell growth chamber of FIG. 7 with the longitudinal axis LA-LA moved 270 degrees back to the initial position.

Referring to FIG. 7, and in accordance with at least one embodiment, the orientation of the bioreactor 900 is shown in a first position, which may be an initial starting position. As illustrated in FIG. 7, longitudinal axis LA-LA of the bioreactor 900 is substantially horizontal. FIG. 8 illustrates the bioreactor 100 in a second position, with LA-LA rotated 90 degrees from the position shown in FIG. 7. FIG. 9 illustrates the bioreactor 900 in a third position, with LA-LA rotated 180 degrees from the position shown in FIG. 7. FIG. 10 illustrates the bioreactor 900 in a fourth position, with LA-LA rotated 270 degrees from the position shown in FIG. 7. FIG. 11 illustrates bioreactor 900 after it is rotated back 270 degrees, with LA-LA back in the same position as shown in FIG. 7.

As described in greater detail below, rotation of a bioreactor may be performed in various processes to load, feed, and grow cells. The rotation may result in particular conditions that improve the growth of cell types in a CES. As one non-limiting example, a sequence of manipulations (e.g., rotations) may be undertaken to mitigate the influence of gravity on the cells when being loaded into the bioreactor 100. As another example, the rotation may be used in creating a pulsatile effect that may mimic a heart beat that creates an improved environment for growing particular types of cells. Also, although in FIGS. 7-11 the bioreactor is described as initially starting with longitudinal axis LA-LA in a substantially horizontal position, in other embodiments, any of the positions (FIGS. 7-11) may be an initial position.

Figure 12:
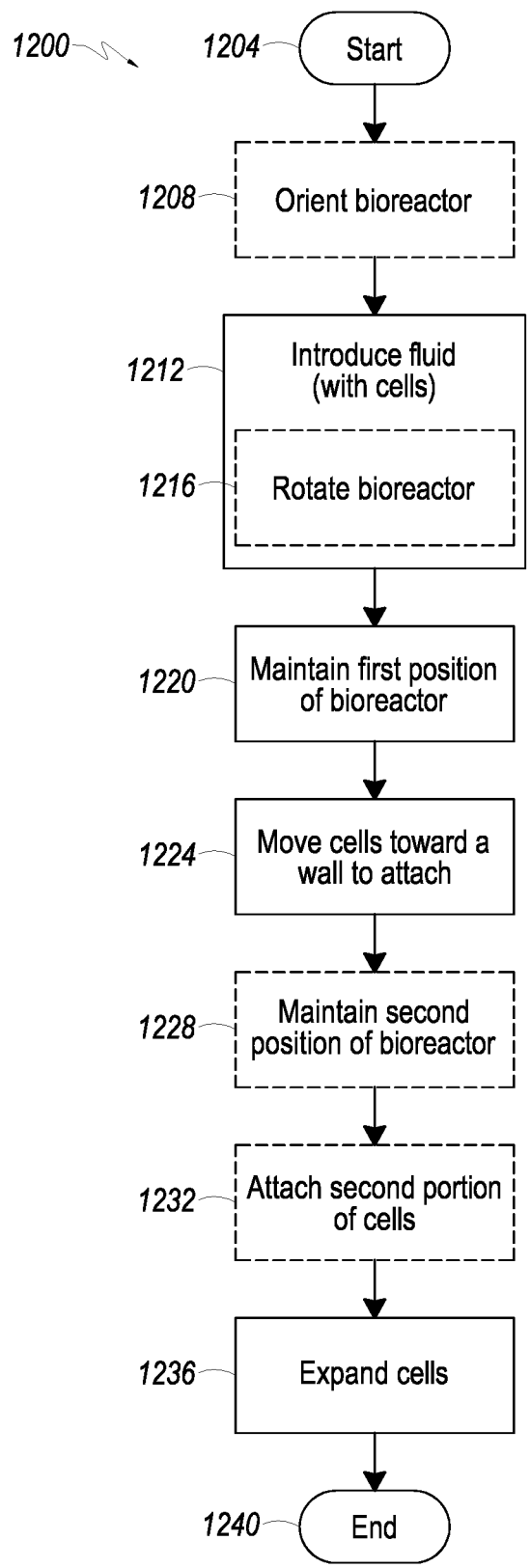
FIG. 12 illustrates a flow chart of a process for loading cells according to embodiments.
Figure 13:
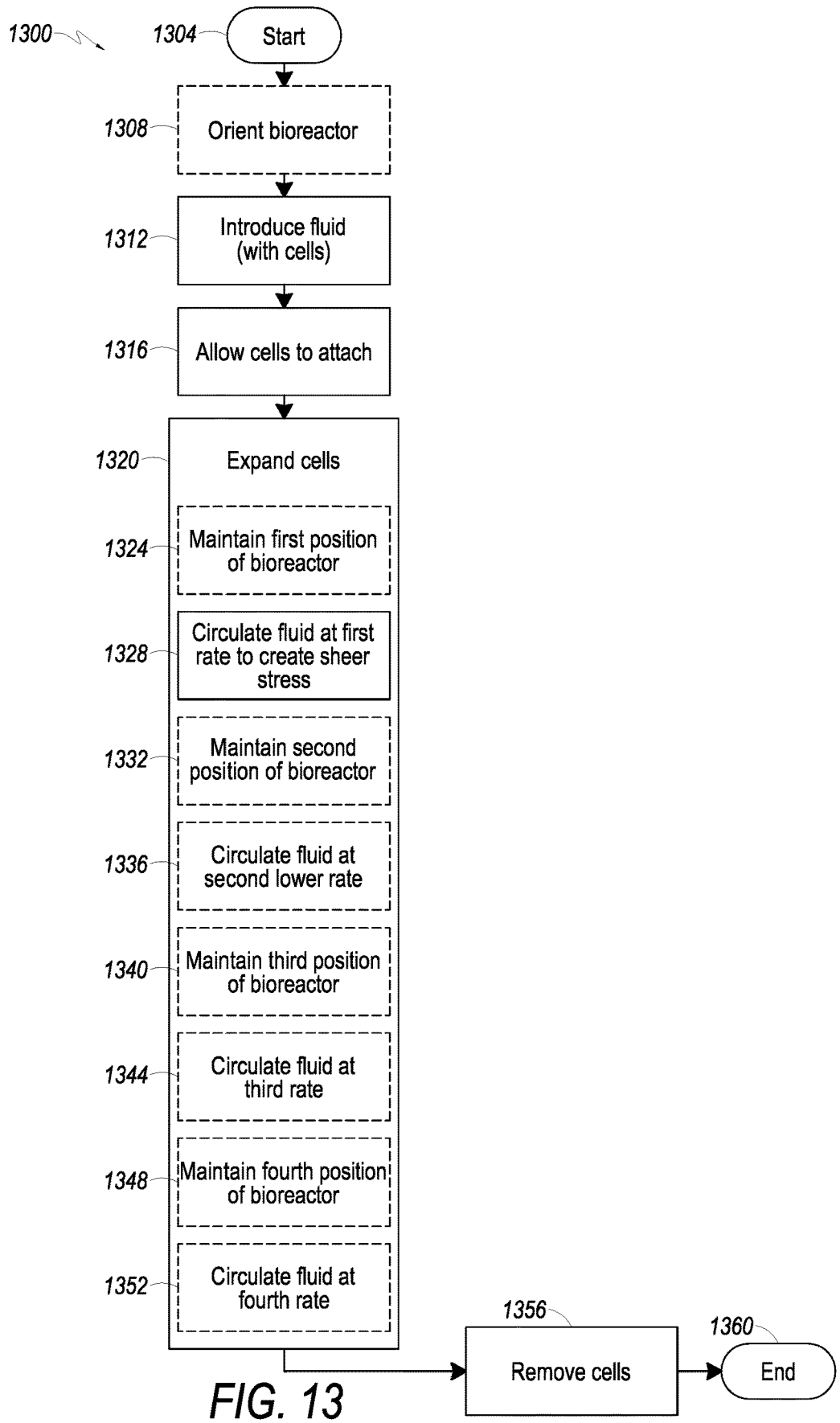
FIG. 13 illustrates a flow chart of a process for growing cells according to embodiments.
Figure 14:
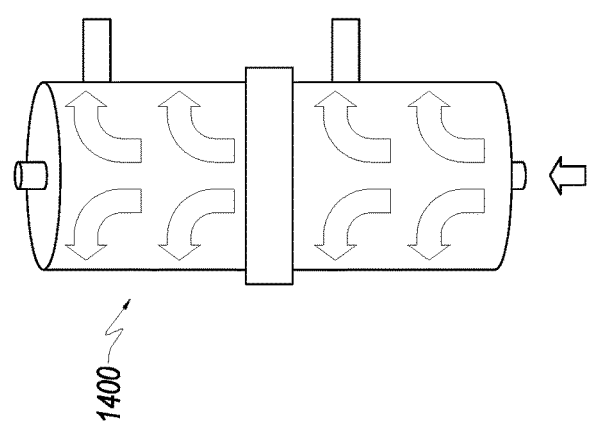
FIG. 14 illustrates fluid flow for movement of cells toward an inside wall of a hollow fiber.

Referring now to FIGS. 12-14, flow charts are shown that depict one or more processes for loading and/or growing cells. Although features of a CES (e.g., CES 10, 200, and/or 300) may be described as performing some of the steps of the flow charts 1200 and/or 1300, the present invention is not limited thereto. Indeed, other CES's with different features, not described herein or described above (e.g., CES's 10, 200, or 300), may be utilized in some embodiments. Accordingly, reference to features of a CES such as bioreactors 24, 201, 308, 416, 500, and/or 800 are provided for illustrative purposes only, and the flow charts 1200 and/or 1300 are not limited to use with any specific CES. Furthermore, in embodiments steps may be performed by a processor or by a computer system such as system 1800 illustrated in FIG. 18.

Flow chart 1200 illustrates a process for loading cells into a CES with a hollow fiber bioreactor according to embodiments. Flow chart 1200 starts at 1204, and passes to step 1208 where an optional step may be performed to initially orient a bioreactor. For example, in embodiments where a disposable set is used with a CES (e.g., FIG. 2), when a disposable set is connected to the CES, the bioreactor may be initially oriented in a horizontal position (FIG. 7). As part of the first step 1208 of flow 1200, the bioreactor (e.g., bioreactor 24, 201, 308, 416, 500, 800) may in some embodiments be moved/positioned to orient it in a different position, e.g., vertical.

From optional step 1208 flow 1200 moves to step 1212 where a first fluid comprising cells is introduced into a bioreactor. In embodiments, the bioreactor may include a hollow fiber membrane with a plurality of hollow fibers. The first fluid may flow into the plurality of hollow fibers. In embodiments, step 1212 may involve introducing a first liquid with cells into a loop, e.g., IC loop and then circulated through the bioreactor. In embodiments, the hollow fiber membrane with the hollow fibers may be part of one of bioreactors 24, 201, 308, 416, 500, and 800, which includes a longitudinal axis.

In some embodiments, step 1212 may involve some optional sub-steps. For example, at sub-step 1216 the hollow fiber bioreactor may be rotated while the fluid with cells is circulated through the bioreactor. For example, in one embodiment, the bioreactor may be rotated between a first initial horizontal position (FIG. 7) through 270 degrees (FIG. 10) and then back to the first position (FIG. 11). This may be repeated for a predetermined period of time or until all of the cells have been introduced into a loop.

After step 1212, flow 1200 moves to step 1220 where the bioreactor is maintained in a first position. In some embodiments, the first position may be selected to achieve a particular result when cells are being attached to the inside of hollow fibers. For example, in embodiments, it may be desirable to keep as many cells in the hollow fibers as possible, and not allow the cells to attach to other areas of the loop outside of the hollow fibers. In these embodiments, it may be desirable to use gravity to assist in keep the cells in the hollow fibers by maintaining a longitudinal axis of the bioreactor at an angle (greater than zero degrees) from a first horizontal position (FIG. 7). Having the longitudinal axis at an angle from a horizontal position, may assist in keeping the cells in the hollow fibers even if fluid (e.g., liquid) is circulating through the hollow fibers. In one embodiment, the longitudinal axis is maintained at about 90 degrees from a horizontal position (FIG. 8).

From step 1220, flow moves to step 1224, where cells are moved toward a wall of the hollow fibers to be attached to an inside surface of the hollow fibers. In embodiments, the cells may be moved by introducing a second fluid (e.g., liquid) into the hollow fiber bioreactor. As described above, the hollow fibers may allow fluid (e.g., liquid) to pass through the fiber wall from an IC side to an EC side. In embodiments, step 1224 may provide for fluid (e.g., liquid) to pass through the fiber wall, which may result in the cells being pushed to an inside surface of the hollow fiber wall. In some embodiments, step 1224 may also involve modifying portions of a CES to ensure that fluid (e.g., liquid) is transferred across the fiber wall. For example, an IC loop valve (e.g., valves 290 or 386) may be closed so that the fluid (e.g., liquid) is transported across the fiber wall (e.g., from an IC space to an EC space). In some embodiments, the movement of fluid (e.g., liquid) thorough the fiber wall may be referred to as ultrafiltration.

Referring to FIGS. 14-17, an embodiment of performing steps 1220 and 1224 is illustrated. As shown in FIG. 14, a bioreactor 1400 (e.g., with a plurality of hollow fibers) is in a substantially vertical position as may be performed as part of step 1220 noted above. As may be appreciated, having bioreactor 1400 in the substantially vertical position means that gravity acts on cells in the bioreactor which may tend to keep the cells within the hollow fibers of the bioreactor instead of being pushed out of the hollow fibers into other parts of an IC loop.

Figure 15:
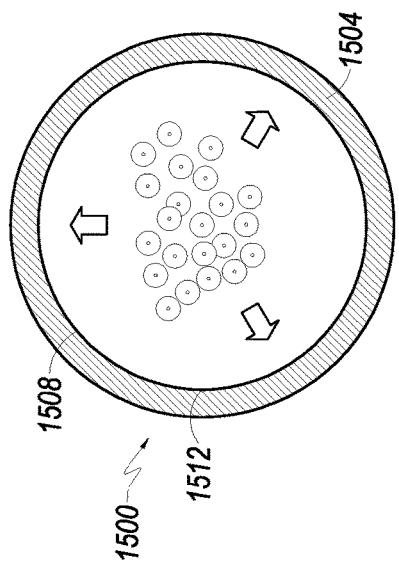
FIG. 15 illustrates a cross-section of a hollow fiber showing cells in the hollow fiber before moving toward an inside wall of the hollow fiber according to embodiments.
Figure 17:
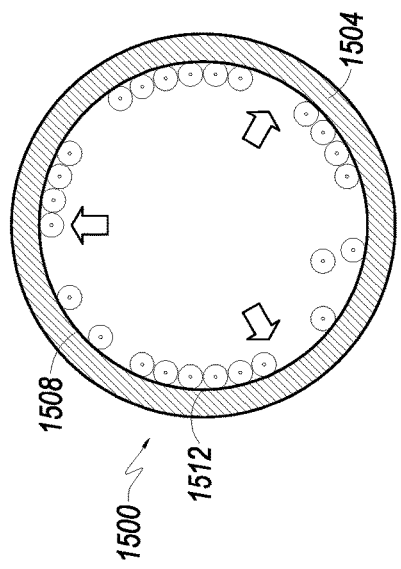
FIG. 17 illustrates a cross-section of a hollow fiber showing cells in the hollow fiber having moved toward an inside wall of the hollow fiber according to embodiments.
Figure 16:
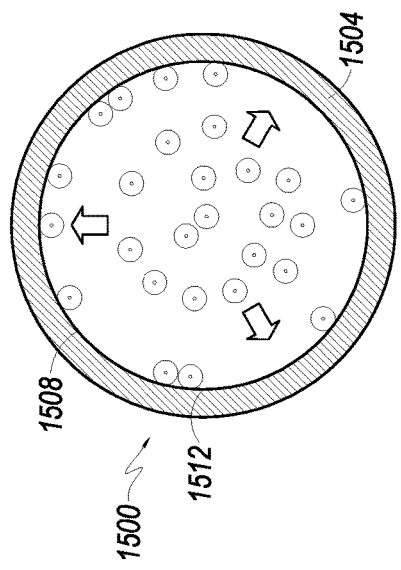
FIG. 16 illustrates a cross-section of a hollow fiber showing cells in the hollow fiber moving toward an inside wall of the hollow fiber according to embodiments.

FIGS. 15-17 illustrate a cross section of a hollow fiber 1500 according to an embodiment. FIG. 15 illustrates that cells are within the hollow fiber 1500. This may be the situation after step 1220 has been performed. FIG. 16 illustrates an example of the beginning of step 1224, where cells are being moved toward an interior surface 1508 of fiber wall 1504. As noted above, this may occur based on a second fluid (e.g., liquid) being introduced into the bioreactor (and consequently the hollow fibers) and then transported through fiber wall 1504. As shown in FIG. 16, cells have moved to surface 1508, which in this example includes a surface coating 1512. FIG. 16 illustrates that the cells begin to attach to surface 1508. FIG. 17 illustrates an example, after a predetermined period of time has passed, showing the cells having attached to the inside surface 1508.

It is noted that FIGS. 14-17 are provided merely to illustrate an example of how steps 1220 and 1224 may be performed, in some embodiments. It is noted that the present invention is not limited thereto. For example, although FIG. 17 may show all of the cells being attached to the surface 1508, in some embodiments only a portion of the cells may attach. As described below, some additional optional steps may be performed to attach a second portion (e.g., a portion remaining suspended in the fluid) of cells onto surface 1508.

Referring back to FIG. 12, after step 1224, an optional step 1228 may be performed to maintain a longitudinal axis of the hollow fiber bioreactor in a second position, which may aid in attaching cells to the inside surface of the hollow fibers. As one example, the hollow fiber bioreactor may be positioned in a horizontal position, see e.g., FIG. 7 and/or FIG. 9. This may allow gravity to settle cells that may remain suspended in the fluid after steps 1220 and 1224 to the inside surface of the hollow fiber. Optional step 1228 may be followed by optional step 1232 where a second portion of cells may attach to an inside surface of the hollow fiber.

Flow 1200 passes from optional step 1232 to step 1236, where cells are expanded. That is, cells are grown to an amount that exceeds an original amount, e.g., doubled. In embodiments, step 1236 may involve a number of sub-steps. For example, step 1236 may involve introducing a fluid into the hollow fiber bioreactor to feed the cells. In other embodiments, step 1236 may further involve circulating a fluid though an EC space to remove waste and provide nutrient and gasses for the cells to grow as describe above with respect to FIGS. 1A-1C. In some embodiments, step 1236 may involve one or more steps described below with respect to FIG. 13 and flow 1300. Flow 1200 ends at 1240.

Flow chart 1300 illustrates a process for growing cells in a CES with a hollow fiber bioreactor, according to embodiments. It is noted that in some embodiments flow 1300 may be used to expand particular types of cells that may respond to mechanical stimuli, such as endothelial cells or cardiomyocytes, as some non-limiting examples.

Flow chart 1300 starts at 1304, and passes to optional step 1308 where a bioreactor may be oriented. As noted above, in embodiments that provide for growing endothelial cells, the bioreactor may include a hollow fiber membrane with a number of hollow fibers each with particular structural characteristics that enhance or promote the expansion of some cells, endothelial cells. For example, the inner diameter and the surface roughness of the interior of the hollow fibers may be designed to optimize the growth of some cells.

Referring again to step 1308, in embodiments, where a disposable set is used with a CES (e.g., FIG. 4), when a disposable set is connected to the CES, the bioreactor (e.g., bioreactors 24, 201, 308, 416, 500, and/or 800) may be initially oriented in a horizontal position, accomplishing step 1308. In other embodiments, as part of step 1308 of flow 1300, the bioreactor may be moved/positioned to orient it at some angle from a horizontal position.

From optional step 1308 flow 1300 moves to step 1312 where a first fluid comprising cells is introduced into a hollow fiber bioreactor, e.g., into hollow fibers of the bioreactor. In embodiments, step 1312 may involve introducing a first fluid (e.g., liquid) with the cells into a loop, e.g., IC loop and then circulated through the hollow fiber bioreactor. In embodiments, the hollow fiber bioreactor may be one of bioreactors 24, 201, 308, 416, 500, and 800, which includes a longitudinal axis.

Step 1312 is followed by step 1316 where cells are allowed to attach. In embodiments, steps 1308, 1312 and 1316 may be performed as part of a process of loading cells into a CES and bioreactor. For example, in some embodiments, flow 1200 may be performed to load cells into a bioreactor. In these embodiments, steps 1308, 1312 and 1316 may include performing one or more steps described above for flow 1200.

After step 1316, flow 1300 passes to step 1320 where cells loaded/attached to an inside surface of hollow fibers are expanded. In some embodiments, step 1320 includes a number of sub-steps that are performed to expand the cells. As one example, optional step 1324 may be performed to orient the bioreactor in a first position. In some embodiments, the first position may be a substantially vertical position (e.g., see FIG. 8).

After optional sub-step 1324, a fluid may be circulated through the bioreactor at a first rate to feed the cells and create sheer stress on the cells in the bioreactor. The fluid may be media that includes protein, glucose, and/or other nutrients for cell growth. With respect to fluid sheer stress, it is believed that having an environment where cells are subjected to sheer stress may enhance the expansion of some cell types. As one example, endothelial cells may in some embodiments expand more readily if subjected to a threshold amount of fluid sheer stress. That is, cells that multiply during expansion may express characteristic of receptors indicative of endothelial cells, e.g., expression of vascular endothelial growth factor receptor. The threshold amount of sheer stress may in some embodiments be greater than or equal to 5 dyne/cm$^2$.

In other embodiments, the first rate may create fluid sheer stress on the cells, but be less than the threshold amount. In some embodiments, as described in greater detail below, the conditions in the bioreactor may be controlled so as to create an environment for enhancing growth of a particular cell type, e.g., endothelial cells. In these embodiments, a combination of parameters (e.g., mechanical stimulus) may be controlled, which in combination enhance the expansion of the cells. In some embodiments, any one parameter value may not result in enhanced expansion, but the combination results in enhanced cell expansion.

With respect to endothelial cells, a first flow rate used at step 1328 may result in sheer stress less than the threshold, however in combination with hollow fibers with particular structural features (e.g., inner diameter size, undulating surface features) and/or other fluid conditions (e.g., pulsatile fluid flow), the flow rate may result in enough sheer stress to provide enhanced expansion of cells, e.g., endothelial cells.

For example, the flow rate used at step 1328 may in embodiments result in sheer stress on the cells that is greater than about 0.01 dyne/cm$^2$, greater than about 0.02 dyne/cm$^2$, greater than about 0.03 dyne/cm$^2$, greater than about 0.04 dyne/cm$^2$, greater than about 0.05 dyne/cm$^2$, greater than about 0.06 dyne/cm$^2$, greater than about 0.07 dyne/cm$^2$, greater than about 0.08 dyne/cm$^2$, greater than about 0.09 dyne/cm$^2$, greater than about 0.1 dyne/cm$^2$, greater than about 0.15 dyne/cm$^2$, greater than about 0.2 dyne/cm$^2$, greater than about 0.25 dyne/cm$^2$, greater than about 0.3 dyne/cm$^2$, greater than about 0.35 dyne/cm$^2$, greater than about 0.4 dyne/cm$^2$, greater than about 0.45 dyne/cm$^2$, greater than about 0.5 dyne/cm$^2$, greater than about 0.55 dyne/cm$^2$, greater than about 0.6 dyne/cm$^2$, greater than about 0.65 dyne/cm$^2$, greater than about 0.7 dyne/cm$^2$, or even greater than about 0.75 dyne/cm$^2$. In other embodiments, the flow rate selected at step 1328 may in embodiments result in sheer stress on the cells that is less than about 5 dyne/cm$^2$, less than about 4 dyne/cm$^2$, less than about 3 dyne/cm$^2$, less than about 2 dyne/cm$^2$, less than about 1 dyne/cm$^2$, or even less than about 0.5 dyne/cm$^2$.

In embodiments, the first flow rate may be greater than about 0.5 ml/min, greater than about 1 ml/min, greater than about 1.5 ml/min, greater than about 2 ml/min, greater than about 2.5 ml/min, greater than about 3 ml/min, greater than about 3.5 ml/min, greater than about 4 ml/min, greater than about 4.5 ml/min, greater than about 5 ml/min, greater than about 10 ml/min, greater than about 15 ml/min, greater than about 20 ml/min, greater than about 25 ml/min, greater than about 30 ml/min, or even greater than about 35 ml/min. In other embodiments, the first flow rate may be less than about 400 ml/min, less than about 350 ml/min, less than about 300 ml/min, less than about 250 ml/min, less than about 200 ml/min, less than about 150 ml/min, less than about 100 ml/min, or even less than about 50 ml/min.

In embodiments, the first flow rate may be between about 20 ml/min and about 100 ml/min, such as about 40 ml/min or about 50 ml/min. In this embodiment, the flow rate may subject the cells to a fluid sheer stress of between about 0.1 dyne/cm$^2$ and about 1 dyne/cm$^2$, such as about 0.5 dyne/cm$^2$ or about 0.7 dyne/cm$^2$.

In embodiments, steps 1324 and 1328 may be performed for a first predetermined period of time. That is, the bioreactor may be maintained in the first position and fluid circulated at the first fluid rate for a first predetermined period of time. In embodiments, the first predetermined period of time may be less than about 1500 minutes, less than about 1400 minutes, less than about 1300 minutes, less than about 1200 minutes, less than about 1100 minutes, less than about 1000 minutes, less than about 900 minutes, less than about 800 minutes, less than about 700 minutes, less than about 600 minutes, less than about 500 minutes, or even less than about 400 minutes. In other embodiments, the first predetermined period of time may be greater than about 50 minutes, greater than about 100 minutes, greater than about 150 minutes, greater than about 200 minutes, greater than about 250 minutes, greater than about 300 minutes, greater than about 350 minutes, or even greater than about 400 minutes. In one specific embodiment, the first predetermined period of time may be between about 100 minutes and about 500 minutes, such as about 480 minutes.

Referring again to flow 1300, after step 1328, optional step 1332 may be performed to maintain the bioreactor in a second position. As noted above, in embodiments, the first position may result in the longitudinal axis being substantially vertical (FIG. 8). Optional step 1332 may therefore involve rotating the bioreactor 90 degrees from the first position so that a longitudinal axis is substantially horizontal (FIG. 9).

From optional step 1332, flow may pass to optional step 1336 where fluid is circulated at a second rate, which may be lower than the first rate. As a result of being at a lower rate, step 1336 may involve subjecting the cells to a reduced level of fluid sheer stress. It is believed that changing the position of the bioreactor and changing the flow rate may create a pulsatile fluid effect in the bioreactor, which may enhance the expansion of some cell types, e.g., endothelial cells. Without being bound by theory, it is believed that the pulsatile fluid effect may mimic the flow of blood in a living animal (e.g., a rate of a heartbeat).

In embodiments, the flow rate used at step 1336 may in embodiments result in sheer stress on the cells that is less than about 3 dyne/cm$^2$, less than about 2 dyne/cm$^2$, less than about 1 dyne/cm$^2$, less than about 0.5 dyne/cm$^2$, less than about 0.25 dyne/cm$^2$, or even less than about 0.1 dyne/cm$^2$.

In embodiments, the second flow rate may be less than about 100 ml/min, less than about 50 ml/min, less than about 25 ml/min, less than about 10 ml/min, less than about 5 ml/min, less than about 2.5 ml/min, less than about 1.5 ml/min, or even less than about 1 ml/min.

In one specific embodiment, the second flow rate may be less than about 50 ml/min such as about 20 ml/min or about 0 ml/min. In this embodiment, the flow rate may subject the cells to a fluid sheer stress of less than about 1 dyne/cm$^2$, such as about 0.1 dyne/cm$^2$ or about 0 dyne/cm$^2$.

In embodiments, steps 1332 and 1336 may be performed for a second predetermined period of time. That is, the bioreactor may be maintained in the second position and fluid circulated at the second fluid rate for a second predetermined period of time. In embodiments, the second predetermined period of time may be less than about 4000 minutes, less than about 3500 minutes, less than about 3000 minutes, less than about 2500 minutes, less than about 2000 minutes, less than about 1500 minutes, less than about 1400 minutes, less than about 1300 minutes, less than about 1200 minutes, less than about 1100 minutes, or even less than about 1000 minutes. In other embodiments, the second predetermined period of time may be greater than about 200 minutes, greater than about 300 minutes, greater than about 400 minutes, greater than about 500 minutes, greater than about 600 minutes, greater than about 700 minutes, greater than about 800 minutes, or even greater than about 900 minutes. In one specific embodiment, the second predetermined period of time may be between about 800 minutes and about 1100 minutes, such as about 960 minutes.

After optional step 1336, optional step 1340 may be performed to maintain the bioreactor in a third position. As noted above, in embodiments, the second position may result in the longitudinal axis being substantially horizontal (FIG. 9). Optional step 1340 may therefore involve rotating the bioreactor 90 degrees from the second position (180 degrees from the first position) so that a longitudinal axis is substantially vertical (FIG. 10).

From optional step 1340, flow may pass to optional step 1344 where fluid is circulated at a third flow rate. It is noted that in some embodiments, the third flow rate may be the same as the first rate. In other embodiments, the third flow rate may be a different flow rate, such as any of the rates described above for the first flow rate and/or the second flow rate. By changing the position of the bioreactor and changing the flow rate back to the third flow rate, the pulsatile fluid effect may be continued in the bioreactor.

In embodiments, steps 1340 and 1344 may be performed for a third predetermined period of time. That is, the bioreactor may be maintained in the third position and fluid circulated at the third flow rate for a third predetermined period of time. In embodiments, the third predetermined period of time may be less than about 1500 minutes, less than about 1400 minutes, less than about 1300 minutes, less than about 1200 minutes, less than about 1100 minutes, less than about 1000 minutes, less than about 900 minutes, less than about 800 minutes, less than about 700 minutes, less than about 600 minutes, less than about 500 minutes, or even less than about 400 minutes. In other embodiments, the third predetermined period of time may be greater than about 50 minutes, greater than about 100 minutes, greater than about 150 minutes, greater than about 200 minutes, greater than about 250 minutes, greater than about 300 minutes, greater than about 350 minutes, or even greater than about 400 minutes. In one specific embodiment, the third predetermined period of time may be between about 100 minutes and about 500 minutes, such as about 480 minutes.

After optional step 1344, optional step 1348 may be performed to maintain the bioreactor in a fourth position. As noted above, in embodiments, the third position may result in the longitudinal axis being substantially vertical (FIG. 10). Optional step 1348 may therefore involve rotating the bioreactor 90 degrees from the third position (270 degrees from the first position) so that a longitudinal axis is substantially horizontal (FIG. 11).

From optional step 1348, flow may pass to optional step 1352 where fluid is circulated at a fourth flow rate. It is noted that in some embodiments, the fourth flow rate may be the same as the second flow rate. In other embodiments, the fourth flow rate may be a different rate, such as any of the rates described above for the first flow rate and/or the second flow rate. By changing the position of the bioreactor and changing the flow rate back to the fourth flow rate, the pulsatile fluid effect may be continued in the bioreactor.

In embodiments, steps 1348 and 1352 may be performed for a fourth predetermined period of time. That is, the bioreactor may be maintained in the fourth position and fluid circulated at the fourth flow rate for a fourth predetermined period of time. In embodiments, the fourth predetermined period of time may be less than about 4000 minutes, less than about 3500 minutes, less than about 3000 minutes, less than about 2500 minutes, less than about 2000 minutes, less than about 1500 minutes, less than about 1400 minutes, less than about 1300 minutes, less than about 1200 minutes, less than about 1100 minutes, or even less than about 1000 minutes. In other embodiments, the fourth predetermined period of time may be greater than about 200 minutes, greater than about 300 minutes, greater than about 400 minutes, greater than about 500 minutes, greater than about 600 minutes, greater than about 700 minutes, greater than about 800 minutes, or even greater than about 900 minutes. In one specific embodiment, the fourth predetermined period of time may be between about 800 minutes and about 1100 minutes, such as about 960 minutes.

After optional step 1352, flow passes to step 1356 where the expanded cells are removed from the bioreactor. Step 1356 may, in embodiments, involve a number of sub-steps. For example, a harvest procedure may be performed as part of step 1356. The procedure may involve use of reagents (e.g., trypsin) to assist in detaching cells from an inside surface of hollow fibers. In some embodiments, flow of fluid through the IC loop and/or EC loop may be controlled to pass fluid from the EC loop to the IC loop to aid in detaching cells and removing them from the bioreactor, e.g., negative ultrafiltration. After step 1356, flow 1300 ends at step 1360.

Although flow charts 1200 and 1300 (FIGS. 12 and 13) has been described with steps listed in a particular order, the present invention is not limited thereto. In other embodiments, steps may be performed in different order, in parallel, or any different number of times, e.g., before and after another step. Also, as indicated above, flow charts 1200 and 1300 may include some optional steps or sub-steps. However, those steps above that are not indicated as optional should not be considered as essential to the invention, but may be performed in some embodiments of the present invention and not in others.

Figure 18:
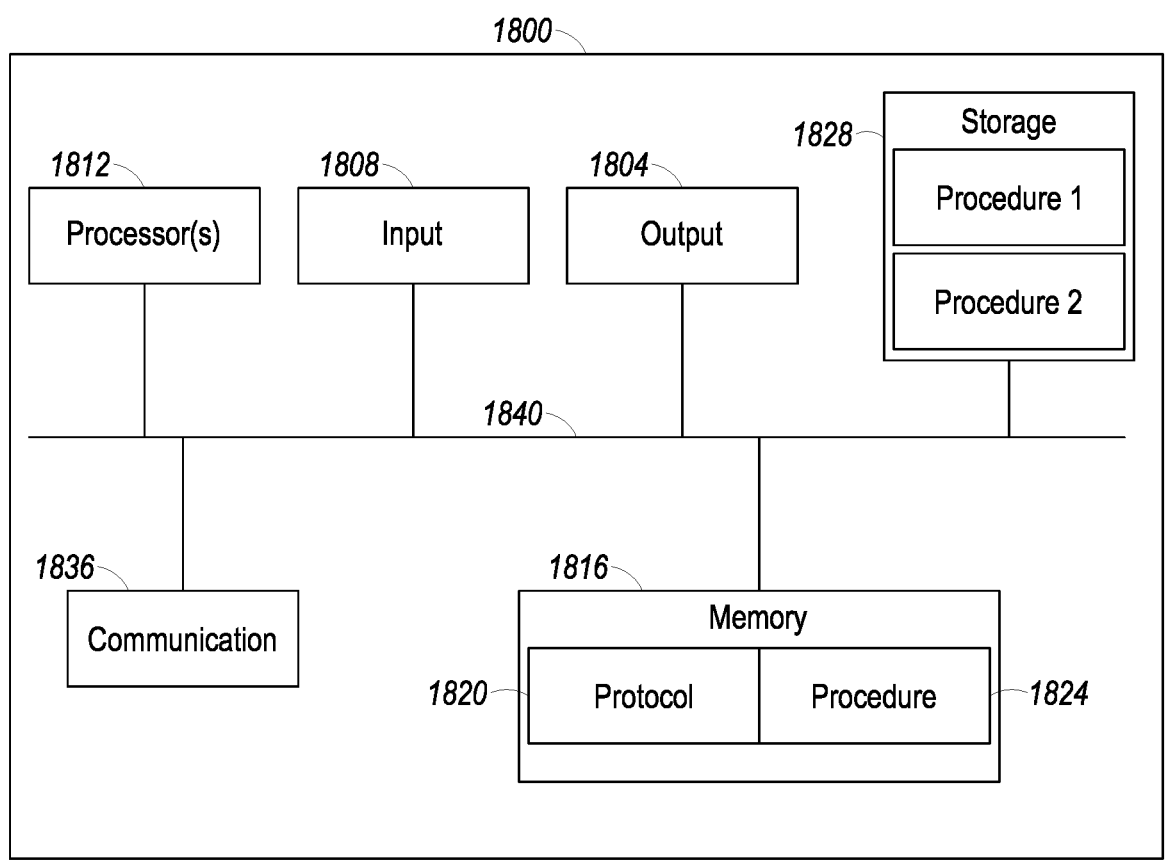
FIG. 18 illustrates a block diagram of a basic computer that may be used to implement embodiments.

FIG. 18 illustrates example components of a basic computer system 1800 upon which embodiments of the present invention may be implemented. Computer system 1800 may perform some steps in the methods for loading and distributing cells. System 1800 may be a controller for controlling features, e.g., flow control devices, pumps, valves, rotation of bioreactors, motors, etc., of CES systems 10, 430, 800, and 900 shown above in which cells are loaded and distributed for expansion.

Computer system 1800 includes output device(s) 1804, and/or input device(s) 1808. Output device(s) 1804 may include one or more displays, including CRT, LCD, and/or plasma displays. Output device(s) 1804 may also include a printer, speaker, etc. Input device(s) 1808 may include a keyboard, touch input devices, a mouse, voice input device, etc.

Basic computer system 1800 may also include a processing unit 1812 and/or a memory 1816, according to embodiments of the present invention. The processing unit 1812 may be a general purpose processor operable to execute instructions stored in memory 1816. Processing unit 1812 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits.

The memory 1816 may include any tangible medium for short-term or long-term storage for data and/or processor executable instructions, according to embodiments. The memory 1816 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc. In embodiments, system 1800 may be used to control the rotation of a bioreactor and/or various flow control devices, pumps, valves, etc. of CES systems. Memory 1816 can store protocols 1820 and procedures 1824, such as protocols and procedures for loading and expanding/feeding cells in a bioreactor, which would control operation of circulation pumps, valves, rotation of bioreactor(s), etc.

Storage 1828 may be any long-term data storage device or component. Storage 1820 may include one or more of the systems described in conjunction with memory 1816, according to embodiments. Storage 1828 may be permanent or removable. In embodiments, system 1800 is part of a CES system and storage 1828 may store various procedures for utilizing a CES system to load, distribute, attach, expand, and harvest cells of various types.

EXAMPLES

Described below are some examples of embodiments. However, it is noted that although specific protocols, cell types (e.g., endothelial cells) parameters, features, and/or values are described below, e.g., use of a CES, e.g., QUANTUM® cell expansion system, these are provided merely for illustrative purposes, and the present invention is not limited to the specific details provided below.

Example 1

Dynamic cell seeding of endothelial cells onto a fibronectin-coated hollow fiber membrane coupled with pulsatile, cyclic shear forces may serve to support the expansion of rat aorta endothelial cells (rAEC) to 4.0-5.4 cell doublings in less than 4 days with an automated system. Harvested cells may exhibit an elongated, cobblestone morphology. These data may suggest that the post-harvest rAEC phenotype may be characteristic of actively proliferating endothelial cells. This automated expansion protocol may permit the use of cell seeding densities that are an order of magnitude below that generally employed in static rAEC culture.

Angiogenesis and the vascularization of tissue for regenerative medicine is a complex developmental process requiring a dependable supply of actively growing endothelial cells (EC). Typically, only 50% of arteriovenous grafts remain patent one year after surgery in hemodialysis patients with vascular access dysfunction. This highlights the medical necessity in neovascularization. Moreover, the 3-D architecture of the cell culture matrix as well as mechano-signal transduction play important roles in EC proliferation. In terms of surface topography, an undulating surface with a radius of curvature greater than the cell length has been shown to enhance bovine endothelial cell (BEC) proliferation. Specifically, it was demonstrated that patterned circular matrixes with diameters on the order of 200 μm support cytoskeletal mechanical stresses and BEC growth through BrdUrd incorporation and Rho kinase signaling. Fortunately, this micro-geometry can be translated into a biopharma production application through the use of hollow fiber bioreactors that are manufactured under controlled extrusion processes. The coordination of fluid shear stress from 5-15 dynes/cm2 and VEGFR-2 expression are documented in the 2-D culture of human umbilical vein endothelial cells.

Consequently, modeling the intracapillary (IC) or lumen fluid shear stress over a range of flow rates, which generate a range of fluid sheer stress (0-5 dynes·cm−2) in a 2.1 m² surface area hollow fiber membrane (HFM) bioreactor for the purposes of supporting rat endothelial cell proliferation in a cyclic mode of circulation may be useful.

Figure 19:
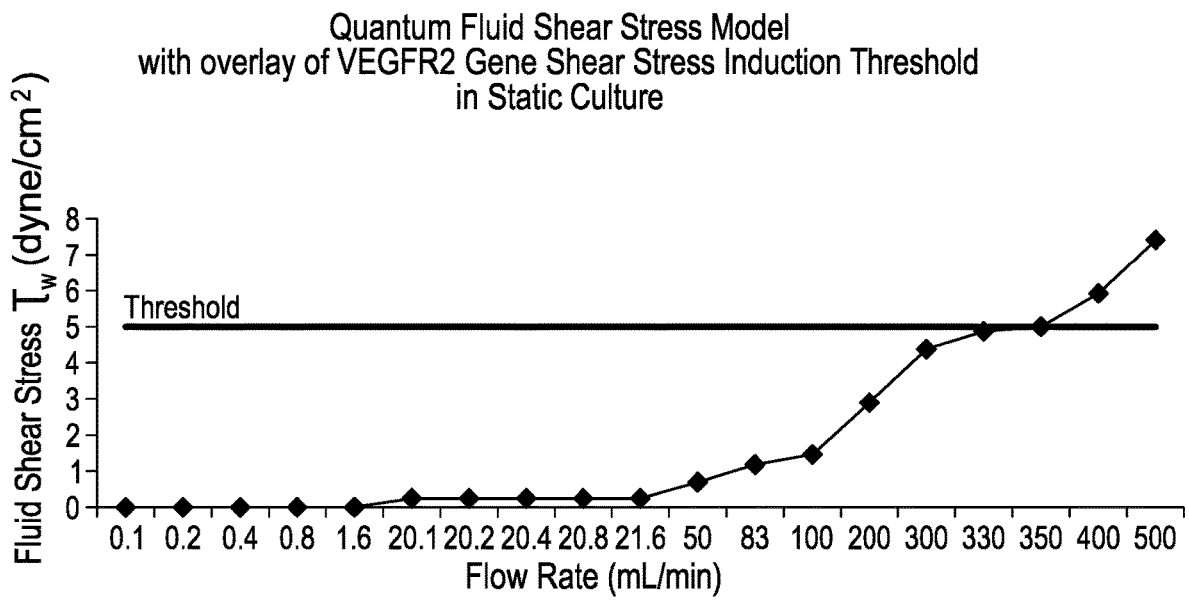
FIG. 19 illustrates a graph of a shear stress model for a cell expansion system over a threshold for vascular endothelial growth factor receptor 2 (VEGFR2) induction.

FIG. 19 illustrates a graph showing an example of the relationship between fluid shear stress and a bioreactor IC flow rate with respect to VEGFR2 induction from discontinuous cell culture.

Hemodynamic forces, in the form of pulsatile blood flow, may serve to elicit homeostasis and remodeling functions from endothelial cells at or near the resting pulse rate (bpm) of the host organism. Therefore, an approach may be to combine the 3-D architecture of an HFM bioreactor matrix with dynamic seeding, fluid shear stress, and undisturbed pulsatile flow to define a culture method for the expansion of rat aorta endothelial cells (rAECs) in the automated, functionally closed QUANTUM® cell expansion system (Terumo BCT).

The inoculum for the bioreactor may be prepared from adherent primary rat aorta endothelial cells (VEC Technologies) that may be grown to 80-90% confluency on hFibronectin-coated (5 µg·cm−2, BD 356008) TCPS flasks using MCDB-131-10 complete media (VEC Technologies) with 10% FBS (HyClone), antibiotics and glutamine at 37° C./5% $CO^2$ under humidified conditions. The rAECs may subsequently be harvested with a sterile solution of Trypsin-EDTA 0.25% (Gibco 25200-056), counted with a Beckman Coulter Vi-CELL® XR Cell Viability Analyzer, resuspended in 100 mL of complete media, and seeded into the Quantum System hFibronectin-coated (0.24 µg·cm−2) HFM bioreactor using a dynamic cell loading procedure.

In order to seed the rAEC inoculum onto the HFM, the bioreactor may be oriented in an oscillating position (−90° to 180°) for dynamic cell seeding. This process may begin by introducing the 100 mL cell suspension into the intracapillary loop using an IC inlet flow rate of 25 mL/min with the transmembrane fluid outlet through the EC waste valve to retain the cells within fiber lumen of the bioreactor. The initial step may be followed by a 22 mL chase volume of complete media to load the cells into the bioreactor. Step 3 may introduce a 50 mL volume of complete media to transport the cells to HFM lumen wall with the bioreactor in the vertical (90°) position and the IC outlet valve open. The cell loading procedure may be completed by reorienting the bioreactor to an inverted stationary position at 180° for a 24-hour period with the IC outlet closed. This may allow cells that do not reach the HFM to have the opportunity to adhere to the lumen wall. Complete media may be subsequently added to and circulated through the extracapillary (EC) loop which contains the Gas Transfer Module (GTM) in order to maintain the gas mixture, buffer capacity, and volume of the system.

After the cell attachment phase, programmed media additions may be sequentially increased (0.1, 0.3, to 0.6 mL·min−1) to support the characteristic rAEC growth and motility by reorienting the bioreactor under continuous shear stress conditions over a 48-hour period. One purpose for this approach may be to enhance the distribution of junctional proteins such as VE-cadherin whose expression has been shown to increase in EC borders under laminar flow.

TABLE 1

Quantum System input for automated rAEC feeding, IC shear stress, and pulsatile rate.

| Bioreactor Orientation | Interval (min) | IC Inlet *Q (mL · min$^{-1}$) | IC Circ *Q (mL · min$^{-1}$) | IC Shear Stress (dynes · cm$^{-2}$) | Est. IC Circ Pulsatile Rate (bpm) | EC Inlet *Q (mL · min$^{-1}$) | EC Circ *Q (mL · min$^{-1}$) |
|---|---|---|---|---|---|---|---|
| 90° | 480 | 0.1.-0.6 | 40-50 | 0.3 | 132-306 | 0 | 30 |
| 0° | 960 | 0.1-0.6 | 20 | 0.6-0.7 | 66-122 | 0 | 30 |
| 270° | 480 | 0.1-0.6 | 40-50 | 0.3 | 132-306 | 0 | 30 |
| 180° | 960 | 0.1-0.6 | 20 | 0.6-0.7 | 66-122 | 0 | 30 |

*Q = flow rate.

Cells may be expanded under laminar flow conditions with MCDG-131-10 complete media and mixed gas of 5% $CO^2$/20% $O^2$/75% $N^2$ at a temperature of 37° C. Glucose and lactate metabolite levels may be monitored throughout the culture process with Abbott i-STAT® analyzers and associated G and CG4+ cartridges. At the conclusion of the programmed expansion period, cells may be automatically harvested with 180 mL of sterile-filtered solution of Trypsin-EDTA 0.25%. Harvested samples may be counted, stained for membrane integrity (viability) with trypan blue, plated for morphology, analyzed for cell surface biomarker expression with a BD Canto II flow cytometer equipped using FACSDIVA software (v6.1.3), and evaluated for Dil acetylated-LDL internalization using a Zeiss Axio Observer A1 microscope equipped with Zen Pro software.

The Quantum System fluid circuit may be designed around two fluid loops: one loop for the intracapillary (IC) compartment of the bioreactor and the other for the extracapillary (EC) side of the system. Cells may be seeded to the IC compartment of the semi-permeable HFM bioreactor in order to control fluidic additions including inoculum, media, and supplements. In the EC compartment, gas exchange may be accomplished across the HFM and metabolite sampling may be achieved through the EC sampling port.

At the conclusion of cell expansion (2.8-3.8 days), the rAECs may be released and harvested with an automated task that combines the exchange of PBS, circulation of Trypsin-EDTA (10 min), and introduction of complete media for enzymatic neutralization into a single process. Harvested cells may be centrifuged at 500×g for 7 min at ambient conditions, aspirated to remove supernatant debris, and resuspended in either complete media for analysis or in cryopreservation media (5% DMSO, 45% MCDB-131-10, 50% FBS), for storage in vapor phase liquid nitrogen.

Three (3) Quantum HFM hFibronectin-coated bioreactor runs may be seeded respectively with 3.36×10$^7$, 1.40×10$^7$, 3.36×10$^7$ rAECs in exponential growth phase using 100 mL of complete media (MCDB-131-10 w/10% FBS HyClone and Antibiotics) using the "Dynamic Cell Loading" task (see Example 2 below). The cells may be subsequently grown ex vivo for a period of 2.8-3.8 days using an automated 8-hour/16-hour cyclic fluid shear-stress feeding and harvesting protocol (see Example 3 below). Samples of the harvested cell suspension may be enumerated by Vi-CELL XR Cell Viability System, assayed for morphology, and analyzed for CD31$^+$ CD45RA$^-$ surface biomarker expression by flow cytometry. Representative cell samples may also be analyzed for the internalization of Dil acetylated-LDL by fluorescent microscopy.

TABLE 2

Summary of Possible Results of rAEC Expansion in the Quantum System.

| Q-Run | Bioreactor Cell Seeding | rAEC Yield & Viability | Cell Culture Period, DS & DT | Bioreactor IC Circ Q & Max Shear Stress | Est. Max IC Pulsatile Rate (bpm) | rAEC Biomarker Phenotype | Dil Ac-LDL Internalization |
|---|---|---|---|---|---|---|---|
| Q1 | $3.36 \times 10^7$ $1,600 \cdot cm^{-2}$ | $1.47 \times 10^9$ 98.9% | 3.8 days DS 5.4 DT 16.7 hrs | 0-40 mL · $min^{-1}$ 0.6 dynes · $cm^{-2}$ | 40 mL · $min^{-1}$ 132-245 | CD31+ CD45RA− | Not Done |
| Q2 | $1.40 \times 10^7$ $667 \cdot cm^{-2}$ | $4.37 \times 10^8$ 98.3% | 2.8 days DS 5.0 DT 13.5 hrs | 20-50 mL · $min^{-1}$ 0.7 dynes · $cm^{-2}$ | 50 mL · $min^{-1}$ 165-306 | CD31+ CD45RA− | Positive |
| Q3 | $3.36 \times 10^7$ $1,600 \cdot cm^{-2}$ | $5.40 \times 10^8$ 97.8% | 2.8 days DS 4.0 DT 16.8 hrs | 20-50 mL · $min^{-1}$ 0.7 dynes · $cm^{-2}$ | 50 mL · $min^{-1}$ 165-306 | CD31+ CD45RA− | Positive |

Figure 20:
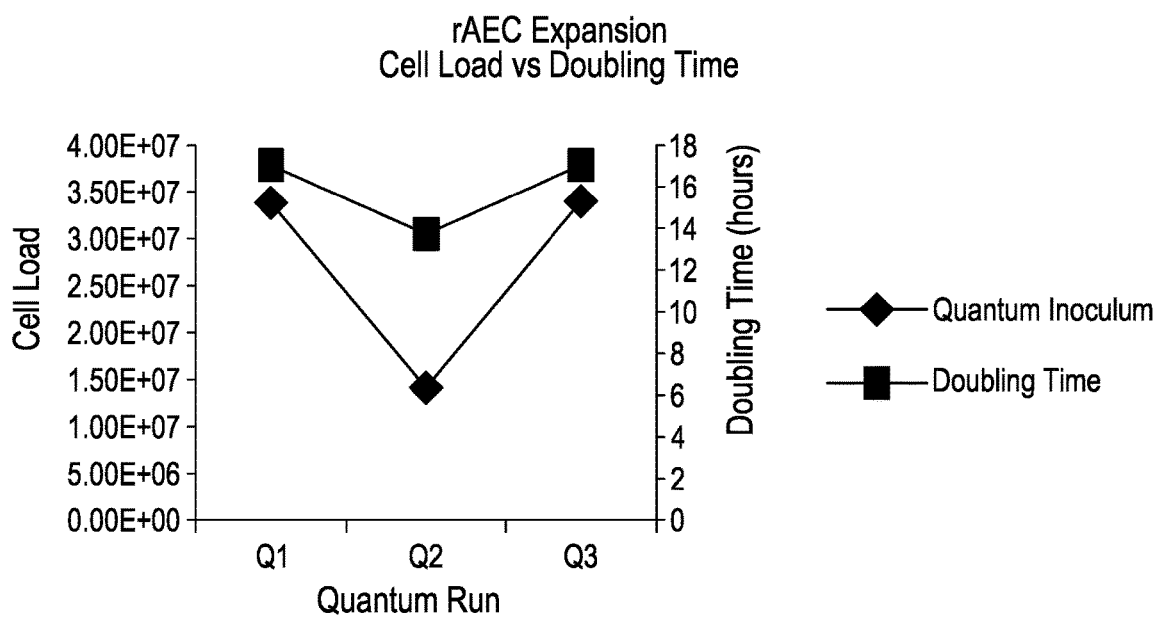
FIG. 20 illustrates a graph of cell load v. doubling time.

A comparison of the cell load and doubling time (DT) suggests that the rAEC seeding density of 667·cm−2 may generate a lower DT than the higher seeding density of 1,600·cm−2 particularly in the case of the Q2 and Q3 runs. This may be due, in part, to contact inhibitory effects of cells derived from a nearly confluent rAEC monolayer in the case of Q1 and Q3. FIG. 20 illustrates a graph showing cell load vs. doubling time for the three expansion runs described above.

Figure 21:
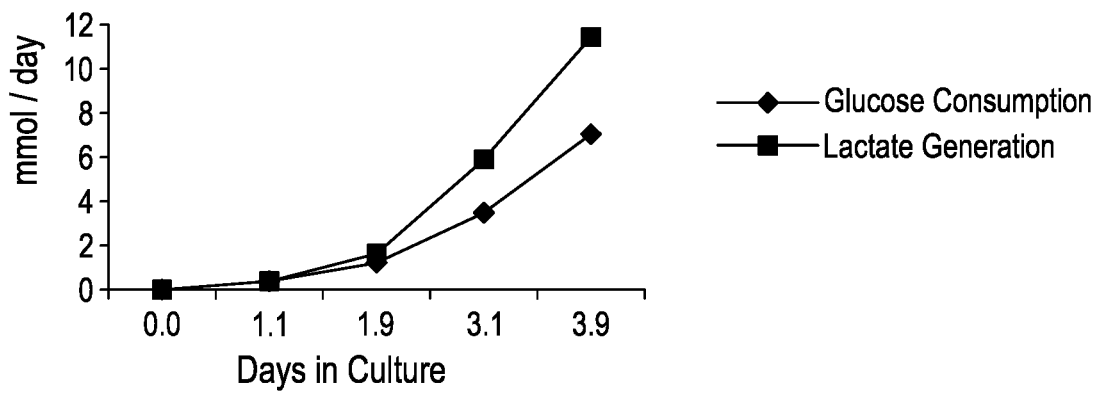
FIGS. 21-23 illustrate glucose consumption and lactate generation graphs.
Figure 22:
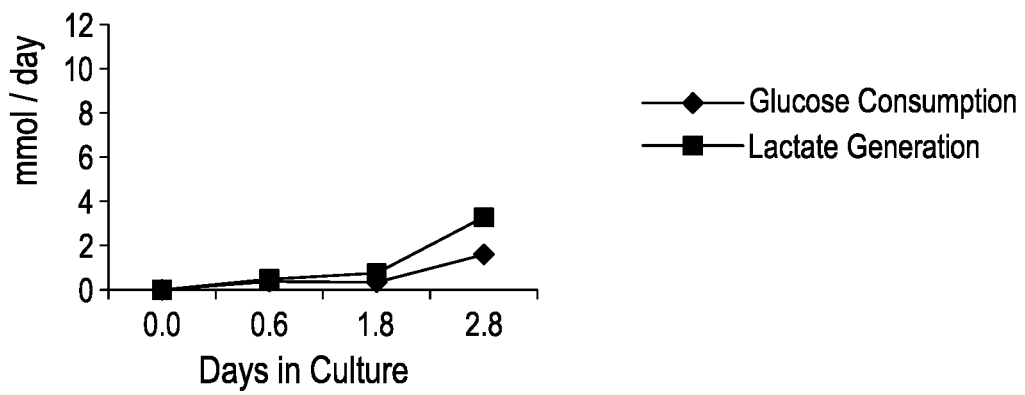
Figure 23:
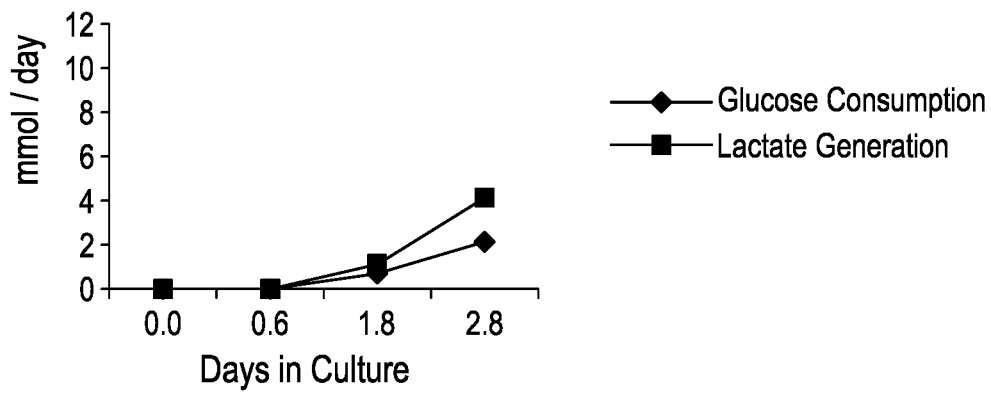

FIGS. 21-23 illustrate glucose consumption and lactate generation graphs and show the metabolic profile of the rAEC growth over 2.8 to 3.8 days in the three runs described above. Glucose and lactate values may be collected daily with Abbott i-STAT® meters. The differences in the slope of these plots can be attributed to the range of seeding densities (667-1,600 cells·cm−2) and IC circulation rates that may be explored. Media IC input rates may be increased from 0.1, 0.3, 0.6 mL·min−1 on a daily basis to maintain glucose levels on the order of 70 mg·dL−1 and lactate levels at or below 5 mmol·L−1.

Figure 24:
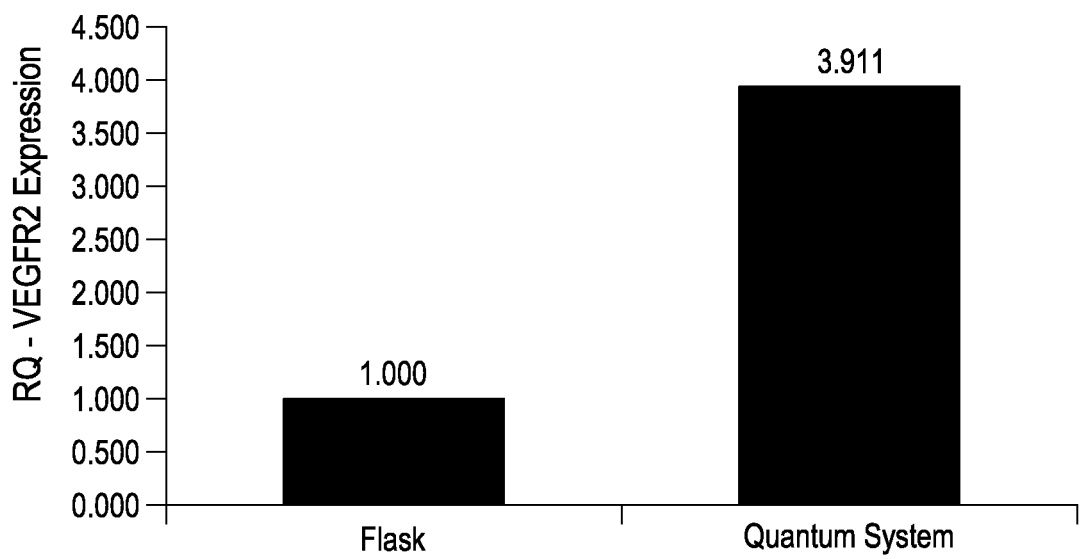
FIG. 24 illustrates a graph of relative quantification of VEGFR2 expression between two processes for growing endothelial cells.

FIG. 24 illustrate a graph showing the relative quantification of VEGFR2 expression comparing cells grown in a flask and cells grown in the Q3 run described above.

The exploration of microfluidics and their effects on endothelial cells have been performed in chambers with flat surfaces or in non-linear pathways with disruptive flow to study vascular dysfunction such as atherosclerosis and thrombosis. In contrast, laminar flow has been shown to enhance endothelial cell adhesion which is also dependent on cell seeding densities. For example, rAECs are typically seeded at densities of 3-4×$10^4$ cells·$cm^{-2}$ on flat TCPS surfaces (VEC Technologies). Alternatively, HFM bioreactors may be seeded with ECs at 6.67×$10^2$-1.6×$10^3$ cells $cm^{-2}$ utilizing a curved matrix. In feasibility experiments, a method may be defined to culture normal rAECs on a circular support with 3-D topographic features in an HFM bioreactor under continuous laminar flow conditions. The architecture of the HFM, with a radius of curvature greater than the cell length, has the potential to generate local mechanical stimuli that induce uniform endothelial cell proliferation. This proliferative effect can be further amplified with an undulating surface.

As a result, the study may suggest that dynamic cell seeding combined with cyclic shear stress culture, under continuous-pulsatile laminar flow, can support the efficient attachment and scale-up of endothelial cells for clinically relevant doses in a hollow fiber membrane bioreactor system. Moreover, the use of an automated control of pulsatile forces in an automated HFM system can potentially be extended to other cell types such as cardiomyocytes.

Example 2

Below are tables that provide non-limiting examples of a protocol (or portions of a protocol) that may be used when loading cells, e.g., endothelial cells according to embodiments. The example provides some values for settings that may be used in a CES, such as the QUANTUM cell expansion system to optimize the conditions for loading of some cell types, such as endothelial cells. The example is provided merely for illustrative purpose and other settings values may be used in other embodiments.

Furthermore, it is noted that in embodiments, the example below may be part of a larger protocol that includes other steps. For example, prior to loading cells in a CES/bioreactor, a protocol may include coating the bioreactor with a reagent to aid in the attachment of cells. As another non-limiting example, a priming step for adding fluid (e.g., liquid) into a dry CES may also precede the loading and coating portions of a protocol.

The purpose of this protocol may be to enable adherent cells to attach to the bioreactor membrane while allowing flow on the EC circulation loop. The pump flow rate to the IC loop may be set to zero.

Prior to loading the cells into all of the Quantum systems with Distribution and Rotation, install a Custom Task using the following existing/modified steps: Config>Task via the touch screen display or GUI. These solutions and corresponding volumes are based on the default settings for this task.

TABLE 3

Solutions for Attach Cells, Modification
Table 3: Solutions for Attach Cells

| Bag | Solution in Bag | Volume (estimate based on factory values) |
|---|---|---|
| Cell Inlet | None | N/A |
| Reagent | None | N/A |
| IC Media | Media with FBS | 6 mL/hour |
| Wash | None | N/A |
| EC Media | None | N/A |

Enter and confirm the values for each setting for Step 1 shown in Table 4.

TABLE 4

Vertical Cell Load - Config>Task>Custom>Save Modified, Step 1
Table 4: Load Cells into IC Loop

| Setting | Factory | Laboratory | Modifications |
| --- | --- | --- | --- |
| IC Inlet | Cell | | Cell |
| IC Inlet Rate | ~~50~~ | | 25 mL/min |
| IC Circulation Rate | ~~139~~ | | 0 mL/min |
| EC Inlet | None | | None |
| EC Inlet Rate | 0 | | 0 |
| EC Circulation Rate | 30 | | 30 |
| Outlet | EC Waste | | EC Waste |
| Rocker Control | In Motion (−90° to 180°) | | In Motion (−90° to 180°) |
| Stop Condition | Empty Bag | | Empty Bag |
| Estimated Fluid | Unknown | | Unknown |
| Omit or Include | Include | | Include |

Enter and confirm the values for each setting for Step 2 shown in Table 5.

TABLE 5

Vertical ARC Chase - Config>Task>Custom>Save Modified, Step 2
Table 5: ARC Chase

| Setting | Factory | Laboratory | Modifications |
| --- | --- | --- | --- |
| IC Inlet | IC Media | | IC Media |
| IC Inlet Rate | ~~50~~ | | 25 mL/min |
| IC Circulation Rate | ~~139~~ | | 0 mL/min |
| EC Inlet | None | | None |
| EC Inlet Rate | 0 | | 0 |
| EC Circulation Rate | 30 | | 30 |
| Outlet | ~~EC Waste~~ | | IC Waste |
| Rocker Control | In Motion (−90° to 180°) | | In Motion (−90° to 180°) |
| Stop Condition | IC Volume (22 mL) | | IC Volume (22 mL) |
| Estimated Fluid | 0.1 L | | 0.1 L |
| Omit or Include | Include | | Include |

Enter and confirm the values for each setting for Step 3 shown in Table 6.

TABLE 6

Membrane Transport - Config>Task>Custom>Save Modified, Step 3
Table 6: Task Settings to Transport Cells to Bioreactor IC HFM

| Setting | Factory | Laboratory | Modifications |
| --- | --- | --- | --- |
| IC Inlet | None | | IC Media |
| IC Inlet Rate | 0 | | 25 mL/min |
| IC Circulation Rate | 0 | | 0 |
| EC Inlet | EC Media | | None |
| EC Inlet Rate | 0 | | 0 |
| EC Circulation Rate | 0 | | 30 |
| Outlet | EC Waste | | EC Waste |
| Rocker Control | ~~Stationary (0°)~~ | | Stationary (90°) |
| Stop Condition | ~~Manual~~ | | IC Volume (50 mL) |
| Estimated Fluid | Unknown | | Unknown |
| Omit or Include | Include | | Include |

Enter and confirm the values for each setting for Step 4 shown in Table 7.

TABLE 7

Inverted Cell Attachment - Config>Task>Custom>Save Modified, Step 4
Table 7: Task Settings for Attach Cells in Bioreactor

| Setting | Factory | Laboratory | Modifications |
| --- | --- | --- | --- |
| IC Inlet | None | | None |
| IC Inlet Rate | 0 | | 0 |
| IC Circulation Rate | 0 | | 0 |
| EC Inlet | ~~EC Media~~ | IC Media | None |
| EC Inlet Rate | 0 | | 0.1 |
| EC Circulation Rate | 0 | | 30 |
| Outlet | EC Waste | | EC Waste |
| Rocker Control | ~~Stationary (0°)~~ | | Stationary (180°) |
| Stop Condition | ~~Manual~~ | | Time: 1,440 minutes |
| Estimated Fluid | Unknown | | Unknown |
| Omit or Include | Include | | Include |

Example 3

Below are tables that provide a non-limiting example of a protocol that may be used when expanding/feeding cells, e.g., endothelial cells according to embodiments. The example provides some values for parameters that may be used in a CES, such as the QUANTUM cell expansion system to optimize the conditions for growing/feeding some cell types, such as endothelial cells. The example is provided merely for illustrative purpose and other parameter values may be used in other embodiments.

Furthermore, it is noted that in embodiments, the examples below may be part of a larger protocol that includes other steps. For example, prior to expanding/feeding cells in a CES/bioreactor, a protocol may include coating the bioreactor with a reagent to aid in the attachment of cells. As another non-limiting example, loading cells (see, e.g., Example 2, above) into a bioreactor/CES may precede expanding/feeding of cells.

Continue with the modified pre-cultured hMSC expansion protocol for RAECs. To induce EC proliferation during growth phase of the expansion process, alternate the conditions within each 24-hour period between "Shear Stress" interval by using an IC Circ Q=40 mL/min for 8 hours and "Rest" interval with an IC Circ Q=0 mL/min for 16 hours as outlined in Tables 8-11. Repeat the following 48-hour feeding schedule during the growth phase of cell expansion and adjust IC Input per metabolite measurements.

Enter and confirm the values for each setting for Step 1 shown in Table 8.

TABLE 8

Vertical Feed Cells, Shear Stress 1 -
Config>Task>Custom>Save, Modified, Step 1
Table 8: Task Settings for Attach Cells, Step 5 (Feed Cells on Day 2)

| Setting | Factory | Laboratory | Modifications |
| --- | --- | --- | --- |
| IC Inlet | IC Media | | IC Media |
| IC Inlet Rate | 0.1 | | 0.1 |
| IC Circulation Rate | ~~20~~ | | 40 mL/min |
| EC Inlet | ~~EC Media~~ | IC Media | None |
| EC Inlet Rate | ~~0.1~~ | | 0 |
| EC Circulation Rate | 30 | | 30 |
| Outlet | IC Waste | | IC Waste |
| Rocker Control | ~~Stationary (0°)~~ | | Stationary (90°) |
| Stop Condition | ~~Manual~~ | | Time: 480 min |
| Estimated Fluid | Unknown | | Unknown |
| Omit or Include | Include | | Include |

Enter and confirm the values for each setting for Step 2 shown in Table 9.

TABLE 9

Horizontal Feed Cells, Rest Phase 1 -
Config>Task>Custom>Save, Modified, Step 2
Table 9: Task Settings for Attach Cells, Step 6 (Feed Cells on Day 2+)

| Setting | Factory | Laboratory | Modifications |
|---|---|---|---|
| IC Inlet | IC Media |  | IC Media |
| IC Inlet Rate | 0.1 |  | 0.1 |
| IC Circulation Rate | ~~20~~ |  | 0 mL/min |
| EC Inlet | ~~EC Media~~ | IC Media | None |
| EC Inlet Rate | ~~0.1~~ |  | 0 |
| EC Circulation Rate | 30 |  | 30 |
| Outlet | IC Waste |  | IC Waste |
| Rocker Control | Stationary (0°) |  | Stationary (90°) |
| Stop Condition | ~~Manual~~ |  | Time: 960 min |
| Estimated Fluid | Unknown |  | Unknown |
| Omit or Include | Include |  | Include |

Enter and confirm the values for each setting for Step 3 shown in Table 10.

TABLE 10

Vertical Feed Cells, Shear Stress 2 -
Config>Task>Custom>Save, Modified, Step 3
Table 10: Task Settings for Attach Cells, Step 7 (Feed Cells on Day 3+)

| Setting | Factory | Laboratory | Modifications |
|---|---|---|---|
| IC Inlet | IC Media |  | IC Media |
| IC Inlet Rate | 0.1 |  | 0.1 |
| IC Circulation Rate | ~~20~~ |  | 40 mL/min |
| EC Inlet | ~~EC Media~~ | IC Media | None |
| EC Inlet Rate | ~~0.1~~ |  | 0 |
| EC Circulation Rate | 30 |  | 30 |
| Outlet | IC Waste |  | IC Waste |
| Rocker Control | ~~Stationary (0°)~~ |  | Stationary (270°) |
| Stop Condition | ~~Manual~~ |  | Time: 480 min |
| Estimated Fluid | Unknown |  | Unknown |
| Omit or Include | Include |  | Include |

Enter and confirm the values for each setting for Step 4 shown in Table 11.

TABLE 11

Horizontal Feed Cells, Rest Phase 2 -
Config>Task>Custom>Save, Modified, Step 4
Table 11: Task Settings for Attach Cells, Step 8 (Feed Cells on Day 3+)

| Setting | Factory | Laboratory | Modifications |
|---|---|---|---|
| IC Inlet | IC Media |  | IC Media |
| IC Inlet Rate | 0.1 |  | 0.1 |
| IC Circulation Rate | ~~20~~ |  | 0 mL/min |
| EC Inlet | ~~EC Media~~ | IC Media | None |
| EC Inlet Rate | ~~0.1~~ |  | 0 |
| EC Circulation Rate | 30 |  | 30 |
| Outlet | IC Waste |  | IC Waste |
| Rocker Control | ~~Stationary (0°)~~ |  | Stationary (180°) |
| Stop Condition | ~~Manual~~ |  | Time: 960 min |
| Estimated Fluid | Unknown |  | Unknown |
| Omit or Include | Include |  | Include |

Program the IC Input Q based on the following schedule and adjust per glucose concentrations during the expansion process:
Day 2=0.1 mL/min
Day 3=0.3 mL/min
Day 4=0.6 mL/min
Day 5=1.2 mL/min
Day 6=1.6 mL/min It may be apparent to those skilled in the art that various modifications and variations can be made to the embodiments of the present invention described above without departing from their scope. Thus it should be understood that the invention is not be limited to the specific examples given, the embodiments described, or the embodiments shown in the figures. Rather, the invention is intended to cover modifications and variations.

While example embodiments and applications of the present invention have been illustrated and described, it is to be understood that the invention is not limited to the precise configuration, steps, and structures described above. Various modifications, changes, and variations apparent to those skilled in the art may be made in the arrangement, operation, and details of the methods and systems of the present invention disclosed herein without departing from the scope of the invention.

What is claimed is:

1. A method of growing cells in a hollow fiber bioreactor comprising a longitudinal axis, the method comprising:
   loading cells into the hollow fiber bioreactor, wherein the loading comprises:
      introducing a first fluid comprising the cells into a plurality of hollow fibers in the hollow fiber bioreactor;
      maintaining the longitudinal axis of the hollow fiber bioreactor at an angle greater than zero degrees from a first position, wherein the longitudinal axis is substantially horizontal when in the first position; and
      while maintaining the longitudinal axis of the hollow fiber bioreactor at the angle, moving the cells toward an inside wall of at least one of the plurality of hollow fibers by introducing a second fluid into the hollow fiber bioreactor, wherein a portion of the second fluid passes through a wall of the at least one of the plurality of hollow fibers and a portion of the cells attach to a lumen wall of the at least one of the plurality of hollow fibers, wherein the first fluid and the second fluid are different.

2. The method of claim 1, wherein the plurality of hollow fibers are part of an intracapillary space of the hollow fiber bioreactor and wherein the portion of the second fluid passes from the intracapillary space to an extracapillary space of the bioreactor.

3. The method of claim 2, wherein an outlet of the intracapillary space is closed during the moving the cells.

4. The method of claim 1, wherein the angle of the longitudinal axis is about 90 degrees from the first position.

5. The method of claim 1, wherein during the introducing the first fluid, rotating the longitudinal axis about 270 degrees from an initial position and back to the initial position.

6. The method of claim 1, further comprising:
   after the moving the cells, maintaining the longitudinal axis at about 180 degrees from the first position for a predetermined period of time to allow a second portion of cells to attach to the at least one of the plurality of hollow fibers.

7. The method of claim 1, further comprising:
   expanding the cells by circulating media in the hollow fiber bioreactor to feed the cells, wherein during the expanding the media is circulated at a first flow rate that subjects the cells to a fluid shear stress greater than about 0.01 dynes/cm$^2$ for a first predetermined period of time; and
   removing the cells from the hollow fiber bioreactor.

8. The method of claim 7, wherein the expanding comprises:
maintaining the longitudinal axis of the hollow fiber bioreactor substantially in a second position while circulating the media in the hollow fiber bioreactor during the first predetermined period of time, wherein the second position is substantially vertical.

9. The method of claim 8, wherein the expanding further comprises:
maintaining the longitudinal axis at about 90 degrees from the second position while circulating the media in the hollow fiber bioreactor for a second predetermined period of time.

10. The method of claim 9, wherein during the second predetermined period of time, the media is circulated at a second flow rate, which is less than the first flow rate.

11. The method of claim 9, wherein the expanding further comprises:
maintaining the longitudinal axis at about 180 degrees from the second position while circulating the media in the hollow fiber bioreactor for a third predetermined period of time.

12. The method of claim 11, wherein during the third predetermined period of time, the media is circulated at the first flow rate.

13. The method of claim 11, wherein the expanding further comprises:
maintaining the longitudinal axis at about 270 degrees from the second position while circulating the media in the hollow fiber bioreactor for a fourth predetermined period of time.

14. The method of claim 13, wherein during the fourth predetermined period of time, the media is circulated at a second flow rate, which is less than the first flow rate.

15. The method of claim 7, wherein the first flow rate is greater than about 1.5 ml/min.

16. The method of claim 7, wherein the first flow rate is less than about 400 ml/min.

17. The method of claim 1, wherein the cells comprise a first plurality of endothelial cells, wherein each of the hollow fibers comprises an inner diameter with a radius of curvature greater than a dimension of one of the first plurality of endothelial cells, and wherein each of the hollow fibers has undulating features on an interior surface;
the method further comprising:
expanding the first plurality of endothelial cells to generate a second plurality of endothelial cells greater than the first plurality of endothelial cells, wherein the expanding comprises circulating media through the hollow fiber membrane, the media circulating at a flow rate that subjects the first plurality of endothelial cells to a fluid shear stress that induces expression of vascular endothelial growth factor receptors; and
removing the second plurality of endothelial cells from the hollow fiber bioreactor.

18. The hollow fiber bioreactor of claim 17, wherein the interior surface of the plurality of hollow fibers comprises a surface roughness.

19. The method of claim 17, wherein an inner diameter of each of a portion of the plurality of hollow fibers is between about 175 microns and about 250 microns.

20. The method of claim 17, wherein the inner diameter of each of a portion of the plurality of hollow fibers is between about 200 microns and about 225 microns.

* * * * *